US007250551B2

(12) United States Patent
Tsai et al.

(10) Patent No.: US 7,250,551 B2
(45) Date of Patent: Jul. 31, 2007

(54) TRANSGENIC MICE EXPRESSING INDUCIBLE HUMAN P25

(75) Inventors: Li-Huei Tsai, Cambridge, MA (US); Ming-Sum Lee, New York, NY (US); Jonathan C. Cruz, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 335 days.

(21) Appl. No.: 10/625,986

(22) Filed: Jul. 24, 2003

(65) Prior Publication Data

US 2005/0014821 A1 Jan. 20, 2005

Related U.S. Application Data

(60) Provisional application No. 60/488,365, filed on Jul. 18, 2003, provisional application No. 60/398,541, filed on Jul. 24, 2002.

(51) Int. Cl.
*A01K 67/27* (2006.01)
*G01N 33/00* (2006.01)
*C12N 15/00* (2006.01)
*C12N 5/00* (2006.01)

(52) U.S. Cl. .............................. 800/18; 800/3; 800/12; 800/25; 435/325

(58) Field of Classification Search ................. 800/18, 800/25, 3, 12; 435/325
See application file for complete search history.

(56) References Cited

U.S. PATENT DOCUMENTS

| 4,736,866 A | 4/1988 | Leder et al. ................... 800/1 |
| 4,816,567 A | 3/1989 | Cabilly et al. .............. 530/387 |
| 4,870,009 A | 9/1989 | Evans et al. ................. 435/70 |
| 4,873,191 A | 10/1989 | Wagner et al. ........... 435/172.3 |
| 4,873,316 A | 10/1989 | Meade et al. ............... 530/412 |
| 5,223,409 A | 6/1993 | Ladner et al. ............. 435/69.7 |
| 5,225,539 A | 7/1993 | Winter ..................... 530/387.3 |

FOREIGN PATENT DOCUMENTS

| EP | 0 125 023 | 11/1984 |
| EP | 0 171 496 | 2/1986 |
| EP | 0 173 494 | 3/1986 |
| EP | 0 184 187 | 6/1986 |
| EP | 0 264 166 | 4/1988 |
| WO | WO 87/02671 | 3/1986 |
| WO | WO 86/01533 | 5/1987 |
| WO | WO 90/02809 | 3/1990 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 00/36093 | 6/2000 |
| WO | WO 01/57183 | 8/2001 |

OTHER PUBLICATIONS

Ristevski et al, Molecular Biotechnology, 29: 153163, 2005.*
Lucas et al, The EMBO Journal, 20(1 & 2): 27-39, 2001.*
Cameron, Molecular Biotechnology, 7: 253-265, 1997.*
Sigmund, Arterioscler Throm Vasc Biol 20: 1425-1429, 2000.*
Mayford et al, Science, 24: 1678-1683, 1996.*
Ahlijanian et al, PNAS, 97(6): 2910-1915, 2000.*
Ahlijanian et al., "Hyperphosphorylated tau and neurofilament and cytoskeletal disruptions in mice overexpressing human p25, an activator of cdk5," *Proc. Natl. Acad. Sci.*, 97:2910-2915 (2000).
Bibb et al., "Phosphyorylation of DARPP-32 by Cdk5 modulates dopamine signaling in neurons," *Nature*, 402:669-671 (1999).
Bibb et al., "Effects of chronic exposure to cocaine are regulated by the neuronal protein Cdk5," *Nature*, 10:376-380 (2001).
Delalle et al., "Temporal and spatial patterns of expression of p35, a regulatory subunit of cyclin-dependent kinase 5, in the nervous system of the mouse," *J. Neurocytol.*, 26:283-296 (1997).
De Strooper and Annaert, "Proteolytic processing and cell biological functions of the amyloid precursor protein," *J. Cell Sci.*, 113:1857-1870 (2000).
Dhavan and Tsai, "A Decade of Cdk5," *Nat. Rev. Mol. Cell Biol.*, 2:749-759 (2001).
Fischer et al., "Cyclin Dependent Kinase 5 Is Required for Associative Learning," *J. Neurosci.*, 22(9):3700-3707 (2002).
Grynspan et al., "Active site-directed antibodies identify calpain II as an early-appearing and pervasive component of neurofibrillary pathology in Alzheimer's disease," *Brain Res.*, 763:145-158 (1997).
Gupta et al., "Life Is a Journey . . . ," *Nat. Rev. Genet.*, 3:342-357 (2002).
Hsiao et al., "Correlative Memory Devicits, Aβ Elevation, and Amyloid Plaques in Transgenic Mice," *Science*, 274:99-102 (1996).
Keshvara et al., "Cyclin-Dependent Kinase 5 Phosphorylates Disabled 1 Independently of Reelin Signaling," *J. Neurosci.*, 22:4869-4877 (2002).
Khachaturian, "Diagnosis of Alzheimer's Disease," *Arch. Neuro.*, 42:1097-1105 (1985).

(Continued)

*Primary Examiner*—Deborah Crouch
*Assistant Examiner*—Magdalene Sgagias
(74) *Attorney, Agent, or Firm*—Banner & Witcoff, Ltd.

(57) ABSTRACT

Disclosed are improved methods of treating individuals with Alzheimer's disease (AD) as well as methods to diagnose AD in an individual. Also included are compounds and methods of identifying compounds to treat AD. The present invention also discloses methods for decreasing the phosphorylation of amyloid precursor protein (APP), including inhibiting phosphorylation of amino acid residue tyrosine 668 of APP and for reducing cleavage of APP. The present invention further discloses transgenic (Tg), non-human animals and cells expressing a p25 transgene that are models of neurodegenerative diseases. Embodiments of the present invention are directed to methods wherein the Tg animals and Tg cells of the invention are used to screen for modulators of neurodegenerative disorders. The Tg animals and cells of the present invention are useful for elucidating the mechanisms of neurodegenerative disorders.

11 Claims, 58 Drawing Sheets

(19 of 58 Drawing Sheet(s) Filed in Color)

OTHER PUBLICATIONS

Kusakawa et al., "Calpain-dependent Proteolytic Cleavage of the p35 Cyclin-dependent Kinase 5 Activator to p25," *J. Biol. Chem.* 275:17166 (1999).

Ledda et al., "Target-Derived GFRα1 as an Attractive Guidance Signal for Developing Sensory and Sympathetic Axons via Activation of Cdk5," *Neuron.*, 36:387-401 (2002).

Lewis et al., "Neurofibrillary tangles, amyotrophy and progressive motor disturbance in mice expressing mutant (P301L) tau protein," *Nat. Genet.*, 25:402-405 (2000).

Lewis et al., "Enhanced Neurofibrillary Degeneration in Transgenic Mice Expressing Mutant Tau and APP," *Science*, 293:1487-1491 (2001).

Li et al., "Regulation of NMDA receptors by cyclin-dependent kinase-5," *Proc. Natl. Acad. Sci. USA*, 98(22):12742-12747 (2001).

Mattson, "Cellular Actions of β-Amyloid Precursor Protein and its Soluble and Fibrillogenic Derivatives," *Physiol. Rev.*, 77:1081-1132 (1997).

Mayford et al., "Control of Memory Formation through Regulated Expression of a CaMKII Transgene," *Science*, 274:1678-1683 (1996).

Niethammer et al., "NUDEL Is a Novel Cdk5 Substrate that Associates with LISl and Cytoplasmic Dynein," *Neuron*, 28:697-711 (2000).

Nikoloic et al., "The cdk5/p35 kinase is essential for neurite outgrowth during neuronal differentiation," *Genes Dev.*, 10:816-825 (1996).

Patrick et al., "Conversion of p35 to p25 deregulates Cdk5 activity and promotes neurodengeneration," *Nature*, 402:615-622 (1999).

Price et al., "Amyloid beta amyloidosis in Alzheimer's disease," *Curr. Op. Neurol,*. 8:268-274 (1995).

Ramelot et al., "Phosphorylation-induced Structural Changes in the Amyloid Precursor Protein Cytoplasmic Tall Detected by NMR," *J. Mol. Biol.*, 307:871-884 (2001).

Sasaki et al., "A LISl/NUDEL/Cytoplasmic Dynein Heavy Chain Complex in the Developing and Adult Nervous System," *Neuron*, 28:681-696 (2000).

Sasaki et al., "Fyn and Cdk5 Mediate Semaphorin-3A Signaling, which Is Involved in REgulation of Dendrite Orientation in Cerebral Cortex," *Neuron*, 35:907-920 (2002).

Selkoe, "Transplanting cell biology into therapeutic advances in Alzheimer's disease," *Nature*, 399[Supp]:A23-A31 (1999).

Suri et al., "Catecholeminergic Cell Lines from the Brain and Adrenal Glands of Tyrosine Hydroxylase-SV40 T Antigen Transgenic Mice," *J. Neurosci.*, 13(3):1280-1291 (1993).

Tang et al., "An Isoform of the Neuronal Cyclin-dependent Kinase 5 (Cdk5) Activator," *J. Biol. Chem.* 270(45):26897-26903 (1995).

Taniguchi et al., "Calpain-mediated degradation of p35 to p25 in postmorten human and rat brains," *FEBS Lett.* 489:46-50 (2001).

Tomizawa et al., "Localization and Development Changes in the Neuron-Specific Cyclin-Dependent Kinase 5 Activator ($p35^{nck5a}$) in the Rat Brain," *Neurosci.*, 74(2):519-529 (1996).

Tsai et al., "p35 is a neural-specific regulatory subunit of cyclin-dependent kinase 5," *Nature* 371:419-423 (1994).

Tseng et al., "A survey of Cdk5 activator p35 and p25 levels in Alzheimer's disease brains," *FEBS Lett.* 523:58-62 (2002).

Yang and Hinds, "Increased Ezrin Expression and Activation by CDK5 Coincident with Acquisition of the Senescent Phenotype," *Mol. Cell*, 11:1163-1176 (2003).

Yankner, "Mechanisms of Neuronal Degeneration in Alzheimer's Disease," *Neuron*, 16:921-932 (1996).

Yoo and Lubec, "p25 protein in neurodegeneration," *Nature*, 411:763-764 (2001).

Younkin, "Evidence that Aβ42 Is the Real Culprit in Alzheimer's Disease," *Ann. Neurol.* 37:287-288 (1995).

English abstract of WO 93/01288.

Cruz et al., "Aberrant Cdk5 activation by p25 triggers pathologcial events leading to neurodegeneration and neurofibrillary tangles," *Neuron.*, 40(3):471-483 (2003).

Wang et al., "Cdk5 activation induces hippocampal CAl cell death by directly phosphorylating NMDA receptors," *Nat. Neurosci.*, 6(10):1039-1047 (2003).

Zhang et al., "Cyclin-dependent kinase inhibitors attenuate protein hyperphosphorylation, cytoskeletal lesion formation, and motor defects in Niemann-Pick Type C mice," *Am J Pathol.*, 165(3):843-853 (2004).

* cited by examiner

D

β cleavage site     α cleavage site

```
              596   601       611        621        631
              DAEF  RHDSGYEVHH QKLVFFAEDV GSNKGAIIGL MVGGVVIATV
(596-612) ─────────────────────
(596-625) ──────────────────────────────────────
     (602-612) ────────────────
     (602-625) ─────────────────────────────────
                     (613-649) ─────────────────────────────
```

```
              641        651        661        671        681        691
              IVITLVHLKK KQYTSIHHGV VEVDAAVTPE ERHLSKMQQN GYENPTYKFF EQMQN
(613-649) ────────
     (650-672) ──────────────────────────
     (650-676) ────────────────────────────
     (651-672) ────────────────────────
     (652-676) ───────────────────────────
     (652-672) ────────────────────────
                        (673-695) ───────────────────────
```

Heavy Membranes

B

Light Membranes

C Microsomes

D

A

B

A

E

G

H

I

E

```
        101
          ---LKAEEAGIGD TPNQEDQAAG HVTQARVASK DRTGNDEKKA
141
    KGADGKTGAK IATPRGAASP AQKGTSNATR IPAKTTPSPK TPPGSGEPPK
191
    SGERSGYSSP GSPGTPGSRS RTPSLPTPPT REPKKVAVVR TPPKSPSASK
241
    SRLQTAPVPM PDLKNVRSKI GSTENLKHQP GGGKVQIINK KLDLSNVQSK
291
    CGSKDNIKHV PGGGSVQIVY KPVDLSKVTS KCGSLGNIHH KPGGGQVEVK
341
    SEKLDFKDRV QSKIGSLDNI THVPGGGNKK IETHKLTFRE NAKAKTDHGA
391
    EIVYKSPVVS GDTSPRHLSN---
```

F

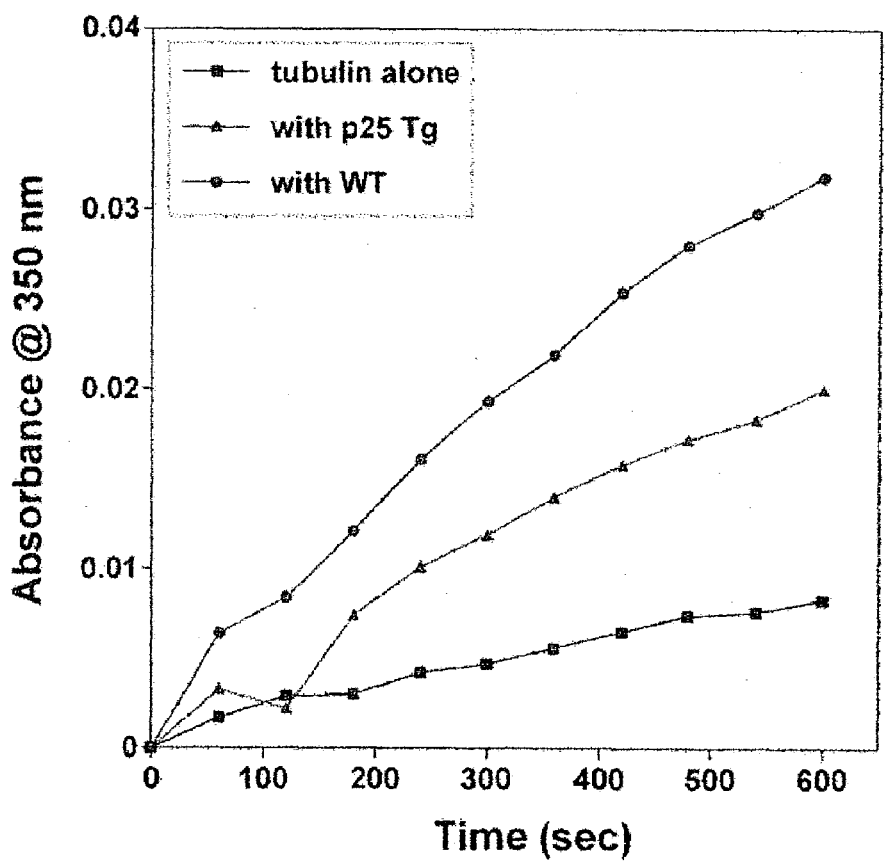

SEQUENCE LISTING

<160> NUMBER OF SEQ ID NOS: 19

<210> SEQ ID NO 1

```
<211> LENGTH: 38
<212> TYPE: DNA
<213> ORGANISM: Homo sapiens

<400> SEQUENCE: 1
taccgctcga gaattcccaa gaagaaacag tacacatc                           38

<210> SEQ ID NO 2
<211> LENGTH: 35
<212> TYPE: DNA
<213> ORGANISM: Homo sapiens

<400> SEQUENCE: 2
aatctagact cgagtgttct gcatctgctc aaaga                              35

<210> SEQ ID NO 3
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 3

Val Asp Ala Ala Val Thr Pro Glu Glu Arg His Cys
1               5                  10

<210> SEQ ID NO 4
<211> LENGTH: 12
<212> TYPE: PRT
<213> ORGANISM: Homo sapiens

<400> SEQUENCE: 4

Val Asp Ala Ala Val Thr Pro Glu Glu Arg His Cys
1               5                  10

<210> SEQ ID NO 5
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 5

Val Asp Pro Met Leu Thr Leu Glu Glu Gln Gln Cys
1               5                  10

<210> SEQ ID NO 6
<211> LENGTH: 12
<212> TYPE: PRT
<213> ORGANISM: Homo sapiens

<400> SEQUENCE: 6

Val Asp Pro Met Leu Thr Leu Glu Glu Gln Gln Cys
1               5                  10

<210> SEQ ID NO 7
<211> LENGTH: 12
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
```

```
<400> SEQUENCE: 7

Val Asp Pro Met Leu Thr Pro Glu Glu Arg His Cys
1               5                   10

<210> SEQ ID NO 8
<211> LENGTH: 12
<212> TYPE: PRT
<213> ORGANISM: Homo sapiens

<400> SEQUENCE: 8

Val Asp Pro Met Leu Thr Pro Glu Glu Arg His Cys
1               5                   10

<210> SEQ ID NO 9
<211> LENGTH: 10
<212> TYPE: PRT
<213> ORGANISM: Homo sapiens

<400> SEQUENCE: 9

Pro Lys Thr Pro Ala Lys Ala Lys Lys Leu
1               5                   10

<210> SEQ ID NO 10
<211> LENGTH: 27
<212> TYPE: PRT
<213> ORGANISM: Mus musculus
<220> FEATURE:
<221> NAME/KEY: MOD_RES
<222> LOCATION: (8)..(8)
<223> OTHER INFORMATION: PHOSPHORYLATION

<400> SEQUENCE: 10

Glu Glu Ala Gly Ile Gly Asp Thr Pro Ser Leu Glu Asp Glu Ala Ala
1               5                   10                  15

Gly His Val Thr Gln Ala Arg Met Val Ser Lys
            20                  25

<210> SEQ ID NO 11
<211> LENGTH: 24
<212> TYPE: PRT
<213> ORGANISM: Mus musculus
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (4)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 11

Ile Pro Ala Lys Thr Thr Pro Ser Pro Lys Thr Pro Pro Gly Ser Gly
1               5                   10                  15

Glu Pro Pro Lys Ser Gly Glu Arg
            20

<210> SEQ ID NO 12
<211> LENGTH: 17
```

```
<212> TYPE: PRT
<213> ORGANISM: Mus musculus
<220> FEATURE:
<221> NAME/KEY: MOD_RES
<222> LOCATION: (6)..(6)
<223> OTHER INFORMATION: PHOSPHORYLATION

<400> SEQUENCE: 12

Val Ala Val Val Arg Thr Pro Pro Lys Ser Pro Ser Ala Ser Lys Ser
1               5                   10                  15

Arg

<210> SEQ ID NO 13
<211> LENGTH: 10
<212> TYPE: PRT
<213> ORGANISM: Mus musculus
<220> FEATURE:
<221> NAME/KEY: MOD_RES
<222> LOCATION: (5)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 13

Ile Pro Ala Lys Thr Thr Pro Ser Pro Lys
1               5                   10

<210> SEQ ID NO 14
<211> LENGTH: 30
<212> TYPE: PRT
<213> ORGANISM: Mus musculus
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (4)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 14

Ser Gly Tyr Ser Ser Pro Gly Ser Pro Gly Thr Pro Gly Ser Arg Ser
1               5                   10                  15

Arg Thr Pro Ser Leu Pro Thr Pro Pro Thr Arg Glu Pro Lys
            20                  25                  30

<210> SEQ ID NO 15
<211> LENGTH: 12
<212> TYPE: PRT
<213> ORGANISM: Mus musculus
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 15
```

Ser Arg Thr Pro Ser Leu Pro Thr Pro Pro Thr Arg
1               5                   10

<210> SEQ ID NO 16
<211> LENGTH: 15
<212> TYPE: PRT
<213> ORGANISM: Mus musculus
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 16

Ser Arg Thr Pro Ser Leu Pro Thr Pro Pro Thr Arg Glu Pro Lys
1               5                   10                  15

<210> SEQ ID NO 17
<211> LENGTH: 10
<212> TYPE: PRT
<213> ORGANISM: Mus musculus
<220> FEATURE:
<221> NAME/KEY: MOD_RES
<222> LOCATION: (6)..(6)
<223> OTHER INFORMATION: PHOSPHORYLATION

<400> SEQUENCE: 17

Thr Pro Ser Leu Pro Thr Pro Pro Thr Arg
1               5                   10

<210> SEQ ID NO 18
<211> LENGTH: 23
<212> TYPE: PRT
<213> ORGANISM: Mus musculus
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 18

Ser Pro Ser Ala Ser Lys Ser Arg Leu Gln Thr Ala Pro Val Pro Met
1               5                   10                  15

Pro Asp Leu Lys Asn Val Arg
            20

<210> SEQ ID NO 19
<211> LENGTH: 21
<212> TYPE: PRT
<213> ORGANISM: Mus musculus
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 19

-continued

```
Thr Asp His Gly Ala Glu Ile Val Tyr Lys Ser Pro Val Val Ser Gly
1               5                   10                  15
Asp Thr Ser Pro Arg
            20
```

TRANSGENIC MICE EXPRESSING INDUCIBLE HUMAN P25

RELATED APPLICATIONS

This application claims priority to U.S. Provisional Patent Application No. 60/398,541, filed on Jul. 24, 2002, and the U.S. Provisional Application filed on Jul. 18, 2003 No. 60/488365, hereby incorporated by reference in their entirety for all purposes.

STATEMENT OF GOVERNMENT INTERESTS

This invention was funded by NIH grant no. GM 53049. The U.S. Government may have certain rights to this invention.

FIELD OF THE INVENTION

The invention relates in general to the treatment and diagnosis of individuals having a neurodegenerative disorder such as Alzheimer's disease (AD). The invention also relates to methods of inhibiting phosphorylation of amyloid precursor protein (APP) in a person afflicted with AD. The invention further relates to inhibiting production of beta-amyloid (Aβ) peptides in a person afflicted with AD.

The invention also relates in general to transgenic (Tg) animals and Tg animal cells having a first transgene encoding p25 operably linked to an inducible promoter and a second transgene encoding an inducer operably linked to a tissue-specific promoter. The invention further relates to methods for using the Tg animals and Tg cells for pharmaceutical screening and as research animals for modeling neurodegenerative diseases.

BACKGROUND OF THE INVENTION

Extracellular deposition of Aβ aggregates in the brain represents one of the defining pathologic features of AD (Price et al. (1995) *Curr. Op. Neurol.* 8:268; Selkoe (1999) *Nature* 399:A23; Yankner (1996) *Neuron* 16:921). Aβ is derived from proteolytic cleavage of APP, a type I transmembrane glycoprotein that belongs to a family of proteins that includes APP-like protein (APLP) 1 and 2. The processing of APP is initiated with the proteolysis of the extracellular/lumenal domain of the full length protein by either α- or β-secretase in the extracellular/lumenal domain, which leads to the generation of soluble N-terminal fragment sAPPα or sAPPβ and membrane anchored 83-residue or 99/89-residue membrane-bound C-terminal fragments (αCTF or βCTFs), respectively (De Strooper and Annaert (2000) *J Cell Sci.* 113:1857; Mattson (1997) *Physiol. Rev.* 77:1081; Younkin (1995) *Ann. Neurol.* 37:287). Subsequently, these fragments are cleaved by γ-secretase in the transmembrane region, resulting in the production of p3 (from αCTF) or the amyloidogenic peptides Aβ40 or Aβ42 (from βCTFs).

Cyclin-dependent kinase 5 (Cdk5) is a proline-directed protein kinase that phosphorylates serine and threonine residues. An interaction with either p35 or p39, two proteins abundantly expressed in post-mitotic neurons, is necessary for Cdk5 activation (Lew et al. (1994) *Nature* 371:423; Tang et al. (1995) *J. Biol. Chem.* 270:26897; Tsai et al. (1994) *Nature* 371:419). Cdk5 is a pleiotropic kinase that plays numerous functions in the mammalian central nervous system (Dhavan and Tsai (2001) *Nat. Rev. Mol. Cell Biol.* 2:749). The most well characterized role of Cdk5 is its involvement in the regulation of cortical development (Gupta et al. (2002) Nat. Rev. Genet. (2002) 3:342). Recent evidence also suggests the active participation of Cdk5 in axon guidance, dopamine signaling, and synaptic plasticity (Bibb et al. (2001) *Nature* 410:376; Bibb et al. (1999) *Nature* 402:669; Fischer et al. (2002) *J. Neurosci.* 22:3700; Ledda et al. (2002) *Neuron* 36:387; Li et al. (2001) *Proc. Natl. Acad. Sci. USA* 98:12742; Sasaki et al. (2002) *Neuron* 35:907).

Proteolytic cleavage of p35 generates p25, which leads to aberrant Cdk5 activation. Although p25 activates Cdk5, it is more stable and displays a different subcellular localization than p35. Conflicting reports exist as to whether p25 levels are increased in AD brains (Taniguchi et al. (2001) *FEBS Lett.* 489:46; Tseng et al. (2002) *FEBS Lett.* 523:58; Yoo and Lubec (2001) *Nature* 411:763). The accumulation of p25 is implicated in several neurodegenerative diseases. Current mouse models expressing p25, however, fail to effectively represent neurodegenerative phenotypes in vivo.

SUMMARY OF THE INVENTION

The present invention is based in part on the discovery that T668 phosphorylated APP (P-APP) is significantly upregulated in the brains of individuals having AD. The present invention is also based in part on the discovery that APP phosphorylation can facilitate the generation of Aβ, and can lead to the generation and/or progression of AD and symptoms associated therewith. Accordingly, it is an object of this invention to modify APP phosphorylation in order to reduce Aβ generation as a treatment for AD or symptoms associated therewith. The methods of the present invention are directed to treating an individual afflicted with AD in a manner to inhibit, reduce, prevent and/or reverse various AD symptoms such as behavioral symptoms, physical symptoms, and pathological symptoms.

In one embodiment, the present invention is directed to methods of inhibiting or reducing APP phosphorylation and/or hyperphosphorylation in an individual. The present invention is also directed to methods of therapeutically treating an individual afflicted with AD by inhibiting or reducing APP phosphorylation and/or APP hyperphosphorylation. Phosphorylation and/or hyperphosphorylation may be inhibited or reduced, for example, by administering a compound that prevents a kinase from phosphorylating APP and/or a carboxyl terminal fragment of APP. In one embodiment, the kinase is a cyclin-dependent kinase such as, for example, Cdk5. In another embodiment, the compound can be a cyclin-dependent kinase inhibitor such as, for example, roscovitine or butyrolactone. In yet another embodiment, the inhibitor can be olomoucine, flavopiridol or indirubin. In still another embodiment, phosphorylation of tyrosine 653, serine 655, threonine 668, serine 675, tyrosine 682, threonine 686 and/or tyrosine 687 of APP is inhibited.

Embodiments of the present invention are also directed to methods of diagnosing AD by detecting APP phosphorylation and/or hyperphosphorylation in a biological sample. Biological samples include, but are not limited to, spinal tissue, brain tissue, cerebrospinal fluid, blood, lymph, sputum, urine, and the like. Embodiments of the present invention are further directed to methods of determining whether an individual may be at risk of developing AD by detecting the level of APP phosphorylation and/or hyperphosphorylation in a test individual and comparing that level to a level indicative of a certain risk of developing AD. According to one aspect, the test level is compared to levels determined from individuals who do not have AD and from individuals who are at various stages of AD.

The present invention further provides a method of reducing APP cleavage by inhibiting an APP phosphorylation and/or hyperphosphorylation. The method includes reducing Aβ (e.g., Aβ(1-40), Aβ(1-42)) formation, and/or inhibiting one or more kinases (e.g., cyclin-dependent kinases, e.g., Cdk5). In one aspect of the present invention, APP phosphorylation may be inhibited by a cyclin-dependent kinase inhibitor such as butyrolactone, roscovitine, olomoucine, kenpaullone, alsterpaullone and the like. In another aspect, phosphorylation of tyrosine 653, serine 655, threonine 668, serine 675, tyrosine 682, threonine 686 and/or tyrosine 687 of APP is inhibited. The method can also include inhibiting a p25 activity such as the activation of a kinase. The method can include inhibiting a β-secretase activity such as cleaving APP.

The present invention further provides compounds for reducing APP cleavage, methods of identifying compounds that reduce symptoms associated with AD, and methods of identifying compounds that inhibit the progression of AD. The compounds can reduce Aβ (e.g., Aβ(1-40), Aβ(1-42)) formation and/or inhibit one or more kinases (e.g., cyclin-dependent kinases, e.g., Cdk5). In one aspect of the present invention, the compound may be a cyclin-dependent kinase inhibitor such as butyrolactone, roscovitine, olomoucine, kenpaullone, alsterpaullone and the like. In another aspect, the compound inhibits phosphorylation of tyrosine 653, serine 655, threonine 668, serine 675, tyrosine 682, threonine 686 and/or tyrosine 687 of APP. The compound can further inhibit a p25 activity, such as the activation of a kinase. The compound can also inhibit a β-secretase activity, such as cleaving APP.

The present invention is further based in part on inducible, Tg non-human animals overexpressing p25 in a tissue-specific manner. These animals exhibit many of the features of human tauopathies and AD in that they display progressive neurodegeneration, accumulation of hyperphosphorylated and aggregated tau, and neurofibrillary tangle (NFT) pathology. Induction of p25 in the Tg animals of the invention causes Cdk5 activity to be preferentially directed towards pathological substrates. The Tg animals of the present invention exhibit neuronal loss in the cerebral cortex and hippocampus, severe brain atrophy, reactive astrogliosis, and caspase-3 activation. The Tg animals of the invention also display endogenous tau hyperphosphorylation at many epitopes, accumulation of aggregated tau fibrils, and the progressive development of neurofibrillary pathology, APP phosphorylation, APP hyperphosphorylation, and up-regulation of C99 synthesis. Accordingly, it is an object of the invention to use the p25 Tg non-human animals described herein as an in vivo model of human neurodegenerative disorders such as tauopathies and AD.

In one embodiment, the present invention is directed to Tg non-human animals expressing p25 transgene (e.g., human or murine p25) and an inducer transgene. In one aspect, p25 expression is tissue-specific. In another aspect, the non-human animal is a mouse. In another aspect, p25 is overexpressed.

Another embodiment of the present invention is directed to Tg cells expressing a p25 transgene. In one aspect, the cells are neuronal cells. In another aspect, the neuronal cells are derived from the forebrain. In yet another aspect, the cells are isolated from the Tg non-human animals described herein.

The Tg animals and Tg cells of the present invention are useful models of neurodegenerative disorders, such as Alzheimer's disease. Accordingly, the Tg non-human animals and Tg cells described herein are useful for screening compounds that inhibit, reduce, prevent or reverse an activity, phenotype or symptom associated with the neurodegenerative disorders described herein. Thus, another embodiment of the present invention is directed to methods of screening compounds for the treatment of neurodegenerative disorders using the Tg, non-human animals and cells described herein. In yet another embodiment, the Tg animals and cells of the present invention are used to further elucidate the mechanisms of neurodegenerative disorders.

Combinations of features and methods described herein are also provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 22:
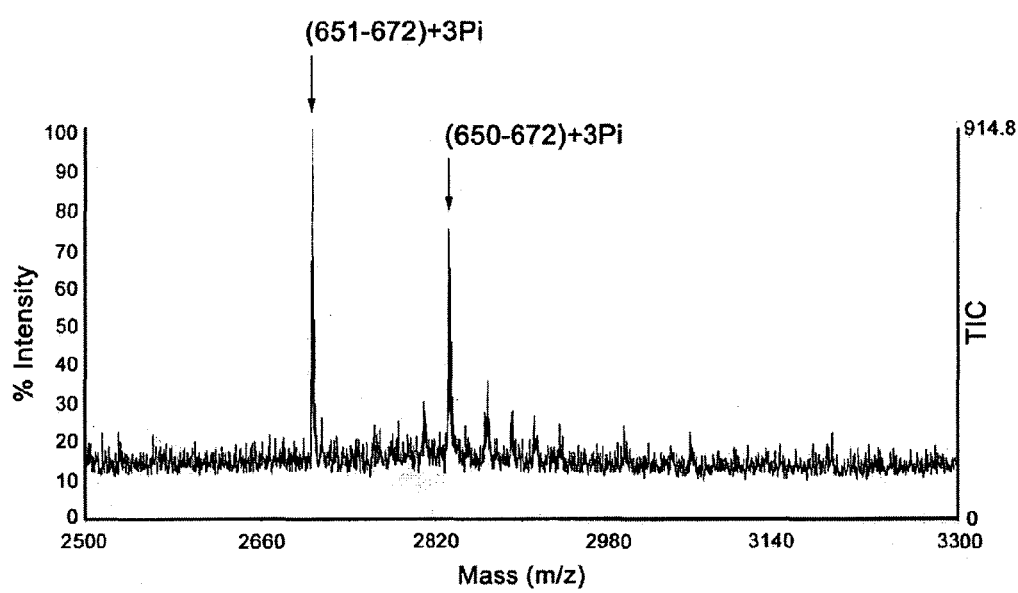

FIG. 22 depicts a partial MALDI spectrum of APP C-terminal fragments (CTFs) from CAD cells overexpressing human APP. APP CTFs were immunoprecipitated using APP C-terminal antibody (C1/6.1), resolved on SDS-PAGE, digested with trypsin and analyzed by MALDI-TOF mass spectrometry. MS peaks representing phosphorylated tryptic peptides are indicated.

Figure 23:

FIGS. 23A-23B depict that T668 phosphorylated APP does not co-localize with lysozome marker, cathepsin B (A) or with ER marker GP96 (B) in AD brains. Scale bars: 5 μm.

FIGS. 24A-24D depict double immunofluorescence staining of rat primary cortical neurons. Co-staining of P-APP and trans-Golgi marker adaptin-γ (a) and cis-Golgi marker GM130 (B). (C, D) Co-staining of P-APP and BACE1 in 10 day in vitro cortical cultures. Scale bars: 5 μm (A, B, D) and 20 μm (C).

Figure 25:
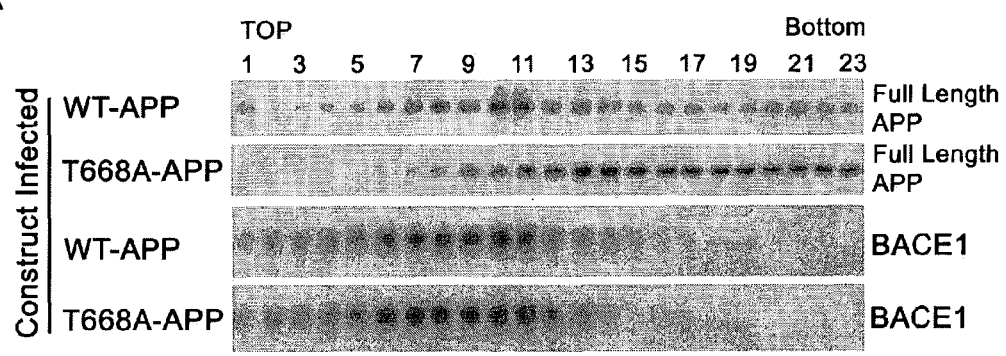
Figure 25:
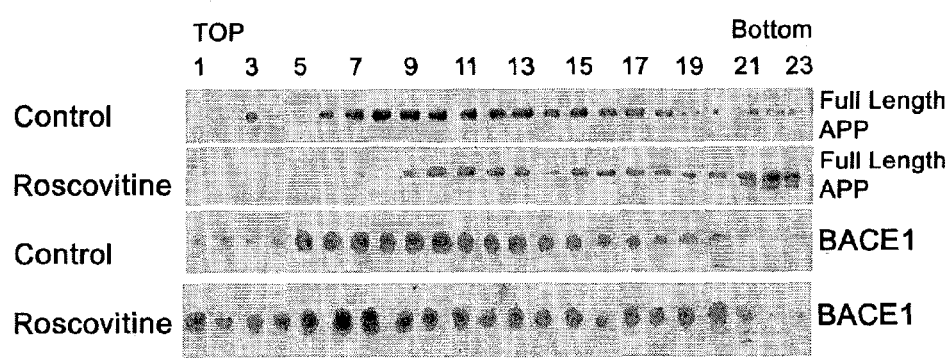

FIGS. 25A-25B depict immunoblots showing distribution of APP and BACE1 in iodixanol step gradient. (A) 2 day in vitro primary cortical neurons were infected with recombinant herpes simplex virus (HSV) expressing WT or T668A mutant APP. Twenty hours post infection, cell homogenates were fractionated through an iodixanol step gradient and the distributions of APP and BACE1 were analyzed. (B) 2 day in vitro primary cortical neurons were infected with HSV expressing WT APP for 16 hrs and then treated with 10 μm roscovitine for an additional 8 hours (vehicle as control). Cell homogenates were fractionated and the distributions of APP and BACE1 were analyzed by Western blot analysis.

Figure 26:
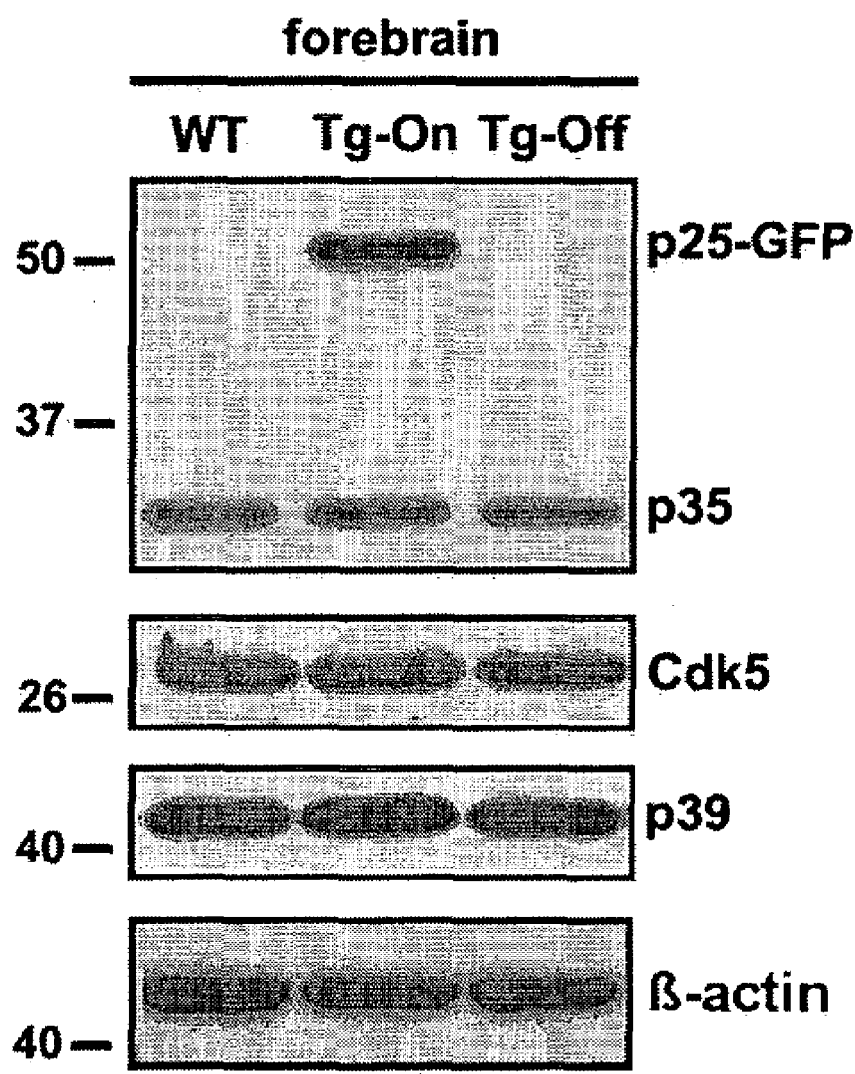
Figure 26:
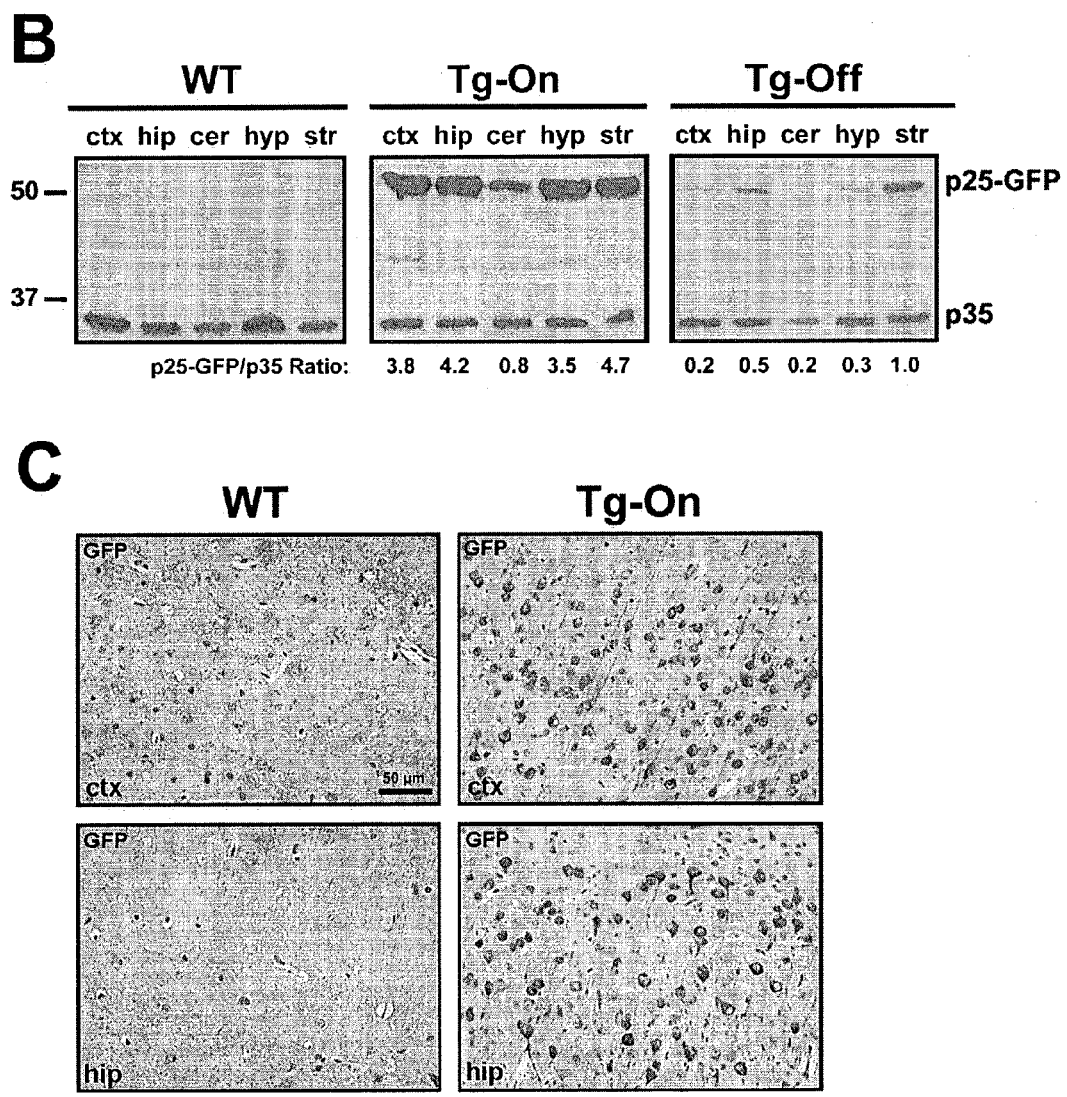

FIGS. 26A-26C depict brain regional p25 expression and Cdk5 activation. (A) Immunoblot analysis of WT, induced (Tg-On) and non-induced (Tg-Off) Tg mice forebrain lysates using p35, Cdk5, p39, or α-actin antibodies. (B) p35 immunoblot analysis of WT, induced (Tg-On) and non-induced (Tg-Off) Tg mice brain lysates derived from the cortex (ctx), hippocampus (hip), cerebellum (cer), hypothalamus (hyp), or striatum (str). Ratios of p25-GFP/p35 were determined by densitometry analysis using FujiFilm Science Lab Image Gauge software. (C) Green fluorescent protein (GFP) immunoreactivity in coronal sections of the cerebral cortex (upper panels) and CA1 region of the hippocampus (lower panels) from WT and Tg-On mice. All Tg mice were induced, or non-induced, for 5 weeks except in (C), wherein the mice were induced for 8 weeks.

FIGS. 27A-27J depict progressive neurodegeneration in the cerebral cortex and hippocampus. (A) Substantial forebrain atrophy in 12 week induced p25 Tg compared to WT littermate. (B) Significant reductions in brain weight in p25 Tg mice. Whole brains from WT, Tg-Off, and Tg-On littermates, induced for various periods of time, were dissected and weighed. Error bars represent SEM values for WT and Tg-Off littermates (n=3); WT and Tg-On littermates induced for 5 weeks (n=5), 7-8 weeks (n=11), or >12 weeks (n=5). P values (p<0.005; *p<0.0001) were determined using a two-tailed, non-parametric, unpaired Student's T-test. (C) Decrease in thickness and neuronal density in the cortex (upper panels) and dentate gyrus of the hippocampus (lower panels) in induced p25 Tg mice. Coronal brain sections from Tg-Off and Tg-On littermates, non-induced or induced for 12 weeks, were stained with Nissl and Luxol fast blue. (D and E) Progressive neuronal loss in the cortex (D) and hippocampus (E) of p25 Tg mice. Coronal brain sections from WT or Tg-On mice induced for 8 or 12 weeks were immunostained with the neuron-specific marker, NeuN. The same results were found when brain sections were immunostained with the marker HuC/D. (F) Quantification of neuronal loss in induced and non-induced p25 Tg mice as compared to WT mice. The neuronal density of various coronal brain sections from WT, Tg-On, and Tg-Off mice (n=12) were determined as described in Experimental Procedures. P values (*p<0.05; ***p<0.0001) were determined using a two-tailed, non-parametric, unpaired Student's T-test. (G) Increased glial fibrillary acidic protein (GFAP) immunohistochemical staining in coronal sections of the cerebral cortex (upper panels) and hippocampus (lower panels) from 8 week induced p25 Tg mice compared to WT mice. Insets represent higher magnification views. (H) Increased active caspase-3 immunohistochemical staining in coronal sections of the cerebral cortex from 8 week induced p25 Tg mice compared to WT mice. (I) Immunohistochemical staining of active caspase-3 staining in coronal sections of the dentate gyrus of the hippocampus from WT and 8 week induced p25 Tg mice. An adjacent Tg brain section was also immunostained with anti-GFP. (J) Increased GFAP and active caspase-3 immunoreactivity in p25 Tg brain regions highly expressing p25. Immunoblot analysis was performed on WT and 7 week induced Tg mice using p35, GFAP, and active caspase-3 antibodies.

Figure 28:
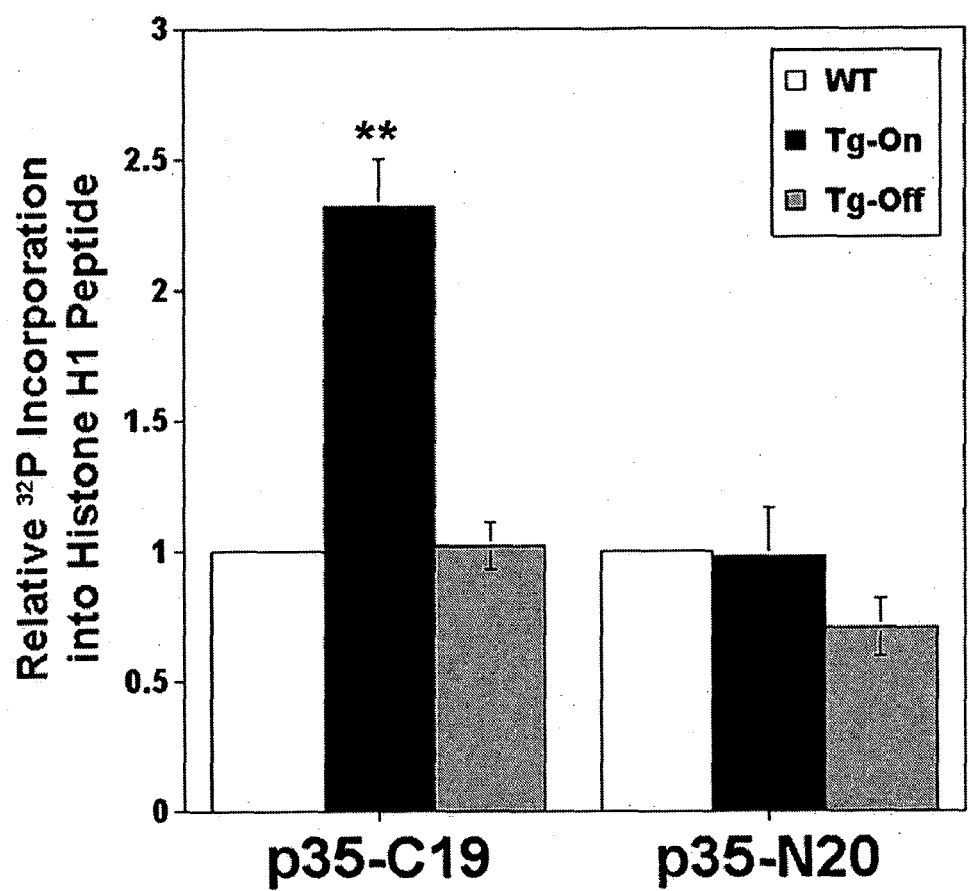
Figure 28:
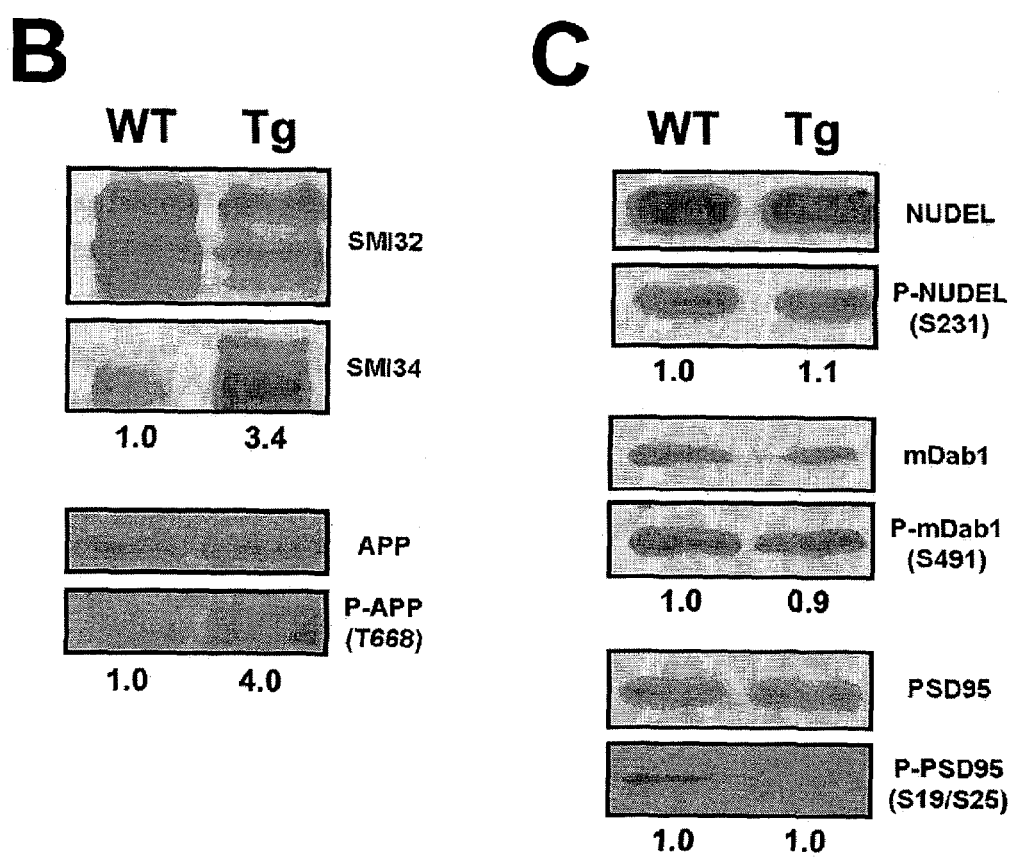

FIGS. 28A-28C depict Cdk5 activity and differential Cdk5 substrate phosphorylation. (A) Increased Cdk5 activity in p25 Tg mice. Immunoprecipitation kinase assays were conducted to measure Cdk5 activity in WT, Tg-On, and Tg-Off mice. Values for Tg-On and Tg-Off mice were calculated relative to WT control littermates. Error bars represent standard error of the mean (SEM) values for WT (n=4), Tg-On (n=4) and Tg-Off (n=3) Tg mice. P values (**p<0.005) were determined using a two-tailed, non-parametric, unpaired Student's T-test. (B and C) Increased phosphorylation of pathological, but not physiological, Cdk5 substrates in p25 Tg mice. Immunoblot analysis of WT and Tg mice was performed using antibodies and specific phospho-epitope antibodies to unphosphorylated neurofilament protein (NF) (SMI32) or phosphorylated NF (SMI34); APP or phospho-APP (T668); Nudel or phospho-Nudel (S231), mDab1 or phospho-mDab1 (S491), and PSD95 or phospho-PSD95 (S19/S25). The fold increase (relative to WT) represents the average of two or more independent experiments from at least two different pairs of WT and Tg littermates. Densitometry analysis was performed using the FujiFilm Science Lab Image Gauge software. In (A-C), forebrain lysates from Tg mice induced, or non-induced, for 5 weeks were analyzed.

FIGS. 29A-29F depict tau hyperphosphorylation. (A-C) Immunoblot analysis of 5-seven week forebrain lysates from WT and p25 Tg mice using tau and phospho-tau antibodies. Equal protein amounts were loaded as indicated by the similar Cdk5 levels found in all animals. Using the tau 5 antibody recognizing total tau, no apparent differences were observed (A). Using tau antibodies recognizing specific phospho-epitopes of tau, such as AT8 (S202/T205) (B) and PHF-1 (S396/S404) (C), significant increases in tau hyperphosphorylation were found in Tg mice. (D) Immunohistochemical phospho-tau staining of coronal brain sections from WT and 12 week induced p25 Tg mice. In Tg mice, an abundant number of neurons in the cerebral cortex were immunostained with PHF1 antibodies (upper panels) and in the CA2 region of the hippocampus with AT8 antibodies (lower panels). Insets represent higher magnification views. (E) Mass spectrometry analysis of heat stable tau preparations from WT and 5 week induced Tg forebrains. A partial protein sequence of the mouse tau protein shows the phosphorylated peptide coverage map. The numbering is based on human tau, which is 441 amino acids long. Tau phosphopeptides detected in mass spectrometry are shown in the following colors: green (WT), red (Tg), and blue (overlap of WT and Tg). Results shown are representative of two independent experiments. (F) Microtubule polymerization assay. Heat stable tau preparations derived from forebrains of Tg mice show a marked decrease over time in polymerizing tubulin to form stable microtubules as compared to WT mice. Results shown are representative of two independent experiments.

FIGS. 30A-30E depict sarkosyl-insoluble tau. (A) Accumulation of sarkosyl-insoluble tau in p25-GFP Tg mice. Sarkosyl-insoluble fractions were obtained from forebrain tissues of WT, Tg mice induced for 8 or 12 weeks. Immunoblot analysis was performed using tau 5 and AT8 antibodies. The * indicates the presence of a 68 kD tau isoform. (B) Accumulation of sarkosyl-insoluble tau in p25-C-myc Tg mice. Immunoblot analysis of sarkosyl-soluble and sarkosyl-insoluble fractions derived from forebrain tissues of WT and Tg mice induced for 15 weeks was performed using tau 5 antibodies. The * indicates the presence of a 68 kD tau isoform. (C) Accumulation of sarkosyl-insoluble tau in p25-GFP Tg mice. Immunoblot analysis, using tau 5 antibodies of sarkosyl-insoluble fractions derived from forebrains and hindbrains of WT and Tg mice induced for 27 weeks, was performed. Lysates were also treated with phosphatase for 1 h at 37° C. and subjected to immunoblot analysis using tau 1 antibodies, recognizing unphosphorylated tau. (D and E) Immunoelectron microscopy of sarkosyl-insoluble fractions from p25 and tau P301L Tg mice. Sarkosyl-insoluble fractions from (B) or from forebrains of 1 year old tau P301L Tg mice were similarly decorated with antibodies tau 5 and 5E2 antibodies, recognizing unphosphorylated and phosphorylated tau (D), and AT8, PHF1, and TG3 antibodies, recognizing phospho-tau epitopes S202/T205, S396/S404, and an abnormal hyperphosphorylated confirmation state of tau, respectively (E).

FIGS. 31A-31I depict NFT pathology. (A-E) Gallyas silver and (F-I) Thioflavin-S staining of WT and p25 Tg mice. Numerous Gallyas silver and Thioflavin-S positive neurons were found in Tg mice, but not in WT mice, in the cerebral cortex and parietal cortex (B-C and G), entorhinal cortex (D and H), and hippocampus (E and I). Insets represent higher magnification views. No positive-stained neurons were found in any of these regions analyzed in WT mice (A and F). In (A-I), all Tg mice analyzed were induced for 27-30 weeks and compared to same-sex littermate WT mice.

Figure 32:
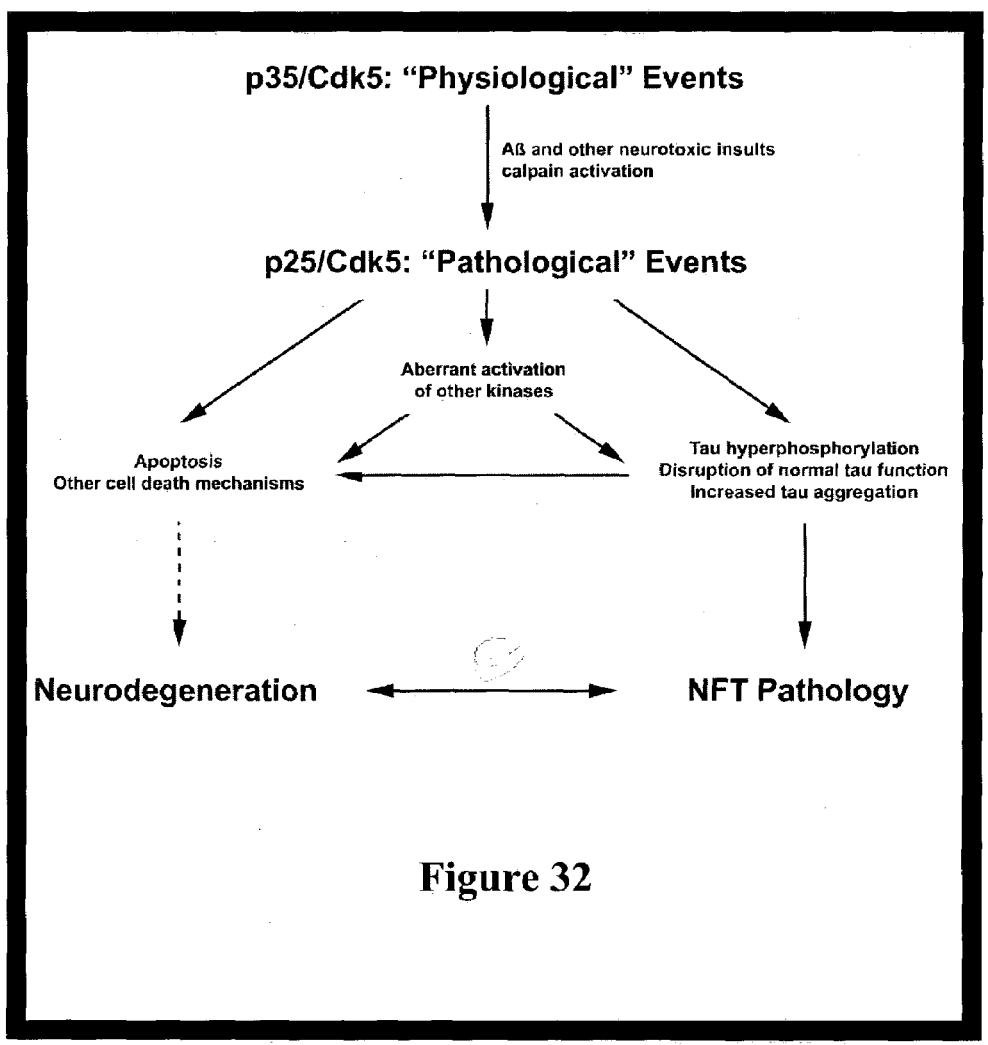

FIG. 32 depicts a model describing the various pathogenic events that are triggered by p25 and aberrant Cdk5 activity under neurotoxic conditions.

FIGS. 33A-33E depict a p25-C-myc Tg mouse line. (A) Forebrain expression of p25 transgene. Immunoblot analysis using p35 antibodies demonstrate very similar expression levels of the p25 transgene in p25-C-myc and the p25-GFP Tg mouse lines from forebrain extracts of WT and p25 Tg mice. Both sets of Tg mice were induced for 8 weeks. Cdk5 expression levels did not vary among the mice analyzed. (B) Immunoblot analysis using p35 antibodies from brain lysates derived from cortex (ctx), hippocampus (hip), and cerebellum (cer) of WT and p25-C-myc Tg mice induced for 6 weeks. (C) Decreased brain weight in p25-Cmyc Tg mice. Whole brains from WT and Tg mice induced for 8-12 weeks were dissected and weighed. Error bars represent SEM values for WT (n=5) and Tg mice (n=5). SEM value for Tg mice is ±0.004, which was too small to indicate on the bar graph. P value ($^{*}p<0.0001$) was determined using a two-tailed, non-parametric, unpaired Student's T-test. (D) Neuronal loss in p25-C-myc Tg mouse line was determined as described herein. P value ($^{}p<0.005$) was determined using a two-tailed, non-parametric, unpaired Student's T-test. (E) Tau phosphorylation in p25-C-myc Tg mouse line. Immunohistochemical staining, using phosphospecific AT8 antibodies recognizing S202/T205 of tau, in the cortex and hippocampus of Tg mice induced for 13 weeks. No somatodendritic localization of phosphorylated tau stainings were found in WT littermate control mice.

Figure 34:
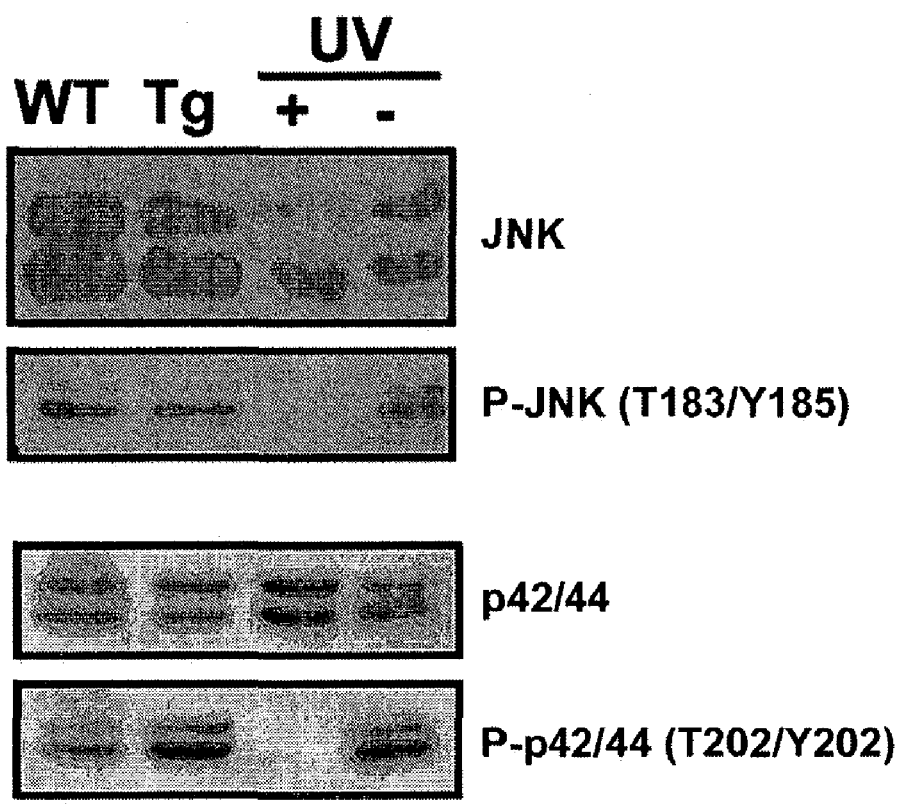
Figure 34:
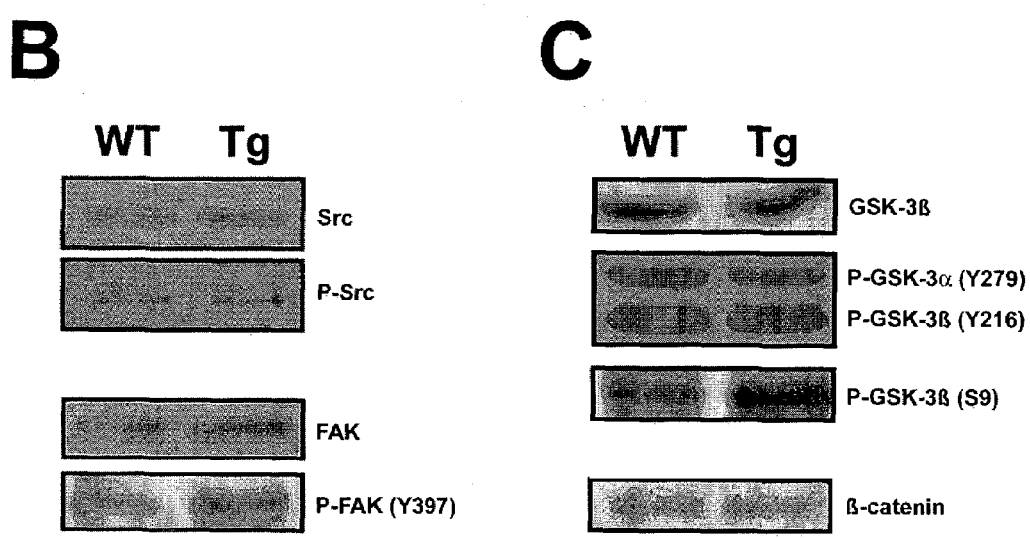

FIGS. 34A-34C depict the activation status of other kinases and signaling pathways. (A) Activation of the mitogen-activated protein kinase (MAPK) pathway but not the c-Jun N-terminal kinase (JNK) pathway. Immunoblot analysis of WT, Tg mice, or NIH 3T3 cells treated with or without ultraviolet (UV) light was performed using antibodies recognizing JNK or phospho-JNK (P-JNK) (T183/Y185) and p42/44 or phospho-p42/44 (T202/Y204). While no increase in activity of JNK pathway was observed, the activity of the p42/44 MAP kinases was found to be elevated in the Tg mice. (B) Activation of FAK but not Src kinase. Immunoblot analysis of WT and Tg mice was performed using antibodies recognizing Src or phospho-Src and FAK or phospho-FAK (Y397). With regards to non-receptor tyrosine kinases, while activity of the Src kinase did not differ between WT and Tg mice, focal adhesion kinase (FAK) was activated in Tg mice, as evidenced in increased FAK phosphorylation at Y397. (C) Glycogen synthase kinase (GSK)-3α and GSK-3β activity was not increased. Immunoblot analysis of WT and Tg mice was performed using antibodies recognizing GSK-3β, phospho-GSK-3α/GSK-3β (Y279/Y216) recognizing active kinases, and phospho-GSK-3β (S9) recognizing inactive kinase. In addition, immunoblot analysis of WT and Tg mice showed no changes in the level of β-catenin, a substrate of GSK-3β that is degraded upon GSK-3β phosphorylation. This indicates that GSK-3β activity was not upregulated in Tg mice. In (A-C), forebrain lysates from Tg mice induced, or non-induced, for 5 weeks were analyzed.

FIGS. 35A-35C depict upregulation of C99 in Tg mice. (A) Increased intraneuronal 4G8 immunostaining in the parietal cortex of p25 Tg mice. Coronal brain sections of WT and Tg mice induced for 8 weeks were stained with 4G8 antibodies, which recognize amino acids 17-24 of Aβ peptide. (B) Altered APP processing in p25 Tg mice. Western blot analysis of forebrain lysates from WT, Tg-On, and Tg-Off mice showed a significant increase in CTF of APP in Tg-On mice induced for 8 weeks. (C) Increase in APP-CTF is dependent upon progressive p25 induction. In Tg-On mice, the increase in CTF of APP was only observed after Tg mice had been induced for over 5 weeks. The identity of the CTF species was determined by molecular weight and dephosphorylation of the protein bands to the three major protein fragments, C83, C89, and C99.

DETAILED DESCRIPTION OF THE INVENTION

The present invention is directed in part to methods of therapeutically treating individuals afflicted with AD, methods of diagnosing AD, methods of inhibiting or reducing APP phosphorylation and methods of decreasing production of Aβ peptides. The present invention is further directed in part to Tg non-human animals and Tg cells expressing p25. These animals and cells exhibit properties associated with neurodegenerative disorders and serve as systems in which to study neurodegenerative disorders.

In one embodiment, the present invention provides a method of therapeutically treating an individual afflicted with AD comprising administering a compound which inhibits the ability of a kinase to phosphorylate and/or hyperphosphorylate APP, thereby inhibiting the progression of AD. The treatment also includes as an additional embodiment reducing symptoms associated with AD. In one aspect, the kinase can phosphorylate APP on one or more serine, threonine, and/or tyrosine residues. In another aspect, the kinase can phosphorylate one or more serine and/or threonine residues. In yet another aspect, the kinase phosphorylates threonine 668 of APP. In still another aspect, the kinase phosphorylates tyrosine 653, serine 655, serine 675, tyrosine 682, threonine 686 and/or tyrosine 687 of APP.

Many kinases families have been described in the art. Non-limiting examples of kinase families include the protein kinase A (PKA) family, the protein kinase C (PKC) family, the phosphoinositide-dependent kinase (PDK) family, the MAP kinase (MAPK) family, the choline kinase (CHK) family, the casein kinase II (CKII) family, the cyclin-dependent kinase (CDK) family, the pim kinase (PIM) family, the STKR kinase family, the NEK kinase family, the thymidine kinase (TK) family, the inositol kinase family and the like. A complete list of kinase families can be found at the Protein Kinase Resource website, incorporated herein by reference in its entirety (http://pkr.sdsc.edu/html/index.shtml). In one embodiment, the kinase is a cyclin-dependent kinase. In one embodiment kinases include, but are not limited to, Cdk1, Cdk2, Cdc2b, Cdk21, Cdk3, Cdk4, Cdk5 Cdk6, Cdk7, Cdk8KKIAMRE, p56, Mol5, STK1, p39, CCRK (cell cycle related kinase), MPF, M-phase kinase, PSK-J3, PSSALRE, TPKII, PLSTIRE, cdc2-related, KIAA0904, CHED, KKILARE, PCTAIRE1, PCTAIRE2, PCTAIRE3, PFTAIRE1, G20041, KIAA0834, PISSLRE, PK2J, CDK10, PITALRE, C-2K, CDK9, P-TEFβ kinase, PITSLREα2-1, PITSLREα2-2, PITSLREα2-3, PITSLREα2-4, PITSLREα2-a1, PITSLREα2-b, PBETA21, STK9, cyclin-dependent kinase C, B1-type cyclin-dependent kinase, B2-type cyclin-dependent kinase, cyclin-dependent kinase p34 and the like. In another embodiment kinases include Cdk5, Cdc2, SAPK1b/JNK3, and GSK3β.

In another aspect of the invention, compounds which inhibit one or more kinases are provided. In yet another embodiment, the present invention provides a method of modulating phosphorylation of APP in an individual comprising contacting an individual with a compound, wherein the compound inhibits the ability of a kinase to phosphorylate APP. In one aspect, the compound reduces or inhibits phosphorylation of APP. In another aspect, the compound reduces or inhibits hyperphosphorylation of APP. That is, the compound prevents APP from being phosphorylated at levels higher than those observed on APP from a subject not suffering from AD.

Compounds which inhibit one or more kinases include compounds which inhibit cyclin-dependent protein kinases such as purines and substituted purines, alkaloids, indirubins, flavonoids, paullones, butyrolactone, and hymenialdisine. Purines and substituted purines include butyrolactone, roscovitine, olomoucine, CVT-313, isopentyl-adenine, purvalanol B, 2,6,9-trisubstituted purine derivatives, and azapurine derivatives. Alkaloids include staurosporine, UCN-01, and CGP 41 251. Indirubins include indirubin, 5-chloro-indirubin, indirubin-3'-monoxime, and indirubin-5-sulphonic acid. Flavonoids include flavopiridol and phytoestrogenic flavonoid antioxidants (e.g., silibinin, sylymarin, and baicalein). Paullones include kenpaullone and alsterpaullone. In another embodiment, the kinase inhibitors are non-specific kinase inhibitors including, but not limited to, H-8 dihydrochloride, H-9 dihydrochloride, KN-62, K252a, K252b, and staurosporine. In another embodiment, the kinase inhibitor is an inhibitor of Cdk5. Accordingly, the present invention is directed to Cdk5 inhibitors including butyrolactone, roscovitine, olomoucine, kenpaullone, and alsterpaullone. In yet another embodiment, the kinase inhibitor specifically inhibits kinases from one or more of the families described herein.

In another aspect of the invention, compounds which induce endogenous kinase inhibitors (e.g., cyclin-dependent kinase inhibitors) are provided. In one embodiment, an endogenous cyclin-dependent kinase inhibitor is the Cdk5 inhibitor ribosomal protein L34.

In another aspect of the invention, compounds which inhibit endogenous kinase activators (e.g., cyclin-dependent kinase activators) are provided. In another embodiment, endogenous cyclin-dependent kinase activator is the Cdk5 activator p25 and its precursor protein p35. In another embodiment, an endogenous cyclin-dependent kinase activator is the protease m-calpain, which cleaves p35 to generate p25. In yet another embodiment, an endogenous activator is the activator of the protease calpain.

In one embodiment, the present invention provides methods whereby symptoms of AD are inhibited, reduced, prevented, and/or reversed. In another embodiment, the present invention provides methods whereby compounds that effect (i.e., modulate, inhibit, reduce, prevent or reverse) symptoms of AD are identified. As used herein, symptoms of AD are well known to those skilled in the art and include behavioral, physical, and pathological symptoms. Behavioral symptoms of AD include agitation, wandering, anxiety, suspicion, paranoia, the inability to cope with change, and depression. Physical symptoms of AD include cognitive defects such as dementia, impaired judgment, memory loss (e.g., a loss of short term memory and/or long term memory), aphasia, apraxia, loss of spatial ability, and a reduction in the ability to speak, read, and write. Other physical symptoms of AD include weight loss, shuffling gait, jerking limb movements, a propensity for falls, incontinence, tiredness, sleeplessness, wandering at night, tremors, rigidity, slowness of movement, loss of physical coordination, and loss of the ability to walk. Pathological symptoms of AD include amyloid plaques that deposit extracelluarly (amyloid plaques), NFTs, neuronal degeneration, neuronal death and the like. The aforementioned symptoms lead to further pathological symptoms including lesions in parts of the brain, such as the entorhinal cortex, hippocampus, amygdala and cerebral cortex.

Typically, the progression of AD is assayed by physical examinations wherein the nervous system is examined by checking reflexes, muscle tone, and movement. Psychiatric evaluations are used to assay cognitive markers such as visual memory. The appearance of the brain is assayed using imaging techniques such as computed tomography (CT) scans or magnetic resonance imaging (MRI). Positron emission tomography (PET) scans may be used to trace blood flow and metabolism in the brain, and single photon emission computed tomography (SPECT) can be used to measure blood flow. Magnetic resonance spectroscopy imaging (MRSI) can be used to observe markers in the brain in the absence of radioactivity.

The present invention provides novel methods to assay the presence of AD in individuals using biological markers, i.e., by determining the phosphorylation state of APP. In one embodiment, APP phosphorylation is determined by biochemical methods on biological samples.

Accordingly, in another embodiment, the present invention provides a method of diagnosing AD in an patient comprising obtaining a biological sample from a patient, obtaining a biological sample from an individual without AD, comparing the level of APP phosphorylation in the biological sample from the patient to the level of APP phosphorylation in the biological sample from an individual without AD. A diagnosis of AD is made when the biological sample from the patient (i.e., test level) has increased APP phosphorylation compared to APP phosphorylation in the biological sample from the individual without AD (i.e., control level). According to an alternate embodiment of the present invention, a database (such as a computer generated and/or stored database) of control levels (e.g., levels in samples taken from individuals at various stages of AD and/or levels in samples taken from individuals that do not have AD) is compared to the test level and a diagnosis is made based on the comparison. Methods of creating, storing and using databases are well known to those of skill in the art.

Methods of determining protein phosphorylation (e.g., tau hyperphosphorylation or APP phosphorylation) and kinase activity (e.g., Cdk5 activity) include biochemical assays such as phosphorylation assays, phosphatase assays, SDS-PAGE, immunoprecipitations, protein extraction, silver staining, Coomassie staining, Western blot analysis, peptide mapping, isoelectric focusing, chromatography, mass spectrometry and the like. Protein phosphorylation can be assayed using antibodies that recognize peptides with phosphorylated amino acid residues (e.g., phosphorylated serine, threonine, or tyrosine residues, described herein). Methods of determining phosphorylation are known in the art and are described in references such as Hardie, D. G. Protein Phosphorylation: A Practical Approach. 2d ed., Oxford University Press, 1999, and Sefton, B. M. and Hunter T. Protein Phosphorylation. 1st ed., Academic Press, 1998, incorporated herein in their entirety by reference.

The presence of an activity, phenotype or symptom associated with a neurodegenerative disorder (e.g., AD) may be identified from a biological sample taken from, for example, the Tg animals described herein. Biological samples may be of any biological tissue or fluid or cells. Frequently the sample will be a "clinical sample" which is a sample derived from a patient. Typical biological samples include, but are not limited to, sputum, blood, blood cells (e.g., white cells), tissue (e.g., brain tissue, spinal tissue) or fine needle biopsy samples, urine, cerebrospinal fluid, peritoneal fluid, and pleural fluid, or cells therefrom. Biological samples may also include sections of tissues such as frozen sections taken for histological purposes, for example from the brain or spine.

The Tg animals and cells of the present invention are useful for screening compounds that inhibit, reduce, prevent or reverse a symptom, an activity or a phenotype associated with neurodegenerative disorders. As used herein, the terms "inhibit," "inhibition," "reduce," "reduction," "prevent," "prevention," "reverse" and "reversal" refer to a partial inhibition, reduction, prevention or reversal or a complete inhibition, reduction, prevention or reversal of one or more phenotypes associated with a neurodegenerative disorder (e.g., AD) as described herein. These terms also refer to a partial inhibition, reduction, prevention or reversal or a complete inhibition, reduction, prevention or reversal of one or more activities of a protein or nucleic acid sequence (e.g., DNA or RNA expressing a protein) that is associated with a neurodegenerative disorder as described herein. These terms also refer to a partial inhibition, reduction, prevention or reversal or a complete inhibition, reduction, prevention or reversal of one or more symptom (e.g., behavioral, physical or pathological) that is associated with a neurodegenerative disorder as described herein.

For example, and not by means of limitation, a protein associated with a neurodegenerative disorder is p25. An inhibition of p25 can occur, for example, when a Tg animal or Tg cell expressing p25 has a higher level of a p25 activity, phenotype or symptom (e.g., a higher level of aberrant activation of Cdk5, tau hyperphosphorylation, APP phosphorylation, APP hyperphosphorylation, C99 upregulation, tau aggregation, progressive neuronal loss, neurofibrillary tangle formation, and the like) than a Tg animal or Tg cell contacted with a compound that inhibits a p25 activity, phenotype or symptom. A complete inhibition can occur, for example, when the p25 activity, phenotype or symptom is not observed in a Tg animal or in Tg cell expressing p25 exposed to a compound that inhibits a p25 activity, phenotype or symptom. A partial inhibition can occur, for example, when a p25 activity, phenotype or symptom is higher in a Tg animal or a Tg cell than in a Tg animal or Tg cell exposed to a compound that partially inhibits a p25 activity, phenotype or symptom. For example, a p25 activity, phenotype or symptom may be reduced to 99%, 95%, 90%, 85%, 80%, 75%, 70%, 65%, 60%, 55%, 50%, 45%, 40%, 35%, 30%, 25%, 20%, 15%, 10%, 5%, or 1% of the level of p25 activity in the absence of the compound.

In another embodiment, the present invention provides methods whereby compounds that modulate (i.e., inhibit, reduce, prevent or reverse) tau aggregation and symptoms of tauopathies are identified. As used herein, the terms "tauopathy" and "tauopathies" refer to dementias and movement disorders that share the pathological feature of intracellular accumulations of tau. Examples of tauopathies include, but are not limited to, Down's syndrome, corticobasal degeneration, frontotemporal dementia, Pick's disease, and progressive supranuclear palsy.

Diagnostic Assays

An exemplary method for detecting phosphorylation (e.g., tau phosphorylation, APP phosphorylation and the like) in a biological sample involves obtaining a biological sample from a test subject and contacting the biological sample with a compound or an agent capable of detecting phosphorylated peptide such that the presence of phosphorylated peptide is detected in the biological sample. As used herein, the term "peptide" refers to polypeptides comprising two or more amino acid residues, full length protein sequences, fragments of protein sequences and the like. In one aspect, an agent for detecting phosphorylated peptide is an antibody capable of binding to the peptide (e.g., binding to APP), such as an antibody with a detectable label. In one aspect, the antibody only binds to hyperphosphorylated APP and/or APP phosphorylated at threonine 668. Antibodies which bind only to phosphorylated APP are described herein. Antibodies can be polyclonal, or in another aspect, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect phosphorylated peptide (e.g., APP) in a biological sample in vitro as well as in vivo. For example, in vitro techniques for detection of phosphorylated APP include enzyme linked immunosorbent assays (ELISAs), Western blots, immunoprecipitations and immunofluorescence. In vitro techniques for detection of phosphorylated APP include introducing into a subject a labeled anti-APP antibody. For example, the antibody can be labeled with a radioactive marker whose presence and location in a subject can be detected by standard imaging techniques.

In another embodiment, the methods of the invention further involve obtaining a control biological sample from a control subject, contacting the control sample with a compound or agent capable of detecting phosphorylated peptide (e.g., APP), such that the presence of phosphorylated peptide is detected in the biological sample, and comparing the peptide phosphorylation in the control sample with the presence of increased peptide phosphorylation in the test sample. As described herein, one or more database can also be used as the control.

The invention also includes kits for detecting the presence of phosphorylated peptide (i.e., APP) in a biological sample. For example, and not by way of limitation, the kit can include a compound or agent capable of detecting a phosphorylated peptide in a biological sample and a standard. The compound or agent can be packaged in a suitable container. The kit can further comprise instructions for using the kit to detect a phosphorylated peptide.

For antibody-based kits, the kit can include: (1) a first antibody (e.g., attached to a solid support) which binds to a phosphorylated polypeptide (i.e., APP); and, optionally, (2) a second, different antibody which binds to either the phosphorylated polypeptide or the first antibody and is conjugated to a detectable agent.

Prognostic Assays

The diagnostic methods described herein can furthermore be utilized to identify subjects having or at risk of developing a neurodegenerative disorder such as AD, for example, by determining the presence of increased peptide (i.e., APP) phosphorylation. As used herein, the term "increased" includes peptide phosphorylation which is increased relative to the WT peptide phosphorylation indicative of an individual not suffering from a neurodegenerative disorder such as AD (i.e., a healthy individual) or suffering from various stages of AD. Increased APP phosphorylation includes hyperphosphorylation and/or phosphorylation of threonine 668 of APP, as well as phosphorylated APP expression or activity which does not follow the WT developmental pattern of expression or the subcellular pattern of expression.

The assays described herein, such as the preceding diagnostic and prognostic assays or the following assays, can be utilized to identify a subject having or at risk of developing a neurodegenerative disorder (such as AD) associated with a misregulation of APP phosphorylation. Thus, the present invention provides a method for identifying AD in which a test sample is obtained from a subject and APP phosphorylation levels are detected, wherein the presence of an increase in APP phosphorylation is diagnostic for a subject having or at risk of developing AD. As used herein, a "test sample" refers to a biological sample obtained from a subject of interest. For example, a test sample can be a biological fluid (e.g., cerebrospinal fluid, serum), cell sample, or tissue (e.g., brain or spinal tissue).

Furthermore, the prognostic assays described herein can be used to determine whether a subject can be administered an agent (e.g., an agonist, antagonist, peptidomimetic, protein, peptide, nucleic acid, small molecule, or other drug candidate) to treat AD. Thus, the present invention provides methods for determining whether a subject can be effectively treated with an agent for AD associated with increased APP phosphorylation in which a test sample is obtained and APP phosphorylation is detected.

Monitoring of Effects during Clinical Trials

Monitoring the influence of agents (e.g., compounds which inhibit kinases) on the modulation of APP phosphorylation can be applied not only in basic drug screening, but also in clinical trials.

For example, the effectiveness of an agent determined by a screening assay as described herein to decrease APP phosphorylation, can be monitored in clinical trials of subjects exhibiting increased APP phosphorylation. In such clinical trials, phosphorylation patterns of APP that have been implicated in AD can be used as a "read out."

For example, and not by way of limitation, APP phosphorylation that is decreased in cells by treatment with an agent (e.g., compound, drug or small molecule) which decreases APP phosphorylation (e.g., identified in a screening assay as described herein) can be identified. Thus, to study the effect of agents on AD, for example, in a clinical trial, cells can be isolated and protein prepared and analyzed for the levels of APP phosphorylation. The levels of APP phosphorylation are analyzed by measuring the amount of phosphorylation by one of the methods as described herein. In this way, the phosphorylation pattern can serve as a marker, indicative of the physiological response of the cells to the agent. Accordingly, this response state may be determined before, and at various points during treatment of the individual with the agent. Other useful markers of neurodegenerative disorders are described further herein.

In one embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of APP phosphorylation in the preadministration sample; (iii) obtaining one or more post-administration samples from the subject; (iv) detecting the level of APP phosphorylation in the post-administration samples; (v) comparing the level of APP phosphorylation in the pre-administration sample with the APP phosphorylation in the post administration sample or samples; and (vi) altering the administration of the agent to the subject accordingly. For example, increased administration of the agent may be desirable to decrease APP phosphorylation to lower levels than detected, i.e., to increase the effectiveness of the agent. Alternatively, decreased administration of the agent may be desirable to increase APP phosphorylation to higher levels than detected, i.e., to decrease the effectiveness of the agent. According to such an embodiment, APP phosphorylation may be used as an indi-

Antibodies

In one embodiment, antibodies are provided against peptides such as APP. For example, an APP immunogen can be used to prepare such antibodies by immunizing a suitable subject, (e.g., rabbit, goat, mouse or other mammal) with the immunogen. An appropriate immunogenic preparation can contain, for example, recombinantly expressed APP or a chemically synthesized APP polypeptide. The preparation can further contain recombinantly expressed APP or a chemically synthesized APP polypeptide which is phosphorylated. The preparation can further include an adjuvant, such as Freund's complete or incomplete adjuvant, or similar immunostimulatory agent. Immunization of a suitable subject with an immunogenic APP preparation induces a polyclonal anti-APP antibody response.

Accordingly, another aspect of the invention pertains to antibodies such as anti-APP antibodies. The term "antibody," as used herein, refers to immunoglobulin molecules and immunologically active portions of immunoglobulin molecules, i.e., molecules that contain an antigen binding site which specifically binds (immunoreacts with) an antigen, such as APP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind peptides such as APP. The term "monoclonal antibody" or "monoclonal antibody composition," as used herein, refers to a population of antibody molecules that contain only one species of an antigen binding site capable of immunoreacting with a particular epitope of APP, for example, such as phosphorylated APP. A monoclonal antibody composition thus typically displays a single binding affinity for a particular APP protein with which it immunoreacts.

Polyclonal anti-APP antibodies, for example, can be prepared as described above by immunizing a suitable subject with an APP immunogen, preferably a phosphorylated APP immunogen. The anti-APP antibody titer in the immunized subject can be monitored over time by standard techniques, such as with an enzyme linked immunosorbent assay (ELISA) using immobilized APP. If desired, the antibody molecules directed against APP can be isolated from the mammal (e.g., from the blood) and further purified by well known techniques, such as protein A chromatography to obtain the IgG fraction. At an appropriate time after immunization, e.g., when the anti-APP antibody titers are highest, antibody-producing cells can be obtained from the subject and used to prepare monoclonal antibodies by standard techniques, such as the hybridoma technique originally described by Kohler and Milstein ((1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985), Monoclonal Antibodies and Cancer Therapy, Alan R. Liss, Inc., pp. 77-96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) *J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with an APP immunogen as described above, and the culture supernatants of the resulting hybridoma cells are screened to identify a hybridoma producing a monoclonal antibody that binds APP.

Any of the many well known protocols used for fusing lymphocytes and immortalized cell lines can be applied for the purpose of generating an anti-APP monoclonal antibody (see, e.g., G. Galfre et al. (1977) *Nature* 266:55052; Gefter et al. Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. In one aspect, immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind APP, e.g., using a standard ELISA assay.

Alternative to preparing monoclonal antibody-secreting hybridomas, a monoclonal anti-APP antibody can be identified and isolated, for example, by screening a recombinant combinatorial immunoglobulin library (e.g., an antibody phage display library) with APP to thereby isolate immunoglobulin library members that bind APP. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370-1372; Hay et al. (1992) Hum. Antibod. Hybridomas 3:81-85; Huse et al. (1989) *Science* 246:1275-1281; Griffiths et al. (1993) *EMBO* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991)

*Proc. Natl. Acad. Sci. USA* 88:7978-7982; and McCafferty et al. *Nature* (1990) 348:552-554.

Additionally, recombinant antibodies, such as chimeric and humanized monoclonal anti-APP antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173, 494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-APP antibody (e.g., monoclonal antibody) can be used to isolate APP by standard techniques, such as affinity chromatography or immunoprecipitation. An anti-APP antibody can facilitate the purification of natural APP from cells and of recombinantly produced APP expressed in host cells. Moreover, an anti-APP antibody can be used to detect APP protein (e.g., in a cellular lysate or cell supernatant) in order to evaluate APP phosphorylation. Furthermore, an anti-APP antibody can be used to detect phosphorylated APP protein. Anti-APP antibodies can be used diagnostically to monitor APP phosphorylation levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include Streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{32}$P, $^{125}$I, $^{131}$I, $^{35}$S or $^{3}$H.

Pharmaceutical Compositions

Methods of administering a compound to an individual include providing pharmaceutically acceptable compositions. In one embodiment, pharmaceutically acceptable compositions comprise a therapeutically effective amount of one or more of the compounds described above, formulated together with one or more pharmaceutically acceptable carriers (additives) and/or diluents. Generally, the active agents need to pass the blood brain barrier and may have to be chemically modified, e.g., made hydrophobic, to facilitate this or be administered directly to the brain or via other suitable routes. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In another embodiment, the therapeutic compound is administered orally. The compounds of the invention can be formulated as pharmaceutical compositions for administration to a subject, e.g., a mammal, including a mouse or a human.

The compounds of the invention are administered to subjects in a biologically compatible form suitable for pharmaceutical administration in vivo. By "biologically compatible form suitable for administration in vivo" is meant a compound to be administered in which any toxic effects are outweighed by the therapeutic effects of the compound. The term subject is intended to include living organisms such as mammals. Examples of subjects include humans, dogs, cats, mice (e.g., p25 Tg mice, APP(Sw) mice and the like), rats, and Tg species thereof. Administration of a therapeutically active amount of the therapeutic compositions of the present invention is defined as an amount effective, at dosages and for periods of time necessary to achieve the desired result. For example, a therapeutically active amount of a compound of the invention may vary according to factors such as the disease state, age, sex, and weight of the individual, and the ability of antibody to elicit a desired response in the individual. Dosage regimes may be adjusted to provide the optimum therapeutic response. For example, several divided doses may be administered daily or the dose may be proportionally reduced as indicated by the exigencies of the therapeutic situation.

As defined herein, a therapeutically effective amount of agent (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, preferably, can include a series of treatments. It will also be appreciated that the effective dosage of in used for treatment may increase or decrease over the course of a particular treatment. Changes in dosage may result from the results of diagnostic assays as described herein.

The active compound may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

A compound of the invention can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer a compound of the invention by other than parenteral administration, it may be necessary to coat the compound with, or co-administer the compound with a material to prevent its inactivation. Liposomes include water-in-oil-in-water emulsions as well as conventional liposomes (Strejan et al., (1984) *J. Neuroimmunol.* 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

Tg Animals

The present invention provides non-human, Tg animals. In one embodiment, the nonhuman, Tg animals of the invention are produced from a fertilized oocyte or an embryonic stem cell into which p25 coding sequences have been introduced. Such host cells can then be used to create non-human Tg animals in which exogenous p25 sequences have been introduced into their genome. As used herein, a "Tg animal" is a non-human animal, such a mammal, or a rodent such as a rat or mouse, in which one or more of the cells of the animal includes one or more transgenes. Other examples of Tg animals include non-human primates, sheep, dogs, cows, goats, chickens, amphibians and the like. As used herein, a transgene is exogenous DNA which is integrated into the genome of a cell from which a Tg animal develops and which remains in the genome of the mature animal, thereby directing the expression of an encoded gene product in one or more cell types or tissues of the Tg animal.

A Tg animal of the invention can be created by introducing a p25-encoding nucleic acid into the male pronuclei of a fertilized oocyte, e.g., by microinjection or retroviral infection, and allowing the oocyte to develop in a pseudopregnant female foster animal. Intronic sequences and polyadenylation signals can also be included in the transgene to increase the efficiency of expression of the transgene. Methods for generating Tg animals via embryo manipulation and microinjection, particularly animals such as mice, have become conventional in the art and are described, for example, in U.S. Pat. No. 4,736,866 by Leder et al. and U.S. Pat. No. 4,870,009 Evans et al., U.S. Pat. No. 4,873,191 by Wagner et al., and in Hogan, B., Manipulating the Mouse Embryo, (Cold Spring Harbor Laboratory Press, Cold Spring Harbor, N.Y., 1986), incorporated herein by reference in their entirety. Similar methods are used for production of other Tg animals. A Tg founder animal can be identified based upon the presence of a detectable translation product transgene in its genome and/or expression of detectable translation product mRNA in tissues or cells of the animals. A Tg founder animal can then be used to breed additional animals carrying the transgene. Moreover, Tg animals carrying a transgene encoding a detectable translation product can further be bred to other Tg animals carrying other transgenes.

In another embodiment, the present invention provides Tg non-human animals which contain selected systems that allow for regulated expression of the transgene. Such regulation allows for exquisite control of gene expression and is particularly beneficial, for example, when the gene of interest may be toxic to the animal. One example of such a system is a tetracycline-off (Tet-Off) gene expression system. This system requires animals containing a transgene encoding the tetracycline-responsive transcriptional activator (tTA) (commercially available from BD Biosciences)

and a transgene encoding Tet Response Element (TRE) operably linked to a gene of interest, i.e., a p25 gene. In this system, tTA binds to the TRE and activates transcription of the gene of interest in the absence of inducer (e.g., doxycycline or tetracycline). Such animals can be provided through the construction of "double" Tg or "bitransgenic" animals, e.g., by mating two Tg animals, one containing a transgene encoding the TRE operably linked to the gene of interest, and the other containing a transgene encoding tTA.

In one aspect, gene expression in the Tg non-human animals is limited to specific organs, tissues or cells of the Tg non-human animal. One example of such regulation is achieved placing the vector encoding tTA under the control of a calcium-calmodulin-dependent kinase II (CamKII) promoter, which directs expression of the gene under its control to the forebrain (see Mayford et al. (1996) Science 274: 5293, incorporated by reference herein in its entirety). In this manner, expression of the gene of interest (i.e., p25) occurs only in the forebrain.

Clones of the non-human Tg animals described herein can also be produced according to the methods described in Wilmut et al. (1997) Nature 385:810. In brief, a cell, e.g., a somatic cell, from the Tg animal can be isolated and induced to exit the growth cycle and enter $G_0$ phase. Alternatively, a cell, e.g., an embryonic stem cell, from the inner cell mass of a developing embryo can be transformed with a preferred transgene. Alternatively, a cell, e.g., a somatic cell, from cell culture line can be transformed with a preferred transgene and induced to exit the growth cycle and enter $G_0$ phase. The cell can then be fused, e.g., through the use of electrical pulses, to an enucleated mammalian oocyte. The reconstructed oocyte is then cultured such that it develops to morula or blastocyst and then transferred to pseudopregnant female foster animal. The offspring borne of this female foster animal will be a clone of the animal from which the nuclear donor cell, e.g., the somatic cell, is isolated.

One aspect of the invention pertains to isolating cells from the non-human Tg animals of the invention and growing the cells in culture. Another aspect of the invention pertains to host cells into which a recombinant expression vector of the invention has been introduced, containing sequences which allow it to homologously recombine into a specific site of the host cell's genome, or sequences that allow it to randomly or semi-randomly recombine into the host cell's genome. It is understood that such cells refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Recombinant Expression Vectors and Host Cells

Another aspect of the invention pertains to vectors, preferably expression vectors, optionally containing a nucleic acid encoding a p25 (or a portion thereof) or tTA. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences such as CaMKII). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., p25 proteins, mutant forms of p25 proteins, fusion proteins, and the like).

The recombinant expression vectors of the invention can be designed for expression of, for example, p25 in prokaryotic or eukaryotic cells. For example, p25 or p25 fragments can be expressed in bacterial cells such as *E. coli*, insect cells (using baculovirus expression vectors), yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

In one embodiment, a peptide such as p25 is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187). When used in mammalian cells, the expression vector's control functions are often provided by viral regulatory elements. For example, commonly used promoters are derived from polyoma, adenovirus 2, cytomegalovirus and Simian virus 40. For other suitable expression systems for both prokaryotic and eukaryotic cells see chapters 16 and 17 of Sambrook, J., Fritsh, E. F., and Maniatis, T. Molecular Cloning:

A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the CaMKII promoter (Mayford et al. (1996) *Science* 274:5293), the albumin promoter (liver-specific; Pinkert et al. (1987) *Genes Dev.* 1:268), lymphoid-specific promoters (Calame and Eaton (1988) *Adv. Immunol.* 43:235), in particular promoters of T cell receptors (Winoto and Baltimore (1989) *EMBO J.* 8:729) and immunoglobulins (Banerji et al. (1983) *Cell* 33:729; Queen and Baltimore (1983) *Cell* 33:741), neuron-specific promoters (e.g., the neurofilament promoter; Byrne and Ruddle (1989) *Proc. Natl. Acad. Sci. U.S.A.* 86:5473), pancreas-specific promoters (Edlund et al. (1985) *Science* 230:912), and mammary gland-specific promoters (e.g., milk whey promoter; U.S. Pat. No. 4,873,316 and European Application Publication No. 264,166). Developmentally regulated promoters are also encompassed, for example the murine hox promoters (Kessel and Gruss (1990) *Science* 249:374) and the α-fetoprotein promoter (Campes and Tilghman (1989) *Genes Dev.* 3:537).

A host cell can be any prokaryotic or eukaryotic cell. For example, host cells can be bacterial cells such as *E. coli*, insect cells, yeast, *Xenopus* cells, or mammalian cells (such as Chinese hamster ovary cells (CHO), African green monkey kidney cells (COS), or fetal human cells (293T)). Other suitable host cells are known to those skilled in the art. In one aspect of the invention, a host cell is derived from the Tg non-human animals described herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a detectable translation product or can be introduced on a separate vector. Cells stably transfected with the introduced nucleic acid can be identified by drug selection (e.g., cells that have incorporated the selectable marker gene will survive, while the other cells die).

Screening Assays

The invention provides methods (also referred to herein as "screening assays") for identifying modulators, i.e., candidate or test compounds or agents (e.g., peptides, cyclic peptides, peptidomimetics, small molecules, small organic molecules, or other drugs) which effect (i.e., modulate, inhibit, reduce, prevent or reverse) symptoms associated with neurodegenerative disorders such as AD.

This invention further pertains to novel agents identified by the above-described screening assays. Accordingly, it is within the scope of this invention to further use an agent identified as described herein in an appropriate animal model as described herein. For example, a test compound or agent identified as described herein can be used in an animal model (e.g., a Tg p25 non-human animal) to determine the efficacy, toxicity, or side effects of treatment with such an agent. Alternatively, an agent identified as described herein can be used in an animal model to determine the mechanism of action of such an agent.

In one embodiment, an assay includes a Tg p25 animal-based assay as described herein. The Tg animal is contacted with a test compound and the ability of the test compound to modulate an activity or a phenotype associated with a neurodegenerative disorder is determined. In another embodiment, an assay is a cell-based assay in which a cell that expresses Tg p25 is contacted with a test compound and the ability of the test compound to modulate an activity or a phenotype associated with a neurodegenerative disorder is determined. Determining the ability of the test compound to modulate a neurodegenerative disorder can be accomplished by monitoring, for example, activities associated with neurodegenerative disorders such as abnormal phosphorylation patterns (e.g., of tau or APP), abnormal cleavage patterns (e.g., of APP) and the like. Determining the ability of the test compound to modulate a neurodegenerative disorder can also be accomplished by monitoring, for example, abnormal phenotypes or symptoms including, but not limited to, an increase in tau phosphorylation, tau hyperphosphorylation, an increase in APP phosphorylation, APP hyperphosphorylation, an increase in C99 levels, an increase in Aβ levels, Cdk5 dysregulation, caspase-3 activation, the presence of reactive astrogliosis, progressive neurodegeneration, the presence of aggregated tau fibrils, the formation of neurofibrillary tangles (NFTs), amyloid plaques, neuronal loss (e.g., in the cerebral cortex, hippocampus), brain atrophy and the like.

Determining the ability of the test compound to modulate the ability of a target molecule to bind to a substrate can be accomplished, for example, by coupling the target molecule with a radioisotope or enzymatic label such that binding of the target molecule substrate to the target molecule can be determined by detecting the labeled target molecule substrate in a complex. For example, compounds (e.g., target molecule substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

A non-limiting example of a target molecule substrate is a Cdk5 substrate. Cdk5 substrates include, but are not limited to, NFH, NFM, tau, Map1b, Nudel, Pak1, src, Cables, β-catenin, P/Q type Ca++ channel, NR2A, PSD95, Synapsin-1, Amphiphysin-1, Munc-18, DARPP-32, β-APP, presenilin, Dynamin1, pRb, ErbB, JNK3, PP1 inhibitor, MEF2C, FAK and the like.

It is also within the scope of this invention to determine the ability of a compound to interact with a target molecule without the labeling of any of the interactants. For example, a microphysiometer can be used to detect the interaction of a compound with target molecule without the labeling of either the compound or target (McConnell, H. M. et al. (1992) *Science* 257:1906). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and p25.

In another embodiment, an assay is a cell-based assay comprising contacting a Tg cell expressing p25 with a test compound and determining the ability of the test compound to modulate a neurodegenerative disorder. As used herein, "contacting a Tg cell" includes methods such as introducing the test compound into the cell using the methods described herein (e.g., electroporation, transfection and the like), expressing the test compound in the cell, contacting the cell membrane with the compound and the like. Upon contacting the membrane, the compound may be internalized by the cell, it may remain bound to the membrane, or it may dissociate from the membrane. Determining the ability of the test compound to modulate a neurodegenerative disorder can be accomplished, for example, by assaying physical and pathological characteristics as described herein.

Determining the ability of a test compound to bind to or interact with a target molecule can be accomplished by one of the methods described above for determining direct binding. In a preferred embodiment, determining the ability of a test compound to bind to or interact with a target molecule can be accomplished by determining the activity of the target molecule. For example, the activity of the target molecule can be determined by detecting induction of a cellular second messenger of the target, detecting catalytic/enzymatic activity of the target with an appropriate substrate, detecting the induction of a reporter gene (comprising a target-responsive regulatory element operatively linked to a nucleic acid encoding a detectable marker), or detecting a target-regulated cellular response.

In one aspect of the invention, a modulator of a neurodegenerative disorder is a compound which inhibits or reduces one or more kinases. In yet another aspect of the invention, a modulator of a neurodegenerative disorder is a compound which inhibits or reduces phosphorylation of APP or tau. In another aspect, the compound reduces or inhibits hyperphosphorylation of APP or tau. In still another aspect, the compound reduces the formation of Aβ or C99 or APP cleavage.

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412), or on beads (Lam (1991) *Nature* 354:82), chips (Fodor (1993) *Nature* 364:555), bacteria (Ladner, U.S. Pat. No. 5,223,409), spores (Ladner, U.S. Pat. No. 5,223,409), plasmids (Cull et al. (1992) *Proc. Natl. Acad. Sci. USA* 89:1865) or on phage (Scott and Smith (1990) *Science* 249:386); (Devlin (1990) *Science* 249:404); (Cwirla et al. (1990) *Proc. Natl. Acad. Sci. USA* 87:6378); (Felici (1991) *J. Mol. Biol.* 222:301); (Ladner supra).

Examples of methods for introducing a molecular library of randomized nucleic acids into a population of cells can be found in the art, for example in U.S. Pat. No. 6,365,344, incorporated herein in its entirety by reference. A molecular library of randomized nucleic acids can provide for the direct selection of candidate or test compounds with desired phenotypic effects. The general method can involve, for instance, expressing a molecular library of randomized nucleic acids in a plurality of cells, each of the nucleic acids comprising a different nucleotide sequence, screening for a cell exhibiting a changed physiology in response to the presence in the cell of a candidate or test compound, and detecting and isolating the cell and/or candidate or test compound.

In one embodiment, the introduced nucleic acids are randomized and expressed in the cells as a library of isolated randomized expression products, which may be nucleic acids, such as mRNA, antisense RNA, siRNA, ribozyme components, etc., or peptides (e.g., cyclic peptides). The library should provide a sufficiently structurally diverse population of randomized expression products to effect a probabilistically sufficient range of cellular responses to provide one or more cells exhibiting a desired response. Generally at least $10^6$, preferably at least $10^7$ more preferably at least $10^8$ and most preferably at least $10^9$ different expression products are simultaneously analyzed in the subject methods. Preferred methods maximize library size and diversity.

The introduced nucleic acids and resultant expression products are randomized, meaning that each nucleic acid and peptide consists of essentially random nucleotides and amino acids, respectively. The library may be fully random or biased, e.g. in nucleotide/residue frequency generally or per position. In other embodiments, the nucleotides or residues are randomized within a defined class, e.g. of hydrophobic amino acids, of purines, etc. In any event, where the ultimate expression product is a nucleic acid, at least 10, preferably at least 12, more preferably at least 15, most preferably at least 21 nucleotide positions need to be randomized; more if the randomization is less than perfect. Similarly, at least 5, preferably at least 6, more preferably at least 7 amino acid positions need to be randomized; again, more if the randomization is less than perfect.

Functional and structural isolation of the randomized expression products may be accomplished by providing free (not covalently coupled) expression product, though in some situations, the expression product may be coupled to a functional group or fusion partner, preferably a heterologous (to the host cell) or synthetic (not native to any cell) functional group or fusion partner. Exemplary groups or partners include, but are not limited to, signal sequences capable of constitutively localizing the expression product to a predetermined subcellular locale such as the Golgi, endoplasmic reticulum, nucleoli, nucleus, nuclear membrane, mitochondria, chloroplast, secretory vesicles, lysosome, and the like; binding sequences capable of binding the expression product to a predetermined protein while retaining bioactivity of the expression product; sequences signaling selective degradation, of itself or co-bound proteins; and secretory and membrane-anchoring signals.

It may also be desirable to provide a partner which conformationally restricts the randomized expression product to more specifically define the number of structural conformations available to the cell. For example, such a partner may be a synthetic presentation structure: an artificial polypeptide capable of intracellularly presenting a randomized peptide as a conformation-restricted domain. Generally such presentation structures comprise a first portion joined to the N-terminal end of the randomized peptide, and a second portion joined to the C-terminal end of the peptide. Preferred presentation structures maximize accessibility to the peptide by presenting it on an exterior loop, for example of coiled-coils, (Myszka, D. G., and Chaiken, I. M. Design and characterization of an intramolecular antiparallel coiled coil peptide. Biochemistry. 1994. 33:2362-2372). To increase the functional isolation of the randomized expression product, the presentation structures are selected or designed to have minimal biological activity as expressed in the target cell. In addition, the presentation structures may be modified, randomized, and/or matured to alter the presentation orientation of the randomized expression product. For example, determinants at the base of the loop may be modified to slightly modify the internal loop peptide tertiary structure, while maintaining the absolute amino acid identity. Other presentation structures include zinc-finger domains, loops on beta-sheet turns and coiled-coil stem structures in which non-critical residues are randomized; loop structures held together by cysteine bridges, cyclic peptides, etc.

In another embodiment, the present invention provides cyclic peptides for use in the libraries described herein. As used herein, the term "cyclic peptide" refers to a peptide configured in a loop. Cyclic peptides can be produced by generating a nucleotide sequence encoding a peptide to be cyclized flanked on one end with a nucleotide sequence encoding the carboxy-terminal portion of a split (or trans) intein (C-intein or $I_C$) and on the other end with a nucleotide sequence encoding the amino-terminal portion of a split intein (N-intein or $I_N$). Expression of the construct within a host system, such as bacteria or eukaryotic cells described herein, results in the production of a fusion protein. The two split intein compounds (i.e., $I_C$ and $I_N$) of the fusion protein then assemble to form an active enzyme that splices the amino and carboxy termini together to generate a backbone cyclic peptide. Cyclic polypeptides can be generated using a variety of inteins. Methods of generating cyclic proteins can be found in the art, for example, in WO 00/36093 and WO 01/57183, incorporated herein by reference in their entirety.

As used herein, the term "intein" refers to a naturally-occurring or artificially-constructed polypeptide embedded within a precursor protein that can catalyze a splicing reaction during post-translation processing of the protein.

The following examples are provided for exemplification purposes only and are not intended to limit the scope of the invention which has been described in broad terms above.

EXAMPLE 1

Characterization of Phospho-Specific Antibodies Recognizing P-T668

Figure 1:
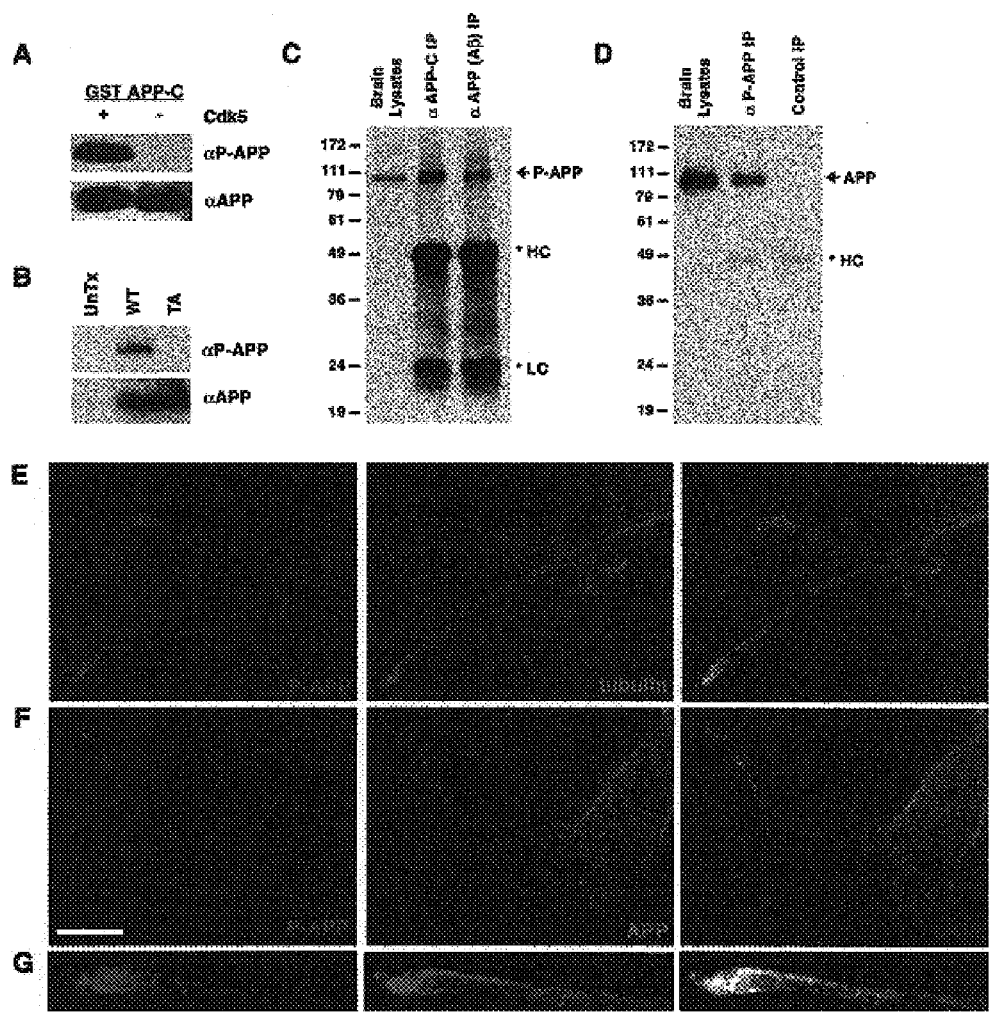
FIGS. 1A-1I depict the characterization of the P-T668 phospho-epitope specific APP antibody. (A) The P-T668 antibody recognizes APP phosphorylated by Cdk5 but not unphosphorylated APP. GST-APP(649-695) was incubated with or without Cdk5, separated by SDS-PAGE, and immunoblotted with either the P-T668 antibody (top panel) or an antibody against APP(649-695) (bottom panel). (B) The P-T668 antibody recognizes APP phosphorylated on T668. Wild-type (WT) and T668A APP were expressed in the catecholiaminergic (CAD) neuroblastoma cell line. Total cell lysates were separated on SDS-PAGE and blotted with the P-APP antibody (top panel). The same blot was then probed with a C-terminal APP antibody (bottom panel). (C) Immunoblot on SDS-PAGE separated human brain lysates using the P-T668 antibody indicated that this antibody recognizes a band of approximately 100 kDa (arrow). Two different APP antibodies, C16.1 (αAPP-C) and 4G8 (αAPP-Aβ), precipitate a co-migrating band. The asterisks indicate IgG heavy chain (HC) and light chain (LC). (D) Immunoprecipitation using the P-T668 antibody brings down APP that is recognized by a pan APP antibody (C 16.1) on an immunoblot. (E) Primary hippocampal neurons were stained with P-T668 (red), tubulin (Tuj 1, green) and DAPI (blue). (F) Primary hippocampal neurons were stained with P-T668 (red), APP (4G8, green) and DAPI (blue). P-T668 APP is localized to the end of neurites while APP is mainly found in the cell body. (G-I) Immunogold electron microscopy using the P-T668 antibody showed that T668 phosphorylated APP is localized primarily on vesicles approximately 50 nm in diameter (arrowheads) along neurites of primary cortical neurons. (G) Primary cortical neuron labeled with 5 nm gold-coupled antibody against P-T668. (H) Enlargement of the boxed area in (G). (I) Two representative P-T668 positive vesicles. Nu: nucleus, Mt: mitochondria. Scale bars: 15 μm (F), 2 μm (G) and 200 nm (H).
Figure 1:
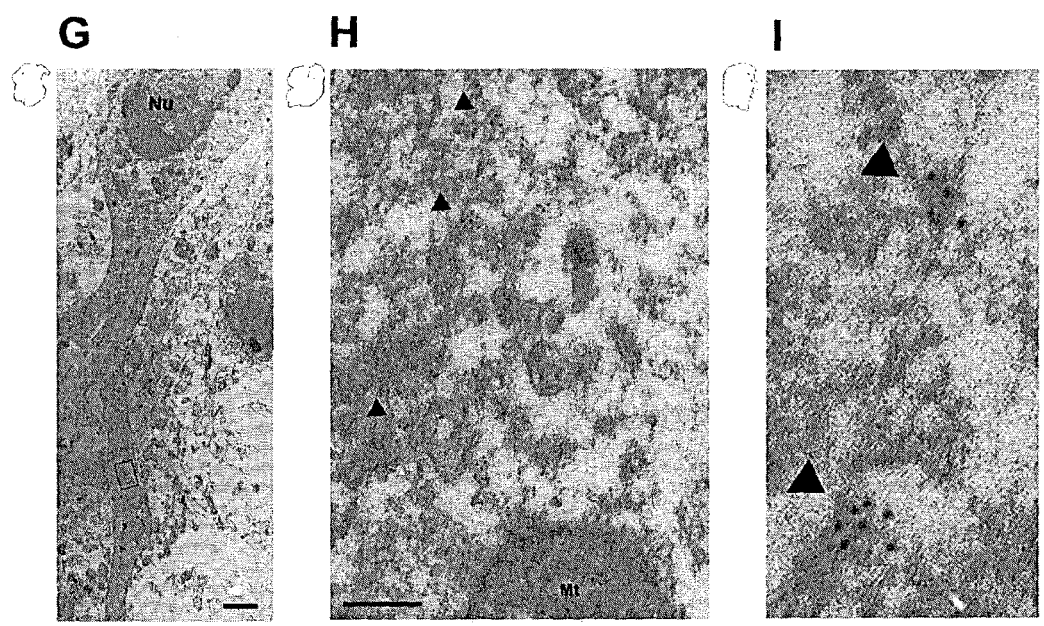

To study T668 phosphorylation of APP in normal and diseased brain samples, a rabbit polyclonal antibody against a phospho-T668 (P-T668) containing peptide was generated. To determine if the P-T668 antibody was specific to phosphorylated APP, a glutathione S-transferase (GST)-tagged recombinant protein containing the C-terminus of APP (APP-C) was generated and this protein was phosphorylated with recombinant p25/Cdk5 kinase. While the APP C-terminal antibody recognized both the phosphorylated and unphosphorylated forms of APP-C, the P-T668 specific antibody only recognized the phosphorylated form (FIG. 1A). To show that this antibody only recognized APP phosphorylated on residue threonine 668, Western blot analysis was performed on lysates from neuroblastoma cells transfected with either WT APP or the threonine to alanine mutant (T668A) APP. The P-T668 antibody recognized only WT APP but not the APP T668A mutant (FIG. 1B).

Western blot on total brain lysates showed that the P-T668 antibody recognized a protein species at approximately 100 kDa that comigrates with immunoprecipitates of both the APP C-terminal antibody and an antibody that recognizes the Aβ region of APP (FIG. 1C). Conversely, immunocomplexes prepared from immunoprecipitates using the P-T668 antibody were also recognized by the APP C-terminal antibody (FIG. 1D). Together, these data indicate that the P-T668 antibody specifically recognizes P-APP in vitro.

DNA Constructs

A pcDNA plasmid containing the human APP coding sequence was used as the template for a PCR reaction with the primers: 5' TACCGCTCGAGAATTCCCAAGA AGAAACAGTACACATC (SEQ ID NO:1) and 5' AATCTAGACTCGAGTGTTCT GCATCTGCTCAAAGA (SEQ ID NO:2). The PCR product, which codes for the cytoplasmic tail of APP (residues 649-695), was cloned into the vector pGEX-4T-2 (Pharmacia) to create a fusion protein with the cytoplasmic tail of APP fused N-terminally to GST (GST-APPC). The APP T668A and T668E constructs were generated via PCR using complementary primers as described (Niethammer et al. (2000) Neuron 28:697).

Antibodies

The phospho-epitope specific APP antibody was generated against a synthetic peptide antigen corresponding to APP phosphorylated at the T668 residue: VDAAVpT-PEERHC (SEQ ID NO:3) where pT denotes phosphothreonine. The peptide was conjugated to KLH (Pierce) with sulfo-MBS (Pierce) and injected into New Zealand White rabbits. The antiserum was first adsorbed against a corresponding non-phosphorylated peptide, VDAAVTPEERHC (SEQ ID NO:4), and then purified with the phospho-peptide coupled to a SulfoLink coupling column (Pierce). Peptides were synthesized by the Tufts peptide synthesis core facility and the antibody was made at Covance Research Products Inc.

Antibodies used for immunohistochemistry and Western blotting were as follows: anti-Cdk5 (C8 from Santa Cruz), anti-p35, anti-SV2 (a kind gift from C. Buckley), anti-cathepsin D (Calbiochem), anti-gp96 (a kind gift from H. Ploegh), anti-rab5 and anti-Bip (Stressgen), anti-rab4, anti-rab7 and anti-cathepsin D (Santa Cruz), anti-active m-calpain (a kind gift from R. Nixon), 4G8 (Senetek), 1G5 (a gift of Elan Pharmaceutical), C7 (kind gifts from D.

Selkoe), anti-actin (Sigma), anti-NeuN (Chemicon), anti-APP (C16.1, a kind gift from P. Matthews), 6E10 (Senetek), AT8 (Innogenetics), anti-BACE 1 (Oncogene Science and Calbiochem), anti-adaptin-γ and anti-GM130 (BD Biotechnology), and anti-presenilin monoclonal and polyclonal antibodies (Chemicon and a kind gift from D. Selkoe).

Primary Neuronal Culture

Primary hippocampal neurons were cultured as described from E18 rat embryos (Niethammer et al. (2000) *Neuron* 28:697). 8-day old cultures were treated with different concentrations of ionomycin (Calbiochem). In some cases, hippocampal neurons were incubated with either 20 µM roscovitine (Calbiochem) or 20 µM butyrolactone (Calbiochem) for 15 min at 37° C. before being treated with 4 µM ionomycin for 5 hours. Neurons were lysed in SDS sample buffer and lysates were separated on a 12% acrylamide gel and analyzed by Western blotting.

Transfection of neurons with plasmid constructs for Cdk5 and p25 were as described (Kusakawa et al. (1999) *J. Biol. Chem.* 275:17166). Neurons were transfected using calcium phosphate 3 days after plating. Sixteen hours later, neurons were fixed in 4% paraformaldehyde for 20 min, blocked and permeabilized in 10% NGS and 0.1% Triton in phosphate-buffered saline (PBS) for 20 minutes. Permeabilized neurons were incubated with primary antibodies overnight at 4° C., and then incubated with Oregon Green or Texas Red conjugated anti-mouse or anti-rabbit secondary antibodies (Molecular Probes). All images were captured using either a 40× or a 100× oil-immersion objective on a Nikon inverted microscope linked to a DeltaVision deconvolution imaging system (Applied Precision).

For the half-life experiment, primary neurons were treated with 30 µg/ml cycloheximide for the indicated time period. Neurons were homogenized in a buffer containing 0.32 M sucrose, 1 mM EDTA, 10 mM HEPES pH 7.4 supplemented with protease and phosphatase inhibitors. The homogenate was differentially centrifuged at 1000 g for 10 minutes, 3000 g for 10 minutes, 17,000 g for 10 minutes, and 100,000 g for 45 minutes to prepare the nuclear, heavy membrane, light membrane, and microsomal fractions respectively. Each fraction was lysed in sample buffer and separated on a 12% acrylamide gel for analysis.

Western Blot Analysis

Brain tissue was lysed with RIPA buffer (50 mM Tris pH 8, 150 mM NaCl, 1% NP-40, 0.5% DOC, 0.1% SDS, 1 mM DTT) plus inhibitors (2 µg/ml aprotinin, 2 µg/ml leupeptin, 1 µg/ml pepstatin, 100 µg/ml phenyl methyl sulfonyl fluoride (PMSF), 5 mM NaF, 5 mM $NaVO_3$) and analyzed as described herein.

EXAMPLE 2

Localization of T668 Phosphorylated APP

Using the P-T668 antibody, T668 phosphorylated APP was found to localize to neuronal processes and was enriched at growth cones and tips of neurites in primary rat hippocampal culture (FIG. 1E). While partial co-localization of P-APP and APP was observed in the growth cone (FIG. 1F), a pan APP antibody primarily labeled the ER and Golgi compartments in the cell body (FIG. 1F), indicating that the T668 phosphorylated form of APP represents a subpopulation exhibiting a subcellular localization pattern distinct from that of the major pool of APP. Immunogold electron microscopy images show that in addition to nerve terminals, P-APP was present on small vesicles that are roughly 50 nm in diameter along microtubules (FIG. 1G-I), indicating that T668 phosphorylation can target APP for transport down neurites.

Figure 2:
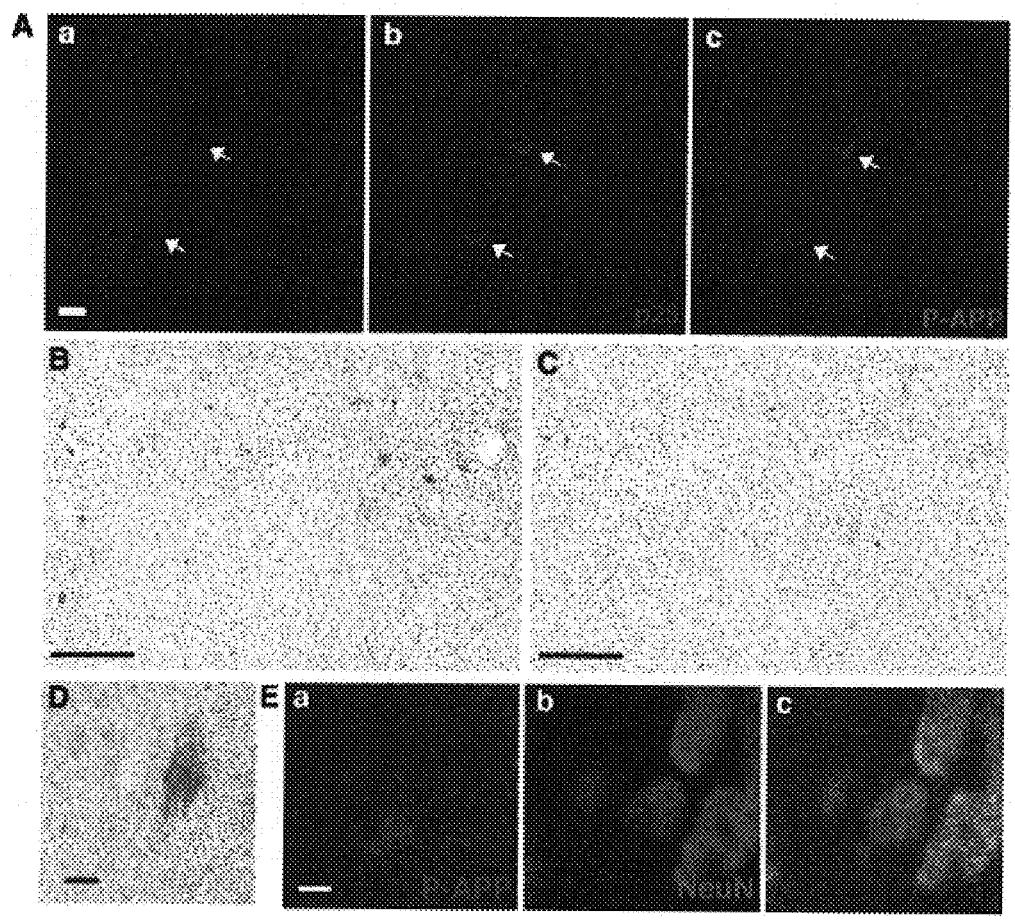
FIGS. 2A-2E depict that P25 causes elevation of T668 phosphorylation of APP. (A) P25/Cdk5 transfected neurons display increased P-T668 staining. Primary cortical neurons were transfected with p25 and Cdk5. 24 hours after transfection, neurons were fixed and stained with (a) DAPI to show all nuclei in the field, (b) anti-p25 to show neurons transfected with p25, and (c) anti P-T668 to assay P-APP levels in neurons. Arrows indicate neurons that are transfected with p25/Cdk5, which are also the ones that display elevation of T668 phosphorylation on APP. (B-C) APP phosphorylation is increased in p25 Tg mice. (B) Immunohistochemical staining of the amygdala region of a brain section from a p25 Tg mouse using the P-T668 antibody showing strong cell bodies and neuropil immunoreactivity. (C) P-T668 staining on brain section from a WT littermate does not display any strong signal. Sections were counter-stained with hematoxylin. (D) Enlargement of a p25Tg neuron with positive P-T668 staining. (E) Co-staining of P-T668 and the neuronal marker NeuN reveals that cells that accumulate P-T668 are neurons. Scale bars: 5 µM (A, D&E) and 25 µM (B, C).

To determine if hyperactivation of Cdk5 affects APP phosphorylation, p25/Cdk5 was overexpressed in primary rat cortical neurons by transfection. Neurons transfected with p25/Cdk5 displayed a significant increase in APP phosphorylation (FIG. 2A). Moreover, in p25/Cdk5 expressing cells, T668 phosphorylated APP was relocalized from the neurites to the cell soma, where it co-localized with p25 (FIG. 2A). Accumulation of p25 in vivo also lead to increased APP phosphorylation. An increase in P-APP staining in cell bodies of the amygdala was detected (FIGS. 2B&D). This increase in P-APP staining was not observed in WT littermates (FIG. 2C). Co-staining of P-T668 with NeuN, a neuron-specific marker, revealed that the P-T668 positive cells were neurons (FIG. 2E). Together these data indicate that overexpression of p25 in neurons causes accumulation and mislocalization of T668 phosphorylated APP.

Figure 4:
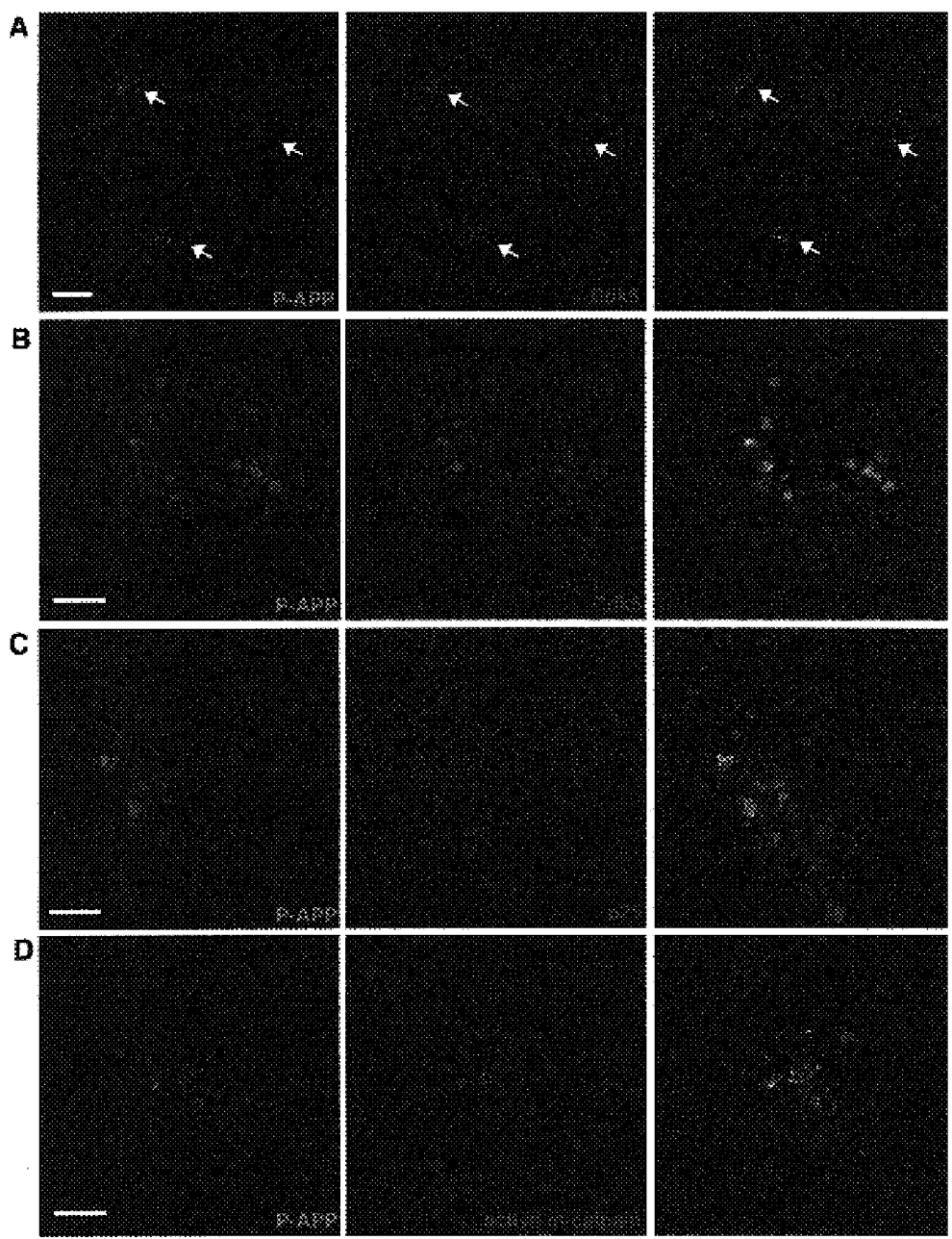
FIGS. 4A-4D depict that T668 phosphorylated APP co-localized with Cdk5, the Cdk5 activator p25, and an active form of the protease m-calpain in AD brain. (A) 40× DeltaVision deconvolution image showing P-APP (green) and Cdk5 (red) staining on an AD brain section. DAPI (blue) shows the nuclei in the field. Cdk5 was enriched in the same vesicles where phosphorylated APP was localized. Arrows show neurons with accumulated Cdk5 also displayed increased T668 phosphorylated APP. Other neurons in the field did not display accumulation of either Cdk5 or phosphorylated APP. (B) A 100× image of P-APP (green) and Cdk5 (red) co-staining shows Cdk5 co-localized with P-APP in the vesicular structures. (C) P25 (red), also co-localized with T668 phosphorylated APP (green). (D) An active form of the protease m-calpain (red), which cleaves p35 to generate p25, was detected in the same vesicular structures where T668 phosphorylated APP (green) was localized. Scale bars: 20 µM (A), 5 µM (B-D).
Figure 11:
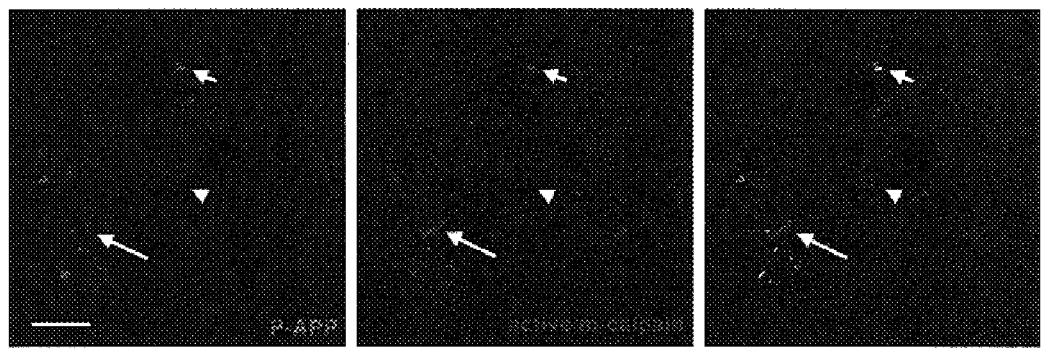
FIG. 11 depicts calpain staining in normal and degenerating neurons. Active m-calpain (red) is co-immunostained with P-T668 (green). In normal neurons, calpain is not active. As such, no active m-calpain staining is detected (arrowhead). In degenerating neurons, the active m-calpain antibody labels filamentous structures (long arrow) as well as vesicular structures positive for P-T668 (arrow). Size bars: 20 µm.

Notably, neurons that displayed increased APP phosphorylation also contained a significantly higher staining intensity of Cdk5 compared to other neurons in the same field (FIG. 4A). In normal cells, Cdk5 is diffusely distributed throughout the cell body and in neuronal processes (Patrick et al. (1999) *Nature* 402:615; Nikoloic et al. (1996) *Genes Dev.* 10:816). In neurons that accumulated phosphorylated APP, Cdk5 was enriched and co-localized with P-APP in vesicular bodies (FIG. 4B). In contrast, other kinases such as GSK3 (Ramelot et al. (2001) *J. Mol. Biol.* 307:871), CaMKII and Cdc2 did not show this co-localization. Since p25 represents the C-terminal 208 amino acid residues of p35, p35 can be distinguished from p25 by using antibodies against the N- and C-terminus of p35. A p35 C-terminus antibody that recognizes both p35 and p25 labeled the vesicular compartments enriched with P-APP (FIG. 4C), while a p35 N-terminus antibody did not, indicating that p25 co-localized with P-APP. Cleavage of p35 to p25 is mediated by the protease calpain. Using an antibody that specifically recognizes the active form of m-calpain (Grynspan et al. (1997) *Brain Res.* 763:145), an enrichment of active m-calpain was found in the vesicular structures where phosphorylated APP resides (FIG. 4D and FIG. 11). The co-localization of m-calpain, p25, Cdk5 and T668 phosphorylated APP in AD brains, in conjunction with the observation in primary neurons that ionomycin-induced phosphorylation of APP is eliminated by Cdk5 inhibitors, indicates that the calpain-mediated p35 to p25 conversion pathway is involved in the elevation of T668 phosphorylation on APP in AD brains.

Figure 5:
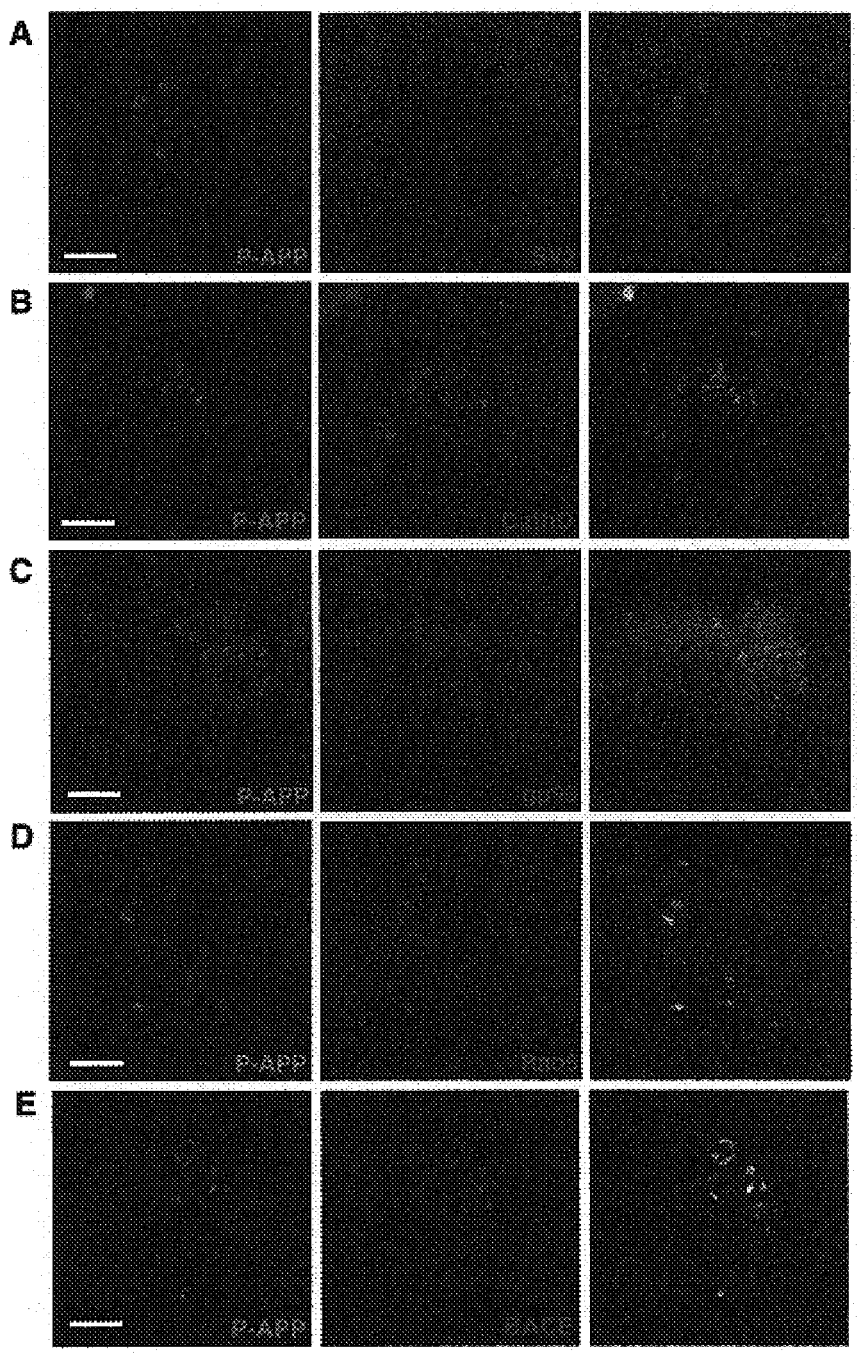
FIGS. 5A-5E depict that phosphorylated APP localizes to endosome-like compartments in neurons from AD brains. (A) 100× DeltaVision deconvolution image showing no co-localization between T668 phosphorylated APP (green) and a synaptic vesicle marker (SV2 in red). (B) No co-localization was detected between T668 phosphorylated APP (green) and a lysosome marker (cathepsin D in red). (C) T668 phosphorylated APP (green) did not co-localize with an ER marker (gp96 in red). (D) T668 phosphorylated APP (green) co-localized with an endosome marker (Rab5 in red). (E) Phosphorylated APP (green) co-localized with BACE (red), an endosome marker. Scale bars: 5 µM (A-E).

To determine the nature of the vesicular structures positive for P-APP, co-immunostaining was performed on AD hippocampal sections with a large panel of organelle markers. The staining results revealed that vesicular structures enriched in T668 phosphorylated APP were not synaptic vesicles (FIG. 5A), lysosomes (FIG. 5B) or part of the endoplasmic reticulum (ER) (FIG. 5C). Rather, the P-APP positive vesicles were labeled with the endosome markers Rab5 (FIG. 5D), and BACE (FIG. 5E), indicating that P-APP was enriched in the endocytic compartments in AD hippocampal neurons.

EXAMPLE 3

APP Phosphorylation and Neurotoxicity

To determine if neurotoxic conditions influence APP phosphorylation, primary hippocampal neurons were treated with ionomycin. Ionomycin, which induces conversion of p35 to p25, caused a marked elevation of T668 phosphorylation on APP. Two different Cdk-specific inhibitors, roscovitine and butyrolactone, inhibited T668 phosphorylation induced by ionomycin, indicating that APP is one of the Cdk5 targets whose phosphorylation is induced by neurotoxic conditions.

EXAMPLE 4

T668 Phosphorylation of APP in AD Brains

Figure 3:
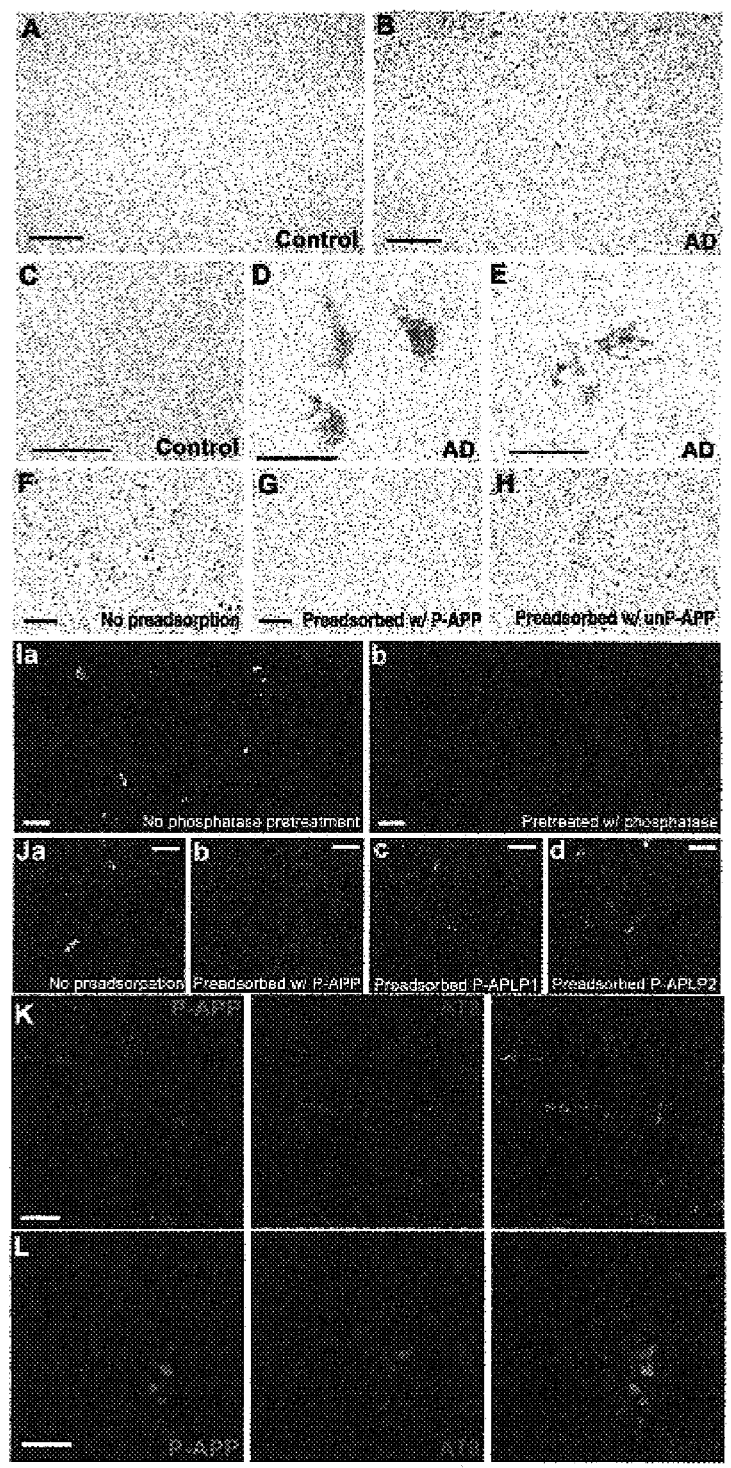
FIGS. 3A-3L depict that T668 phosphorylated APP is elevated in human AD brains. (A) Age matched control hippocampal section stained with P-T668 antibody. (B) AD hippocampal section stained with antibody against P-T668. Strong immunoreactivity is detected in pyramidal neurons and some plaque structures in the CA fields. (C-E) 40× magnified view of hippocampal sections. (C) Age matched control brain. (D) Pyramidal neurons containing enlarged vesicular structures positive for P-T668. (E) P-T668 positive dystrophic neurites. (F-H) 20× magnified view of AD hippocampal sections stained with P-T668 antibody (F), with the P-T668 antibody pre-absorbed with peptide containing the P-T668 epitope (G), or with the P-T668 antibody pre-absorbed with a cognate non-phosphopeptide (H). (I) P-T668 staining of AD hippocampal section without phosphatase treatment (Ia) or pretreated with alkaline phosphatase (Ib). (J) P-T668 staining of AD hippocampal section without preadsorption (Ja), or with P-T668 preadsorbed with a phosphorylated APP peptide (Jb), a peptide representing phosphorylated APLP1 (Jc) or one that represents phosphorylated APLP2 (Jd). (K, L) DeltaVision deconvolution images showing staining of P-APP and phospho-tau (AT8) on AD brain sections. APP phosphorylated on T668 is enriched in the same neurons that have increased phosho-tau staining. Scale bars: 500 µm (A, B), 15 µm (C-E), 200 µm (F-H), 20 µm (I, J, K) and 5 µm (L).
Figure 14:
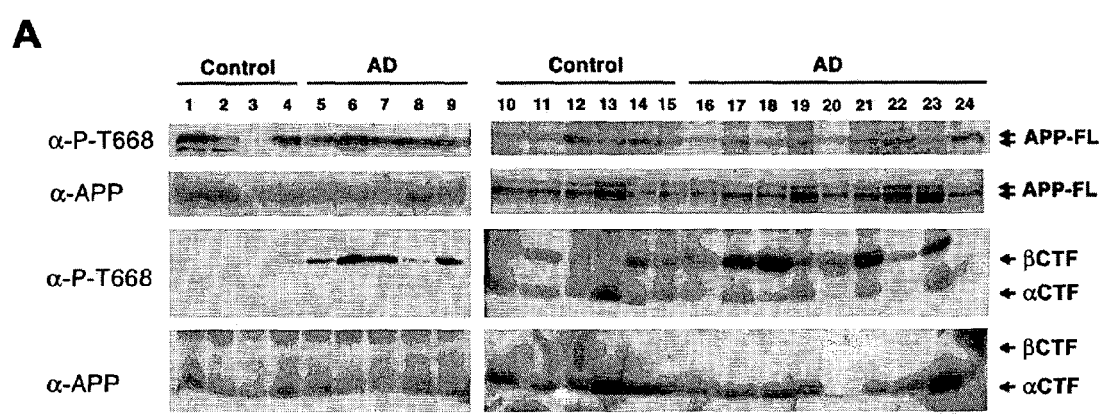
FIG. 14 depicts the elevation of C-terminal fragments of T668 phosphorylated APP in AD brains. Western blots of brain lysates from control hippocampal tissues (lanes 1-4, 10-15) and AD hippocampal tissues (lanes 5-9, 16-24) probed with P-T688 antibody or an antibody against the C-terminus of APP (C1/6.1).

To determine whether T668 phosphorylation of APP is affected in AD brain samples (case information is set forth in FIG. 14 and Table 1), immunohistochemistry was performed on human brain sections using the P-T668 antibody. Upon gross inspection, the staining patterns of T668 phosphorylation in age-matched control and AD brains differed markedly (FIG. 3A-E). Intense staining was observed in pyramidal neurons of the AD hippocampus, whereas little staining was detected in the cortex region (FIGS. 3B, D and 21A, B). Pre-adsorption of the antibody with a P-T668 containing peptide completely eliminated the staining, whereas a corresponding unphosphorylated APP peptide failed to reduce the staining (FIG. 3F-H). Pretreatment of AD hippocampal sections with alkaline phosphatase abolished staining by the P-T668 antibody (FIG. 3Ia-b).

Both mammalian APP homologues, APLP 1 and APLP2 contain a homologous threonine in the cytoplasmic domain. Pre-adsorption of the P-T668 antibody with APLP1 or APLP2 peptides containing a homologous phospho-threonine residue did not affect the staining pattern produced by this antibody (FIG. 3Ja-d). Thus, the P-T668 staining in AD brains is not due to phosphorylation of APLP1 or APLP2. Together, these results indicate that the P-T668 antibody specifically labels structures containing APP phosphorylated on the T668 residue in AD brains.

Figure 8:
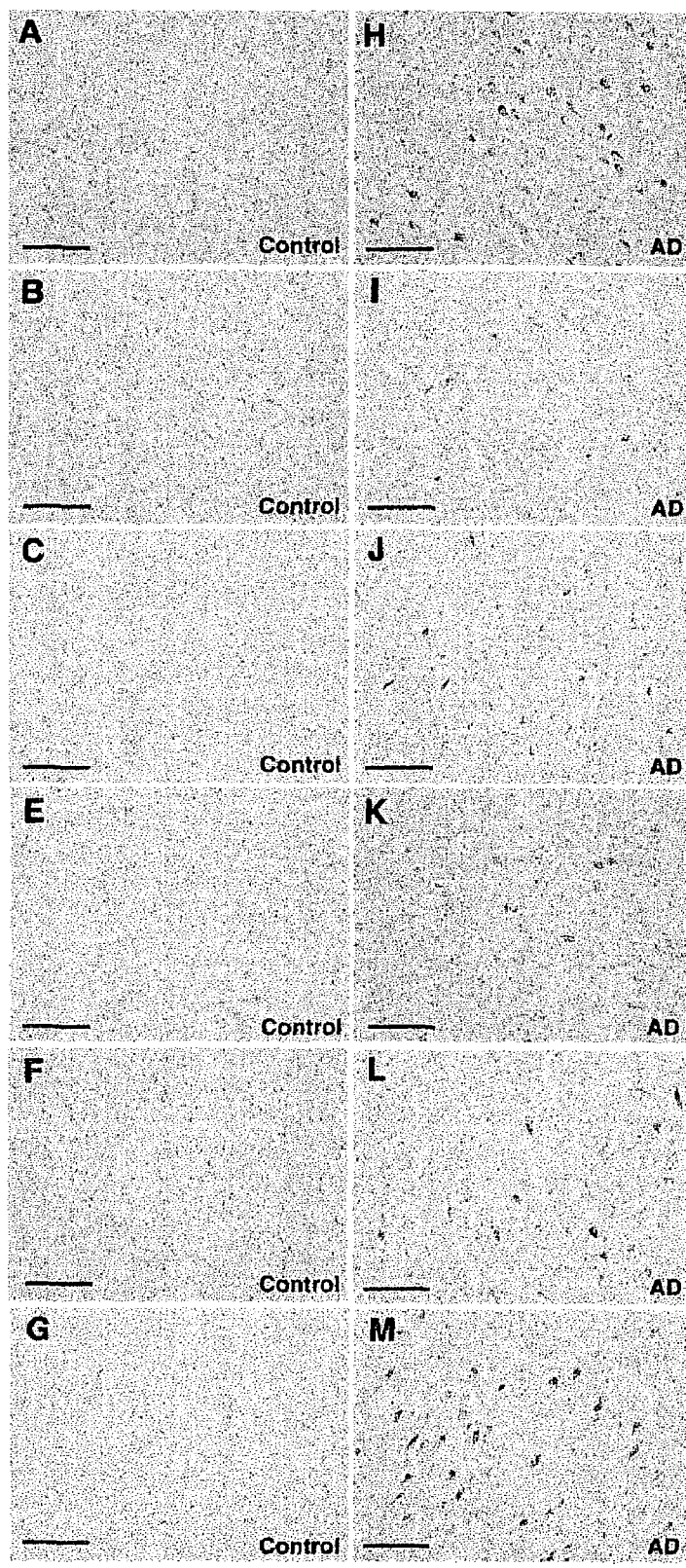
FIGS. 8A-8M depict vesicular accumulation of T668 phosphorylated APP in AD brains but not in age-matched control brains. Hippocampal tissue sections from six different AD brains (right panels, H-M) and 6 different control brains (left panels, A-G) were stained with the P-T668 antibody. Scale bar: 100 µm.

The localization of P-APP and pathological hallmarks for AD were examined in a total of 24 AD cases and 11 non-demented age-matched control cases. In general, two structures that displayed strong P-T668 staining were large, vesicular bodies within the cell soma of hippocampal neurons (FIG. 3D, FIG. 8) and dystrophic neurites (FIG. 3E, FIG. 21C-F). The distribution of P-APP was also investigated in the brains of 18 month-old APP(Sw) Tg mice. The P-T668 antibody labeled dystrophic neurites that were closely associated with amyloid plaques (FIG. 21G-J). However, no vesicular staining in the cell body was observed. Thus, in the mouse model for amyloid plaques, P-APP was only present in one of the two compartments where it is enriched in AD.

Figure 9:
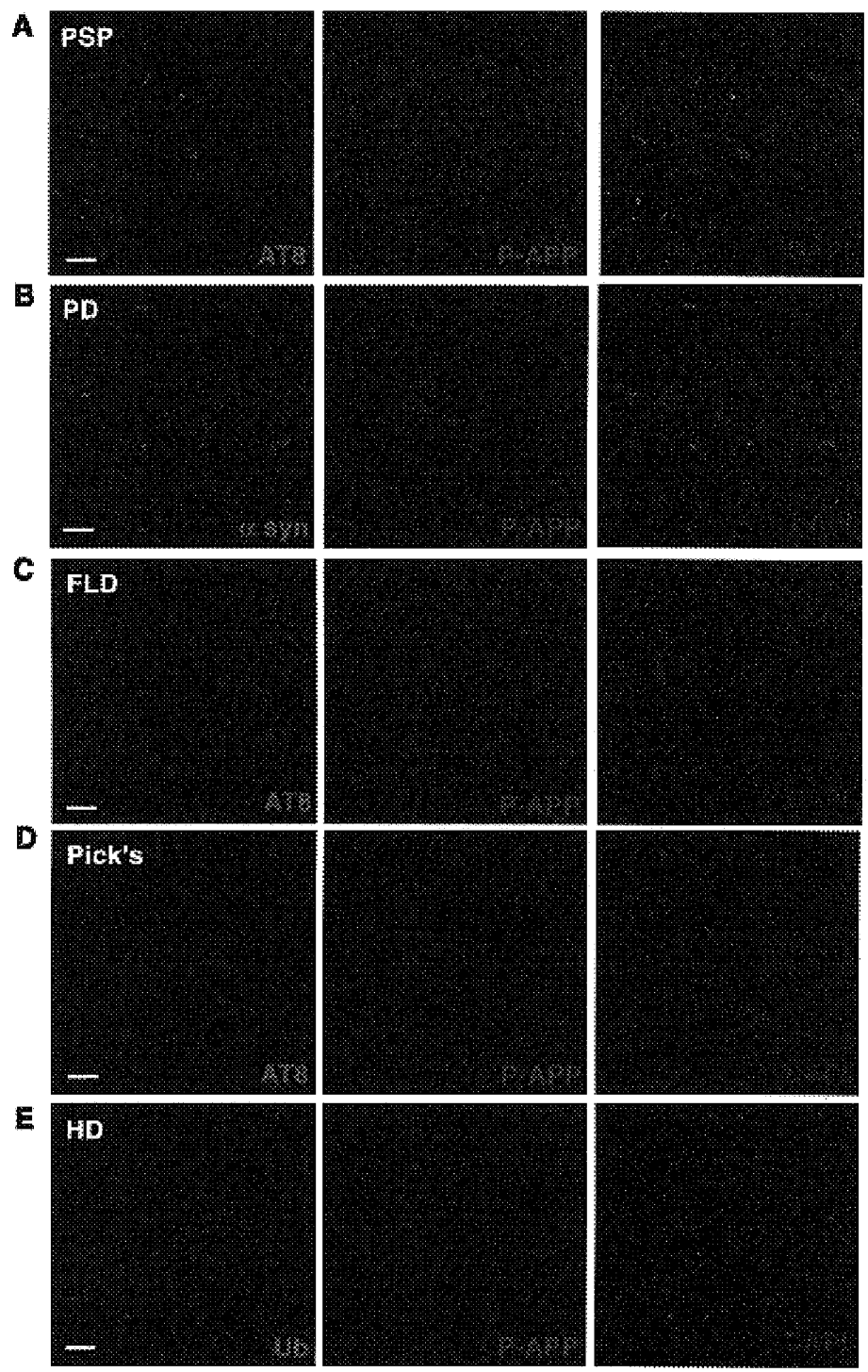
FIGS. 9A-9E depict T668 phosphorylated APP staining in different neurodegenerative diseases. (A) Co-staining of AT8 (green), P-T668 (red) and DAPI (blue) on tissue section from a case of progressive supranuclear palsy (PSP). (B) Co-staining of α synuclein (green) and P-T668 (red) on tissue section from a case of Parkinson's disease (PD). (C) Co-staining of AT8 (green) and P-T668 (red) from a case of frontal lobe dementia (FLD). (D) Co-staining of AT8 (green) and P-T668 (Red) from Pick's disease. (E) Co-staining of ubiquitin (green) and P-T668 (red) in Huntington's disease. Size bars: 20 µm.

In contrast, vesicular P-T668 staining was not observed in the 11 non-demented age-matched control cases. 19 human brain samples from individuals affected by neurodegenerative diseases including Pick's disease, progressive supranuclear palsy, frontal temporal dementia, Parkinson's disease and Huntington's disease were surveyed. Vesicular P-APP staining was not observed in any of these cases (except for a few cells in one case of familial frontal temporal dementia, see FIG. 9). These results indicate that the elevated vesicular P-APP staining is quite specific to AD.

Figure 10:
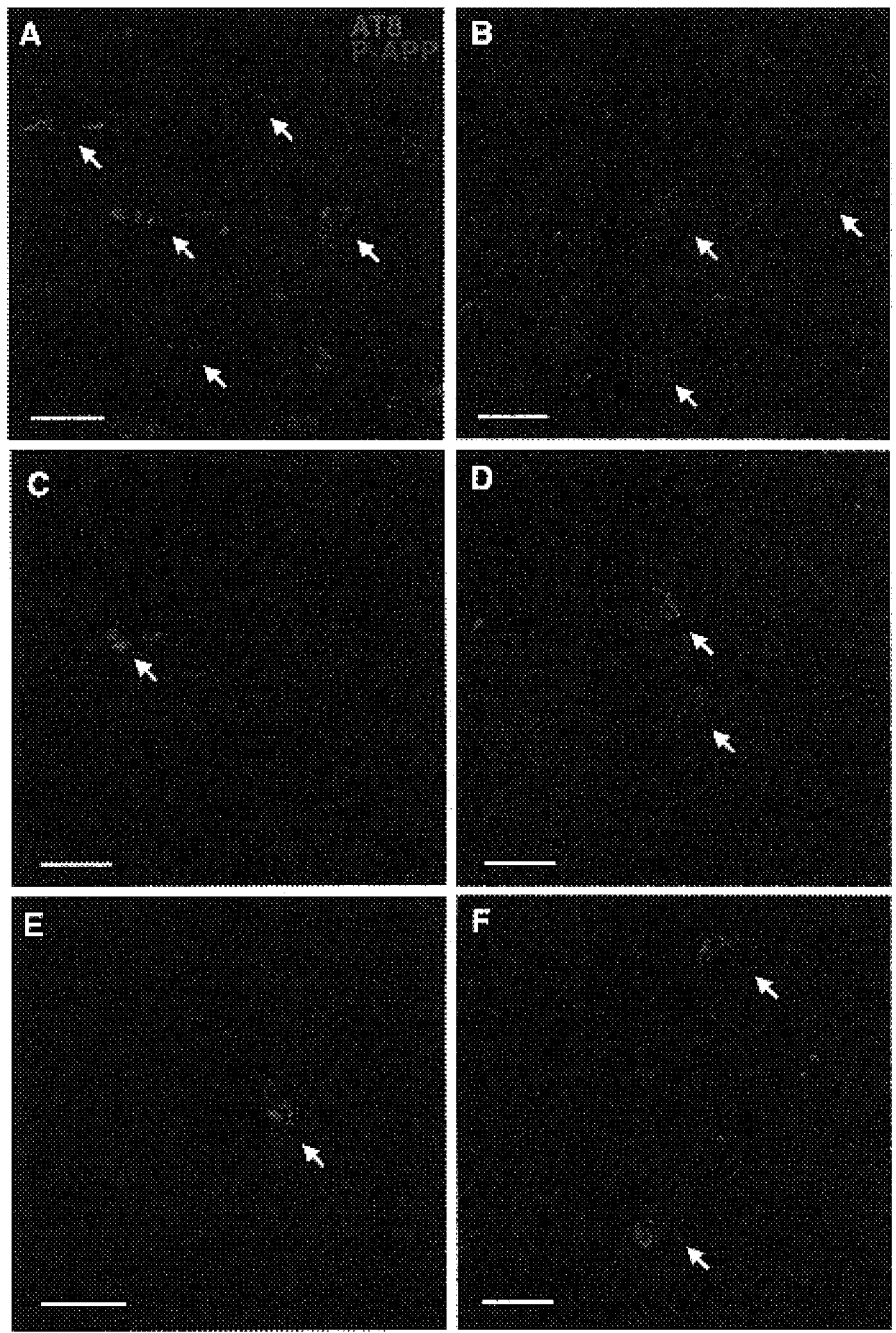
FIGS. 10A-10F depict that T668 phosphorylated APP is upregulated in neurons containing AT8. (A-F) Hippocampal tissue sections from six different AD cases were stained with AT8 (green), P-T668 (red), and DAPI (blue). Arrows show neurons in the field positive for both AT8 and P-T668. Size bars: 20 µm.

Double immunostaining of P-T668 and phospho-tau (AT8 or AT100) in AD brains revealed that a large proportion of P-T668 positive neurons were also positive for AT8 (FIG. 3K). Among 1373 neurons surveyed that were positive for P-T668, AT8 or both, 81% were double positive, 3% were only positive for P-T668 and 16% were only positive for AT8 (Table 2, FIG. 3K and FIG. 10). Of the neurons positive for AT8 only, most represented extracellular tangles that were remnants of degenerated neurons. This observation indicates that in AD brains, increased levels of P-APP are associated with afflicted neurons. While phosphorylated APP and phosphorylated tau are present in the same neurons, they exhibit different subcellular localization. P-APP is present in vesicular compartments while phospho-tau (AT8) is present in filamentous structures (FIG. 3L).

All AD cases analyzed displayed abundant amyloid plaques (labeled with an Aβ antibody, R1282), neurofibrillary tangles and plaque-associated dystrophic neurites (labeled with AT8), as well as abundant vesicles immuno-positive for the P-T668 antibody. In contrast, the age-matched control cases displayed either none or a low level of amyloid plaques, some neurofibrillary tangles, and in a few cases P-T688 immuno-positive vesicles and dystrophic neurites. The abundance of P-T668 immuno-positive structures found in all AD cases indicates that P-APP accumulation is associated with the disease state.

Immunohistochemistry

AD and control tissues were obtained from the autopsy service at Brigham and Women's Hospital. 24 cases of AD and 12 age-matched neurologically normal cases were evaluated. Neuropathological diagnosis of AD was confirmed according to the criteria of Khachaturian ((1985) *Arch. Neurol*. 42:1097).

Blocks of AD or control hippocampi were briefly fixed (1-48 hours) in 10% neutral buffered formalin. After fixation, the brain tissue was dehydrated and embedded in paraffin. Twenty-micron serial sections were cut, dried, and baked at 60° C. for 1 hour. Sections were deparaffinized in Histoclear (National Diagnostics) and rehydrated. Endogenous peroxidase activity was quenched by incubation of the sections in 0.3% hydrogen peroxide in methanol. The sections were pretreated with 88% formic acid for 10 minutes and microwaved in a citrate buffer (BioGenex). Sections were then blocked in 10% goat serum and incubated with primary antibody overnight at 4° C. Signal was visualized either using a horseradish peroxidase avidin-biotin complex system (Vector Laboratories) and 3,3'-diaminobenzidine (DAB) (Sigma) or by immunofluorescence. Sections used for immunofluorescence were pretreated with 0.3% Sudan Black (Sigma) to eliminate autofluorescence. All images were captured using a Nikon inverted microscope linked to a DeltaVision deconvolution imaging system (Applied Precision). For some fluorescence immunolabelling experiments, the primary antibody was directly labeled with Oregon Green using the FluoReporter Oregon Green 488 Protein labeling kit (Molecular Probes) according to manufacturer's specifications.

For peptide preadsorption experiments, antibodies were mixed with peptides at a 1:100 molar ratio and incubated overnight at 40° C. before being used for staining. Peptides used were as follows: P-APP: VDAAVpTPEERHC (SEQ ID NO:3) where pT denotes phospho-threonine; APP: VDAAVTPEERHC (SEQ ID NO:4); P-APLP1: VDPMLpTLEEQQC (SEQ ID NO:5); APLP1: VDPMLTLEEQQC (SEQ ID NO:6); pAPLP2: VDPMLpTPEERHC (SEQ ID NO:7) and APLP2: VDPMLTPEERHC (SEQ ID No:8).

Immunohistochemistry on p25 Tg mouse brain sections was performed as described (Ahlijanian et al. (2000) *Proc. Natl. Acad. Sci*. 97:2910). Images were captured using 10×, 20×, or 40× objectives with a Nikon inverted microscope and processed as described (Niethammer et al. (2000) *Neuron* 28:697).

TABLE 1

Case information of human brains analyzed by immunohistochemistry.

| Case Number | Diagnosis | Age | Sex | Vesicular Staining |
|---|---|---|---|---|
| 9933025 | control | 76 | F | − |
| 883599 | control | 73 | M | − |
| 877122 | control | 74 | M | − |
| 874523 | control | 80 | M | − |
| 8730225 | control | 72 | F | − |
| 8724222 | control | 87 | F | − |
| 00324 | control | N/A | N/A | − |
| A9863 | control | 81 | N/A | − |
| O9852 | control | 67 | N/A | − |
| O9853 | control | 74 | N/A | − |
| A9654 | Control | 80 | N/A | − |
| 9929623 | AD | 78 | F | ++++ |
| 9032538 | AD | N/A | F | ++ |
| 981523 | AD | N/A | N/A | +++ |
| 9712330 | AD | 71 | M | ++++ |
| 9117625 | AD | 90 | F | +++ |
| 9035134 | AD | 77 | F | +++ |
| 9821935 | AD | 92 | F | ++++ |
| 914440 | AD | 86 | F | +++ |
| 913636 | AD | 88 | F | ++++ |
| 99304 | AD | 88 | F | ++++ |
| 964629 | AD | 82 | F | ++++ |
| 9128222 | AD | 92 | F | +++ |
| 9930723 | AD | 88 | F | ++++ |
| 9018134 | AD | 90 | F | ++++ |
| 88359-9 | AD | 73 | M | ++++ |
| 8833025 | AD | 63 | M | +++ |
| 8825265 | AD | 85 | M | +++ |
| 8823932 | AD | 94 | F | +++ |
| 8723726 | AD | N/A | N/A | +++ |
| 8835421 | AD | N/A | N/A | +++ |
| 8833338 | AD | 84 | M | +++ |
| X102126 | AD | N/A | N/A | +++ |
| 891422 | AD | 62 | F | +++ |

TABLE 2

Quantification of cells labeled with P-APP and AT8.

| | |
|---|---|
| % cells labeled only with P-APP | 3% |
| % cells labeled with both P-APP and AT8 | 81% |
| % cells labeled with AT8 alone | 16% | n = 1373

EXAMPLE 5

Biochemical Analysis of T668 Phosphorylation of APP

Figure 6:
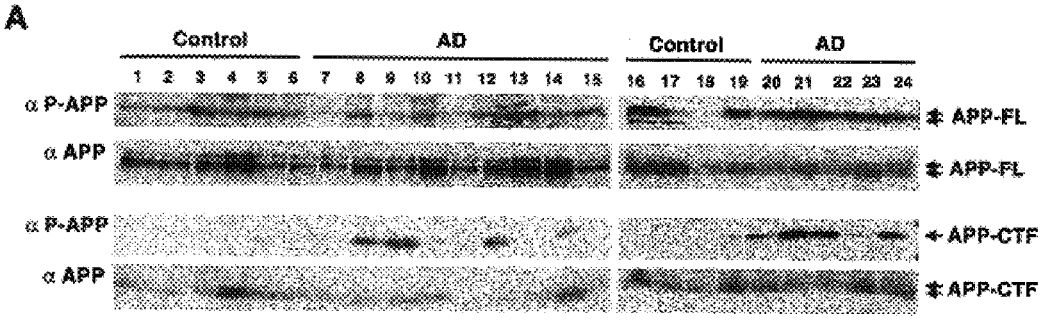
FIGS. 6A-6E depict that the C-terminal fragments of T668 phosphorylated APP is elevated in AD brains. (A) Western blots of brain lysates from normal control hippocampal tissues (lanes 1-6, 16-19) and AD hippocampal tissues (lanes 7-15, 20-24) were probed with an antibody against P-T688 or an antibody against the C-terminus of APP (C 16.1). No obvious difference in P-T668 was observed for full length APP (APP-FL). In 9 out of 14 AD cases, the C-terminal fragments of APP (APP-CTF) displayed increased phosphorylation on T668. (B) 100× image of T668 phosphorylated APP (green) and an antibody against the ectodomain of APP (1G5, red). (C) 100× image of T668 phosphorylated APP (green) and an antibody against the C-terminus of APP (C7, red). (D) Schematic diagram of peptides detected by MALDI analysis. APP immunoprecipitated by the P-T668 antibody from AD brain tissue was separated by sodium dodecyl sulfate-polyacrylamide gel electrophoresis (SDS-PAGE), digested with trypsin and analyzed by matrix-assisted laser desorption/ionization-time of flight (MALDI-TOF) mass spectrometry. Peptides identified are illustrated. The numbering of residues is based on APP695. The Cdk5 phosphorylation site T668 is in bold face. (E) A partial MALDI spectrum of APP digests showed phosphorylation on the C-terminus of APP. MS peaks representing phosphorylated tryptic peptides derived from APP are indicated. Size bars: 5 µM (B, C).
Figure 6:
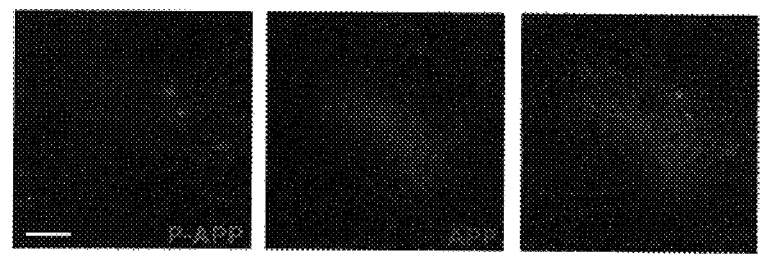
Figure 6:
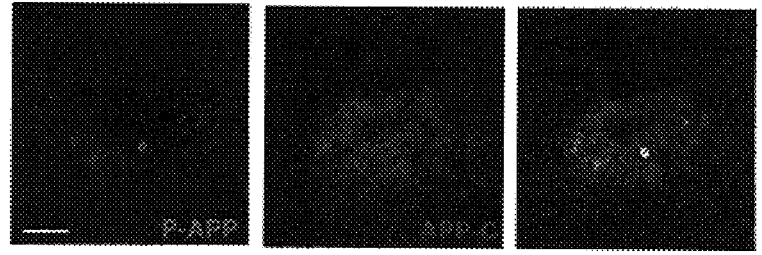
Figure 6:
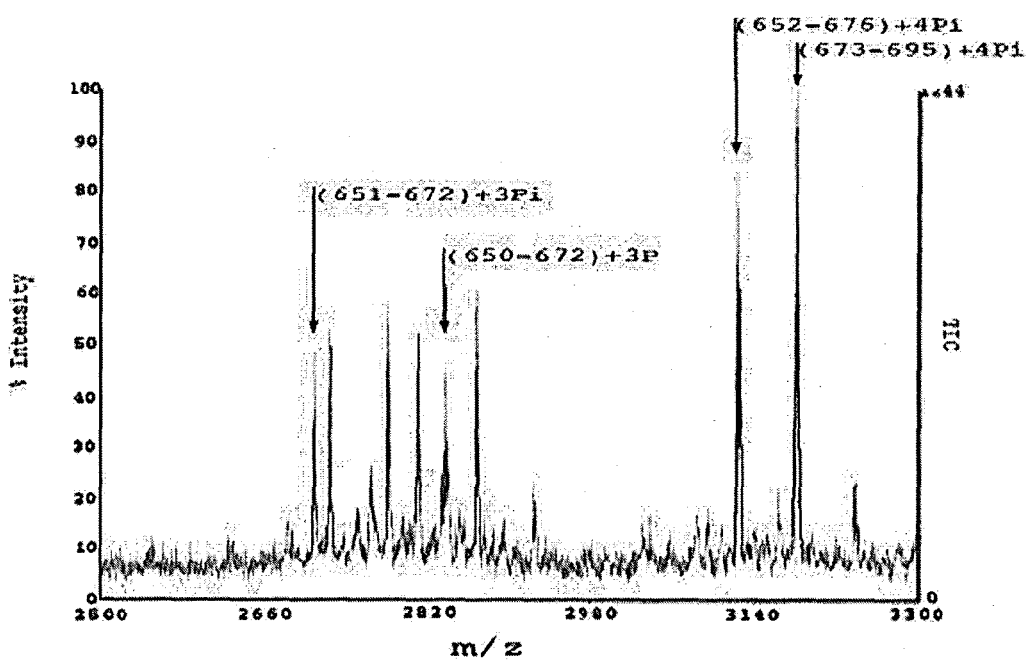

Immunohistochemical analysis revealed that T668 phosphorylated APP was elevated in AD hippocampal neurons. To determine whether such upregulation of T668 phosphorylation could be recapitulated using biochemical methods, Western blot analysis was performed on frozen hippocampal tissues from 14 AD and 10 age-matched control brains (Table 3). No significant difference in levels of T668 phosphorylated full-length APP was observed between AD and control brains (FIG. 6A). Intriguingly, T668 phosphorylation on the APP C-terminal fragments was determined to be considerably increased in 9 of 14 AD brains and 0 of 10 control brains. These observations indicate that the enrichment of T668 phosphorylated APP in the enlarged endosomes detected on AD brain sections represents phosphorylated APP C-terminal fragments. To test this possibility, AD hippocampal sections were immunostained using APP ectodomain specific and C-terminal specific antibodies. The APP ectodomain antibody, which recognizes full-length APP, labeled small vesicles that resembled part of the ER and Golgi compartments and displayed no detectable overlap with the large vesicles labeled by P-T668 (FIG. 6B). In contrast, the APP C-terminal antibody labeled both large and small vesicles. Extensive co-localization of P-T668 signal and APP C-terminal antibody signal was observed in the large vesicles (FIG. 6C). Together these results indicate that T668 phosphorylated APP C-terminal fragments (CTFs) are enriched in endosomes in AD hippocampal neurons.

To determine the phosphorylation sites, in addition to T668 of APP CTFs in AD, APP was immunoprecipitated from AD hippocampal lysates using the P-T668 antibody. The APP CTFs were resolved by SDS-PAGE and trypsin digested. Tryptic fragments were analyzed using MALDI-TOF mass spectrometry (MS). A summary of recovered peptides and a representative MALDI-TOF spectrum of tryptic digests are shown in FIGS. 6D and E. The recovered peptides span the entire APP, βCTFs region. The presence of peptides 596-612, 596-625, 602-612 and 602-625 indicated the existence of βCTF (C99) in the P-T668 immunoprecipitates prepared from the AD brain samples. Treatment of samples with alkaline phosphatase prior to MALDI analysis significantly reduced the intensities of the phospho-peptide signals and resulted in new ion peaks appearing at m/z positions representing dephosphorylated peptides, confirming that these peptides were indeed phosphorylated.

Interestingly, peptides spanning residues 650-672 and 651-672 were determined to contain 3 phosphates per peptide. Peptides 652-676 and 673-695 contained 4 phosphates per peptide (FIG. 6E). The sequence composition of the peptide ion with m/z 3123 (peptide 652-676) was selected and analyzed by post-source decay (PSD) MS. Based on the presence of corresponding y-ions and a phospho-tyrosine immonium ion it was determined that Y653, S655, and T668 were phosphorylated. Furthermore, the peptide 673-695 with 4 phosphates indicated that all potential sites (S675, Y682, T686, and Y687) were phosphorylated (FIG. 6E). These results indicate that in AD brains, APP CTFs contain at least 7 different sites that can be phosphorylated, including T668. As a control, APP CTFs were isolated from CAD cells overexpressing human APP using an APP C-terminal antibody (C1/6.1). Two phospho-peptides (peptide 651-672 and 650-672) containing three phosphates per peptide were detected, indicating that three out of four potential sites (Y653, T654, S655, T682) were phosphorylated. Signal representing peptide 673-695, which contains 4 potential phosphorylation sites (S675, Y682, T686, and Y687), was not detected (FIG. 22). This result shows that similar phospho-peptides of APP CTFs detected in AD brain samples are also present in recombinant APP expressed in cell cultures. Furthermore, as many potential sites are not phosphorylated in APP samples prepared from CAD cells, this indicates that the cytoplasmic domain of APP is hyperphosphorylated in AD. Since the phosphorylated residues include serines, threonines and tyrosines, this observation reveals that multiple protein kinases are activated in AD.

Cell Line and Neuronal Cell Culture

CAD cell lines were cultured in Dulbecco's minimal essential medium (Invitrogen), supplemented with 10% fetal bovine serum, L-glutamine and 1% penicillin-streptomycin sulfate in a humidified 5% $CO_2$ incubator (Suri et al. (1993) *J. Neurosci.* 13:1280).

Primary cultures of embryonic rat cortical neurons were prepared as described (Niethammer et al. (2000) *Neuron* 28:697). In brief, dissociated embryonic neurons from E18 Sprague Dawley pregnant rats were plated onto poly-D-lysine/laminin-coated 24-well plates or coverslips and maintained in neurobasal medium (Invitrogen) supplemented with B27 (Invitrogen), L-glutamine (Sigma-Aldrich) and 1% penicillin-streptomycin sulfate.

Mass Spectrometric Analysis

Blocks of AD hippocampi were lysed in RIPA buffer using a Dounce homogenizer. T668 phosphorylated APP proteins were isolated using a P-T668 antibody column according to the instructions by the manufacture (Amersham Biosciences). Isolated proteins were resolved using SDS-PAGE. Protein bands containing APP-CTFs were cut and subjected to S-carbamidomethylation and in-gel trypsin digestion (Stensballe and Jensen (2001) *Proteomics* 1:955). Peptide digests were extracted in 25 mM ammonium bicarbonate (pH 8.8) containing 25% (v/v) dimethyl formamide and further purified using ZipTipC18 (Millipore). Purified peptides were mixed with α-cyano-4-hydroxycinnamic acid matrix and analyzed by Voyager DE-STR mass spectrometer (Perseptive Biosystem). Post source decay experiments were performed according to the protocols provided the manufacture. Tables of mass/charge (m/z) of trypsinized APP peptides were generated using Protein Prospector (http://prospector.ucsf.edu/). The tolerance of the difference between experimental and theoretical m/z values in comparison was constrained under 300 ppm.

Aβ Measurement

Primary cortical neurons were cultured from E15 APP (Sw) Tg mice (Tg2576) (Hsiao et al. (1996) *Science* 274:99) as described (Niethammer et al. (2000) *Neuron* 28:697). 4-day-cultured neurons were replaced with new media (DMEM/F 12) and treated with different concentrations of roscovitine (Calbiochem) for 8 hours, or with butyrolactone (Calbiochem) for 16 hours. Aβ secreted into the media from each culture was analyzed by sandwich ELISA (Biosource) according to specifications by the manufacturer. Cell viability was measured by treating neurons with MTT (Sigma) at a final concentration of 0.5 mg/ml for 1 hour. After MTT treatment, cell medium was replaced with DMSO and the optical density of at 495 nm was determined.

Immunoprecipitation and In-gel Tryptic Digestion

A standard protocol for S-carbamidomethylation and in-gel trypsin digestion was used to generate peptide fragments from gel slices (Niethammer et al. (2000) *Neuron* 28:697). Peptide digests were extracted in 25 mM ammonium carbonate at pH 8.8 containing 25% (v/v) dimethyl formamide. Extracted peptides were further purified with ZipTipC18 (Millipore). Purified peptides were mixed with α-cyano-4-hydroxycinnamic acid matrix and analyzed in a Perseptive Biosystem Voyager DE-STR MALDI mass spectrometer. Tables of mass/charge and trypsin-treated digests for full-length APP were generated. The tolerance of the difference between experimental and theoretical m/z values in comparison was constrained under 300 parts per million.

TABLE 3

Case information of human brain analyzed by Western blotting analysis.

| Case Number | Diagnosis | Age | Sex |
| --- | --- | --- | --- |
| 9919 | AD | 78 | M |
| 9844 | AD | 83 | M |
| 9906 | AD | 88 | M |
| 9833 | AD | 82 | F |
| 9921 | AD | 86 | M |
| 9834 | control | 73 | F |
| 9925 | control | 76 | F |
| 9750 | control | 88 | F |
| 9931 | control | 85 | F |
| 45362 | control | 84 | F |
| 911 | control | N/A | M |
| 917 | control | 95 | F |
| 898 | control | 86 | M |
| 44653 | control | 71 | M |
| 873 | control | 74 | F |
| 94120 | AD | 71 | F |
| 94102 | AD | N/A | N/A |
| 94131 | AD | 79 | F |
| 93021 | AD | 74 | M |
| 94023 | AD | 86 | M |
| 94057 | AD | 97 | F |
| 91041 | AD | 72 | M |
| 94095 | AD | 66 | F |
| 90250 | AD | 89 | F |

EXAMPLE 6

T668 Phosphorylation Affects APP Processing

Figure 7:
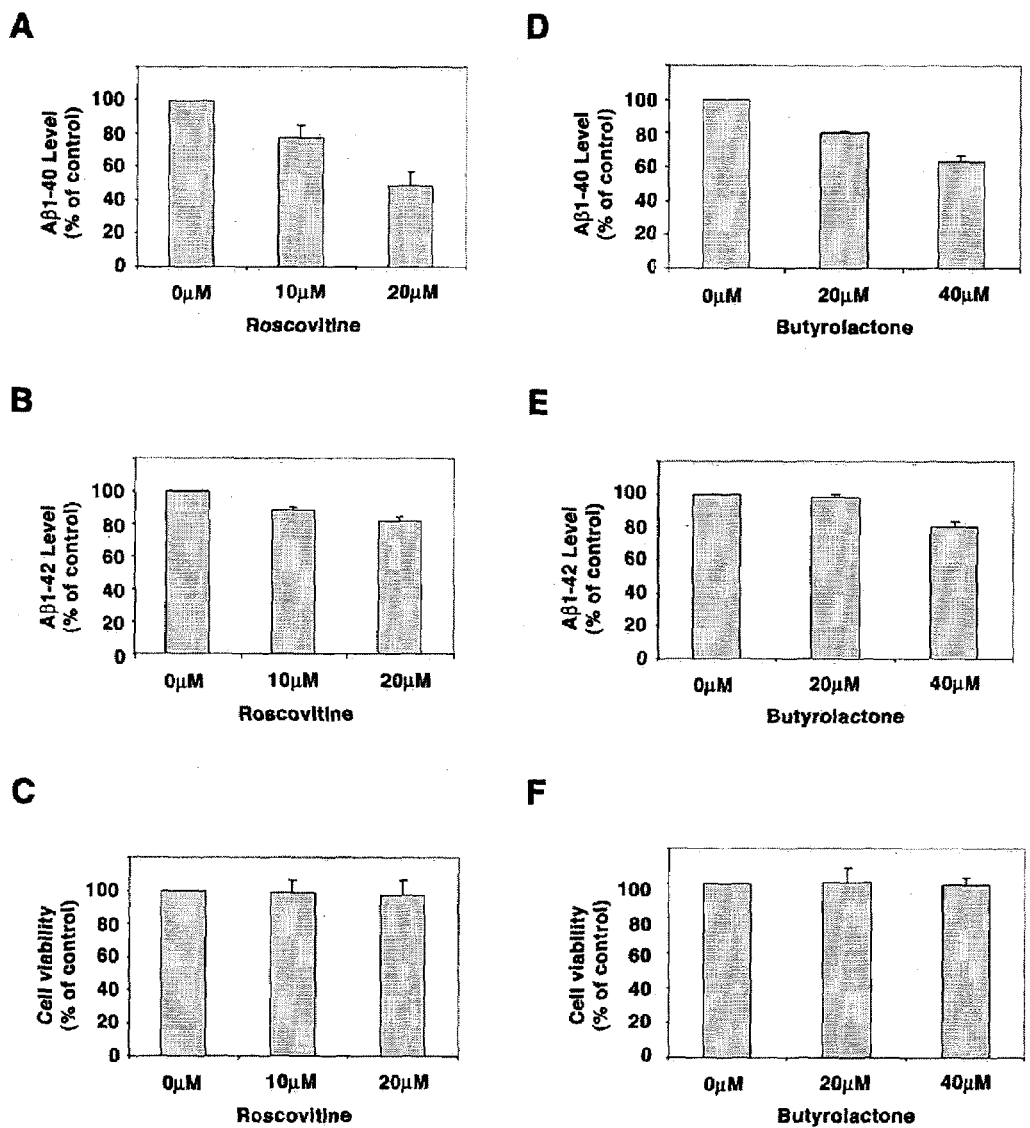
FIGS. 7A-7F depict that inhibition of Cdk5 reduces Aβ generation in a Tg mouse model of AD. (A) Inhibition of Cdk5 lead to a decrease in Aβ secretion. Primary mixed hippocampal and cortical neurons were cultured from E17 APP (Swedish) (Sw) Tg mice. 4-day-cultured neurons were treated with the indicated concentration of roscovitine for 8 hours and assayed for the level of Aβ(1-40) secreted into the media. The level of secreted Aβ(1-40) was normalized against the untreated control. The data are the averages (±s.d.) from four independent experiments. (B) As in (A), but the level of Aβ(1-42) in the media was assayed instead. (C) Cell viability was measured using the MTT assay. Cell viability was normalized against the untreated control. (D) 4-day-cultured neurons were treated with the indicated concentration of butyrolactone for 16 hours and assayed for the level of Aβ(1-40) secreted into the media. The level of secreted Aβ(1-40) was normalized against the untreated control. The data are the averages (±s.d.) from four independent experiments. (E) As in (D), but the level of Aβ(1-42) was assayed instead. (F) Cell viability was measured using the MTT assay.
Figure 13:
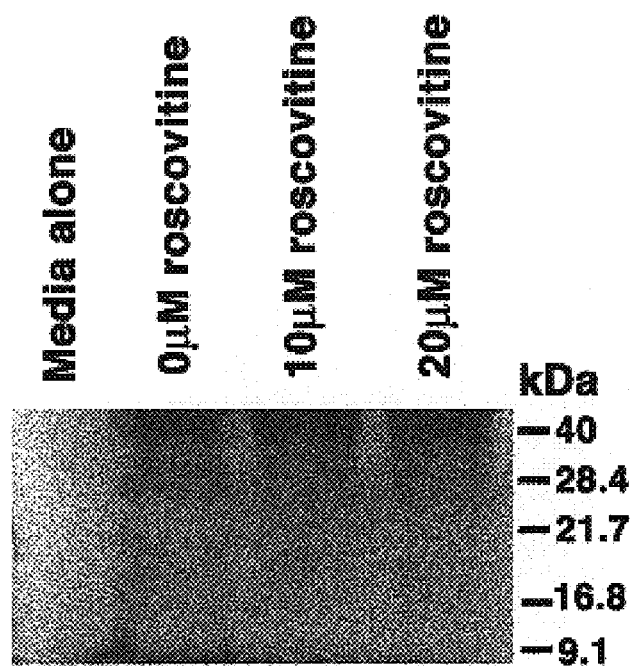
FIG. 13 depicts silver staining of culture media taken from neurons treated with roscovitine. Primary neurons from APP(Sw) neurons were treated with various amounts of roscovitine as indicated. Culture media was taken and separated on SDS-PAGE gel and silver staining was performed. The level of protein released into the culture media was similar in all cases.

T668 phosphorylation was inhibited to determine whether Aβ secretion was altered. To facilitate detection of Aβ, neurons from APP(Sw) Tg mice, a mouse model of AD which expresses human APP with the "Swedish" mutation K670N/M671L (Hsiao et al. (1996) *Science* 274:99), were cultured. Treatment of neurons with the Cdk-specific inhibitor roscovitine caused a dose-dependent decrease in secreted beta-amyloid (1-40) (Aβ(1-40)) levels (FIG. 7A). Levels of secreted beta-amyloid (1-42) (Aβ(1-42)) were also reduced (FIG. 7B). The reduction in Aβ(1-40) secretion was not due to a decline in cell viability as shown by the MTT assay (FIG. 7C). The general secretion processes of neurons were not affected as conditioned culture media from untreated and drug-treated cultures did not reveal any difference by gel silver stain (FIG. 13). Butyrolactone, another Cdk inhibitor, had a similar effect on reducing Aβ level (FIGS. 7D to 7F). These results indicate that T668 phosphorylation has a positive effect on Aβ secretion and inhibition of this phosphorylation event reduces Aβ generation.

Figure 12:
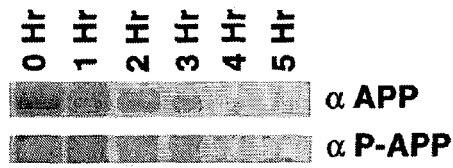
FIGS. 12A-12D depict that phosphorylated APP displays a longer half-life than APP. Primary cortical neurons were treated with cycloheximide for the indicated time. Cells were fractionated into heavy membranes, light membranes and microsomes through differential centrifugation and assayed for the level of APP (top panels) and phosphorylated APP (bottom panels). In the microsomal fraction, phosphorylated APP had a much longer half life when compared to APP. (D) CAD neuroblastoma cells were transfected with WT APP, T668A APP or T668E APP. Transfected cells were replated after 12 hours. Eight hours after replating, cycloheximide was added for the indicated time. Cells were lysed and fractionated into soluble and membrane fractions. While the APP T668A mutant had similar half-life to that of WT APP, the T668E mutant, which mimics the phosphorylated form of APP, prolonged the half-life of APP.
Figure 12:
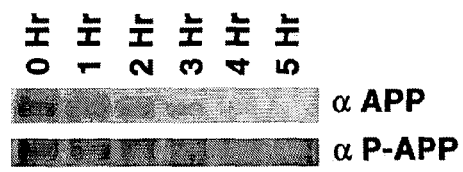
Figure 12:
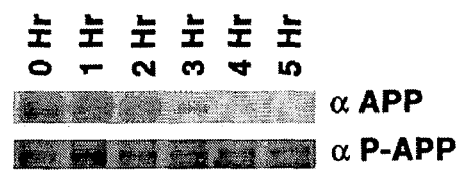
Figure 12:
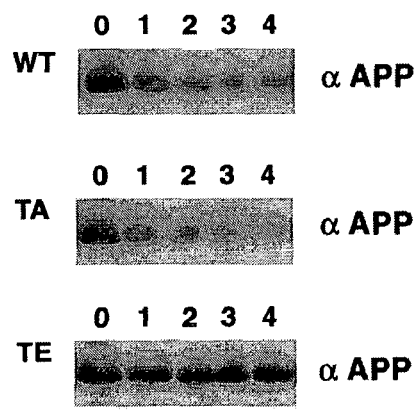

Phosphorylated APP displayed a longer half-life than APP in primary cortical neurons treated with cycloheximide. In the microsomal fraction, phosphorylated APP had a much longer half-life when compared to APP (FIG. 12A-C). Furthermore, while the APP T668A mutant had a similar half-life to that of WT APP, the T668E mutant, which mimics the phosphorylated form of APP, prolonged the half-life of APP (FIG. 12D).

Aβ Measurement by ELISA Assay (1) T668 kinase inhibitor: Primary cortical neurons were cultured from E18 Rat at a density of $4 \times 10^5$ cells/well in 24-well plates. Two days after plating, neurons were infected with recombinant herpes simplex virus (HSV) expressing WT APP for 16 hours. Subsequently, 70% of culture media was replaced with fresh medium and neurons were treated with indicated concentration of roscovitine or butyrolactone. 8 hours after inhibitor treatment, culture media was collected and subjected to sandwich ELISA assay according to specifications by the manufacturer (Biosource).

(2) T668A mutant: Primary cortical neurons from E18 rat were cultured at a density of $2\times10^5$ cells/well in 24-well plates. Two days after plating, 50% of culture media was replaced with fresh medium. Neurons were subsequently infected with equal titer of HSV expressing either WT or T668A APP. 20 hrs after infection, culture media was collected and subjected to sandwich ELISA assay. The most dramatic effect on Aβ generation was observed 24 hours after infection. By 48 hours after infection, the effect was less pronounced. Data were analyzed by t test using Prism (GraphPad). Differences were considered significant at $p<0.05$.

EXAMPLE 7

T668 Phosphorylated APP is Enriched in Endocytic Compartments and Co-localized with BACE1 in AD Brain To determine the nature of the large vesicular structures positive for P-APP (FIG. 3D), double immunofluorescence staining was performed on AD hippocampal sections with a large panel of organelle markers. As P-T668 antibody recognizes both full length APP and APP CTFs, the staining indicated localization of both full length P-APP and phosphorylated APP CTFs. It was determined that P-APP positive vesicles could be labeled by the endosome markers Rab4 (FIG. 15A), Rab5 (FIG. 15B) and EEA1 (FIG. 15C), but not by the lysosome markers cathepsin D (FIG. 15D) or cathepsin B (FIG. 23A), the synaptic vesicle marker SV2, the Golgi markers GM130 or MannII, or the ER markers Bip/Grp78 and GP96 (FIG. 23B). These co-staining results indicate that T668 phosphorylated APP is enriched in the endocytic compartments of AD hippocampal neurons.

Figure 15:
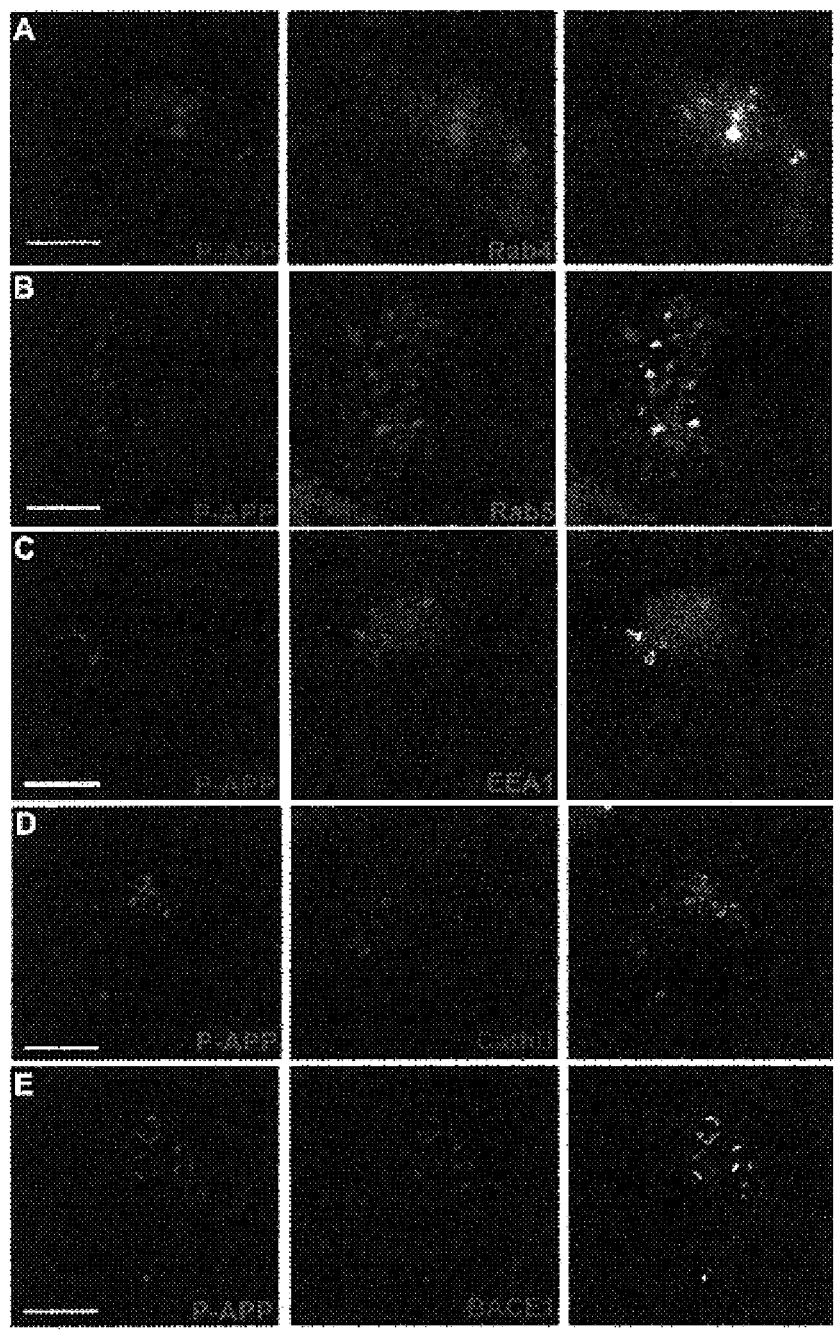
FIGS. 15A-15E depict the subcellular localization of P-APP in AD brain sections. (A-D) P-APP was localized to endocytic compartments but not lysosomes in AD brains. T668 phosphorylated APP co-localized with endocytic vesicle markers: Rab4 (A), Rab5 (B) and early endosome associated protein (EEA1) (C), but not with the lysosome marker, Cathepsin D (D). (E) Co-localization of T668 phosphorylated APP and β-secretase (BACE1) in the enlarged vesicles in AD brains. Scale bars: 5 µm.

The presence of APP processing enzymes in P-APP positive vesicles was also examined. Interestingly, the β-secretase BACE1 staining (recognized by a BACE1 antibody from Oncogene Science) was robust in the P-APP positive neurons. Furthermore, BACE1 displays extensive co-localization with P-APP (FIG. 15E). A different BACE1 antibody (from Calbiochem) gives rise to the same staining pattern in AD brains. Antibodies to PS1 (from Chemicon and a kind gift from D. Selkoe) did not specifically label the P-APP positive vesicles in AD brain sections. These data indicate that T668 phosphorylated APP co-localizes with BACE1 in enlarged endosomes in AD brains.

EXAMPLE 8

Co-Localization of T668 Phosphorylated APP and BACE1 in Primary Neurons

Figure 16:
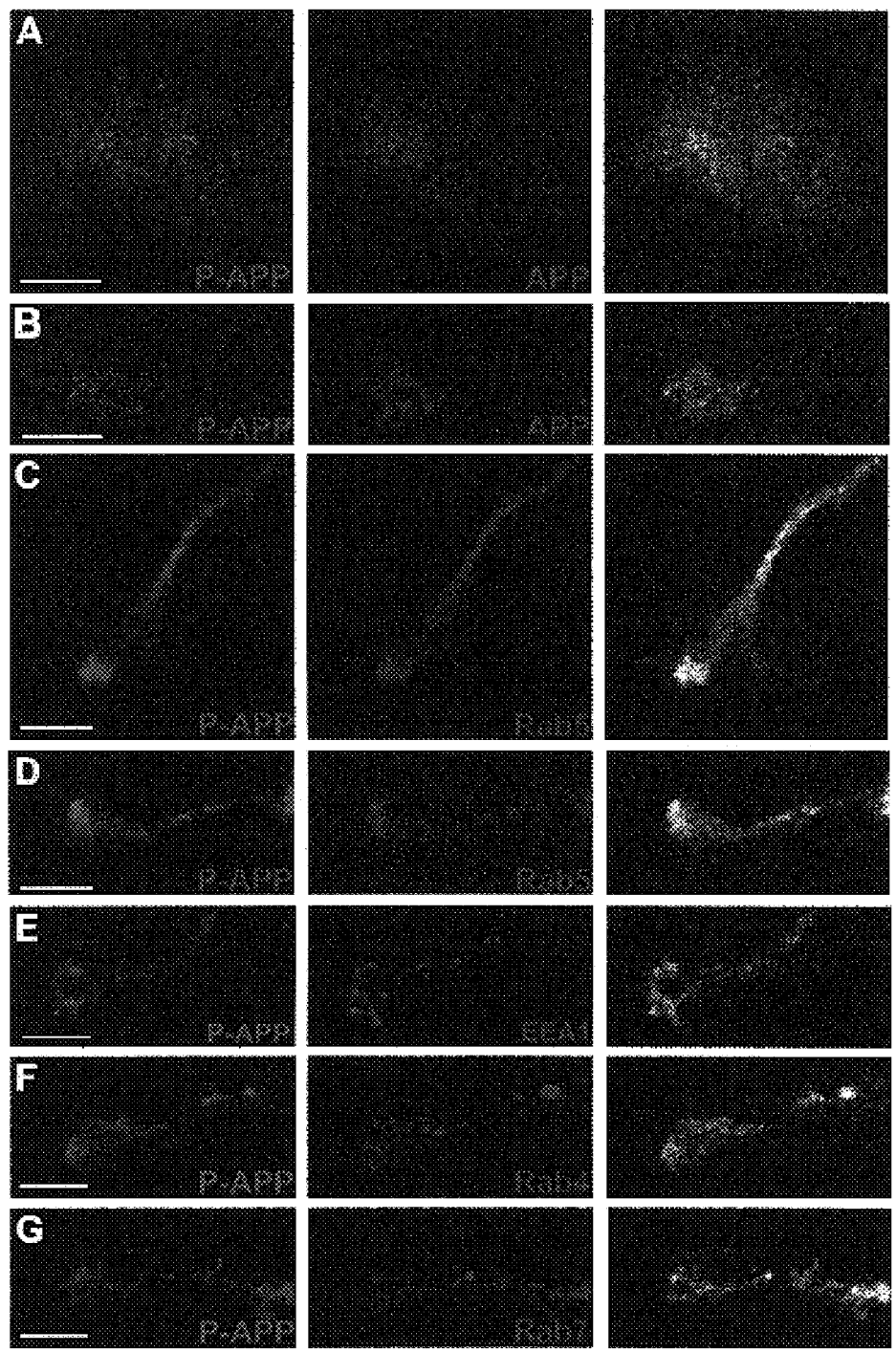
FIGS. 16A-16G depict the subcellular localization of P-APP in cultured primary cortical neurons using double immunofluorescence staining of rat primary cortical neurons. (A-B) Co-staining of P-APP and regular APP (C 1/6.1) in the soma (A) and growth cone (B). (C, D) Co-localization of P-APP and Rab5 in the growth cones. (E-G) Co-staining of P-APP and early endosome marker EEA1 (E), recycling endosome marker Rab4 (F) and late endosome marker Rab7 (G). Scale bars: 5 µm.
Figure 17:
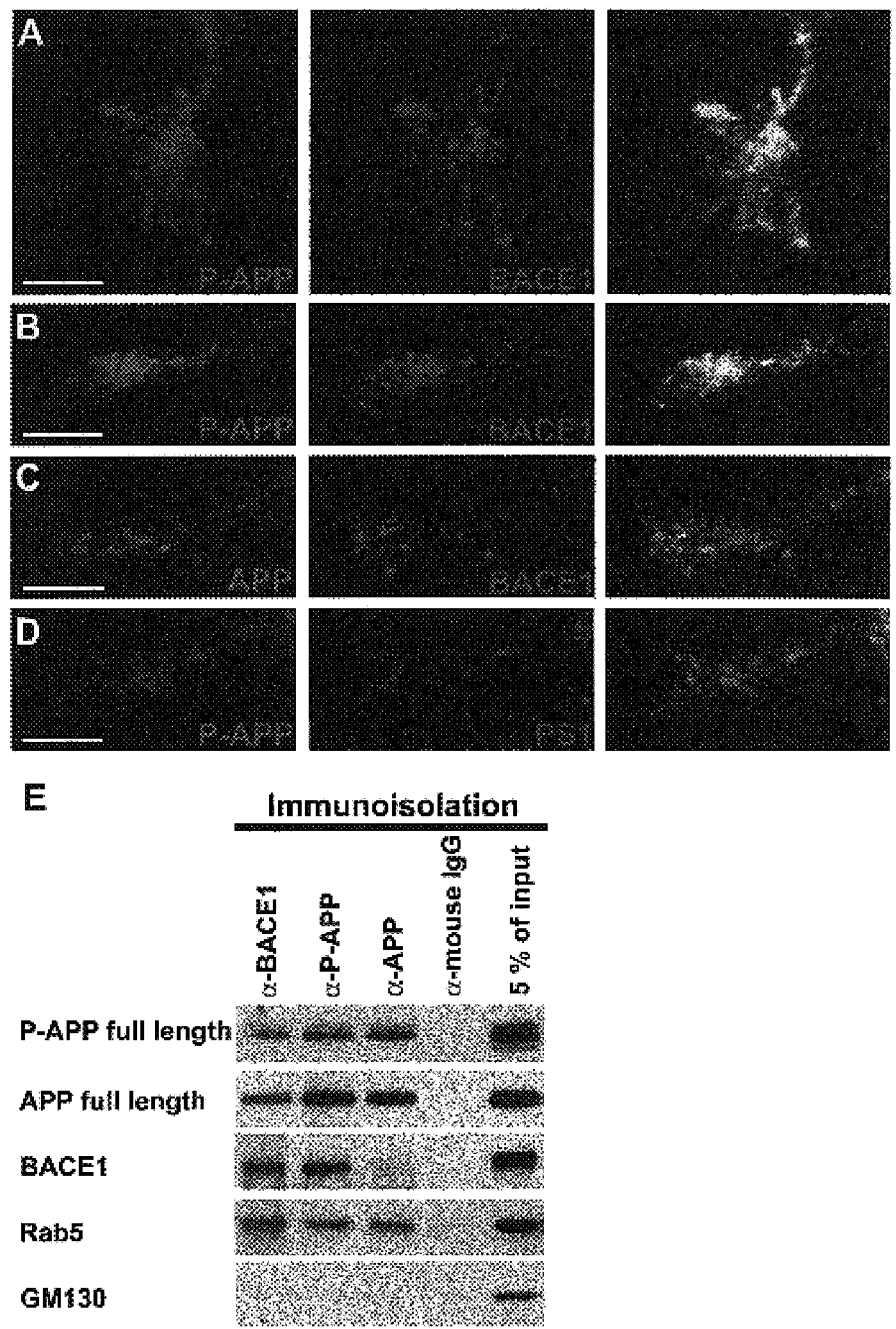
FIGS. 17A-17E depict co-localization of T668 phosphorylated APP with BACE1 in primary cortical neurons. (A, B) Co-staining of P-APP and BACE1 in the growth cones. (C) Co-staining of regular APP (C1/6.1) and BACE1 in the growth cone. (D) Co-staining of P-APP and Presenilin 1 (PS1) in the growth cone. Scale bars: 5 µm. (E) Immunoisolation of P-APP, APP and BACE1 containing vesicles. Vesicular organelles were immunoisolated from mouse brain using M-280 Dynabeads conjugated to anti-P-T668, anti-APP or anti-BACE1 antibodies. Immunoisolates were examined by Western blot analysis.
Figure 24:
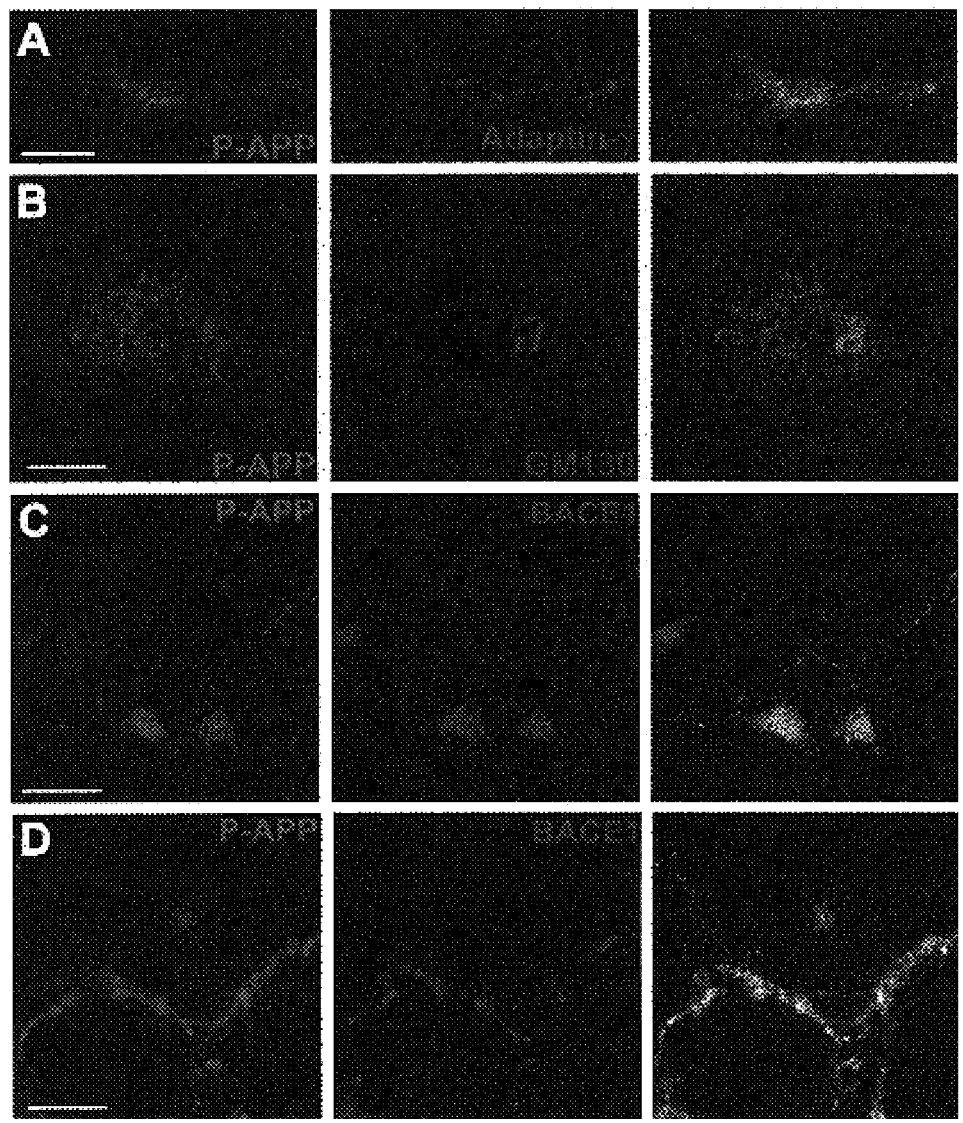

To determine the subcellular distribution of P-APP and its physiological relationship with BACE1, double immunostaining was performed on normal rat primary cortical neurons. In these neurons, P-APP signal appeared punctate in the soma and growth cones with a distribution pattern somewhat distinct from that of regular APP (FIG. 16A, B). Interestingly, P-APP showed substantial co-localization with the early endosome marker Rab5 in the growth cones (FIG. 16C, D). Modest overlap between P-APP and EEA1 (early endosome marker, FIG. 16E), Rab4 (recycling endosome marker, FIG. 16F), Rab7 (late endosome marker, FIG. 16G) or adaptin-γ (trans-Golgi network (TGN) marker, FIG. 24A) was observed. There was little co-localization of GM130 (cis-Golgi marker, FIG. 24B) and P-APP. Interestingly, P-APP and BACE1 displayed extensive co-localization in the growth cones of young neurons (FIG. 17A, B) and partial co-localization in neurites of 10-day old cultured neurons (FIG. 24C, D). Only limited co-localization, of regular APP and BACE1 was observed (FIG. 17C). P-APP and PS1 also showed little co-localization in the growth cones (FIG. 17D).

Immunoisolation experiments were performed to further characterize P-APP, APP and BACE1 containing vesicles (FIG. 17E). It was determined that the endosome marker Rab5 was present in P-APP, APP and BACE1 immunoisolates. GM130, a cis-Golgi marker, was not detected in any of the immunoisolates. The levels of BACE1 in P-APP immunoisolates were higher than those in APP immunoisolates, indicating that T668 phosphorylated APP preferentially co-localized with BACE1. Together, these experiments indicate that P-APP is in the same subcellular compartment as the APP processing enzyme BACE1, in both AD brains and cultured neurons.

EXAMPLE 9

Figure 18:
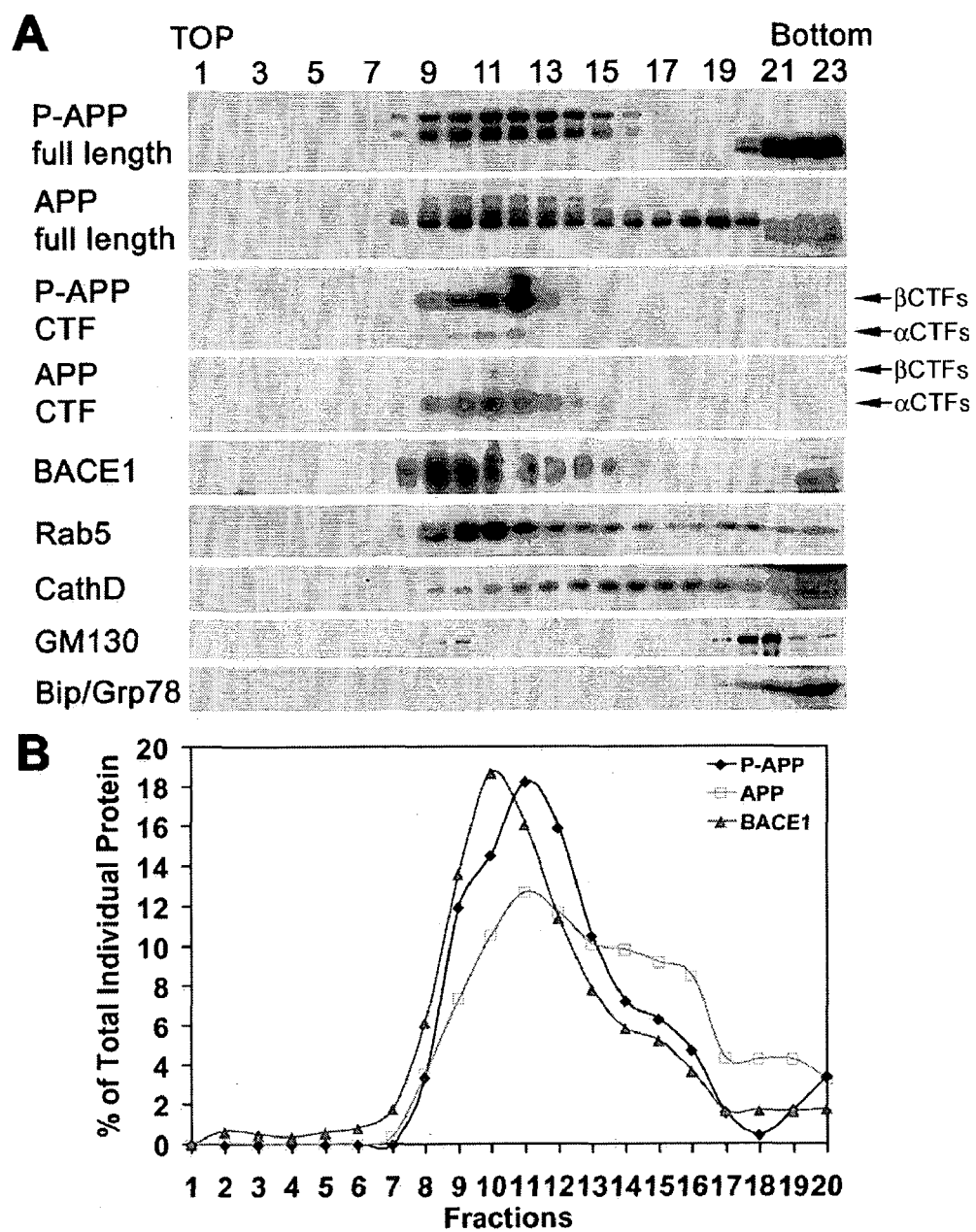
FIGS. 18A-18D depict co-fractionation of T668 phosphorylated APP with BACE1 and endosome markers. (A) Adult mouse brain lysate was fractionated through an iodixanol step gradient. Western blot analysis shows the distribution of P-APP, APP, Rab5 (early endosome marker), Cathepsin D (lysosome marker), GM130 (Golgi marker), Bip (ER marker), and the beta-secretase BACE1. (B) Quantification of protein distribution of A (fractions 1-20) showing that full length P-APP co-fractionates with BACE1. (C) Distribution of WT and T668A APP, expressed in rat primary cortical neurons using recombinant herpes simplex virus (HSV), in an iodixanol step gradient. The distribution pattern of BACE1 resembled that of WT APP. (D) Distribution of WT APP in an iodixanol step gradient after roscovitine treatment (15 µM for 8 hr). APP distribution shifted to heavier membrane fractions after roscovitine treatment.
Figure 18:
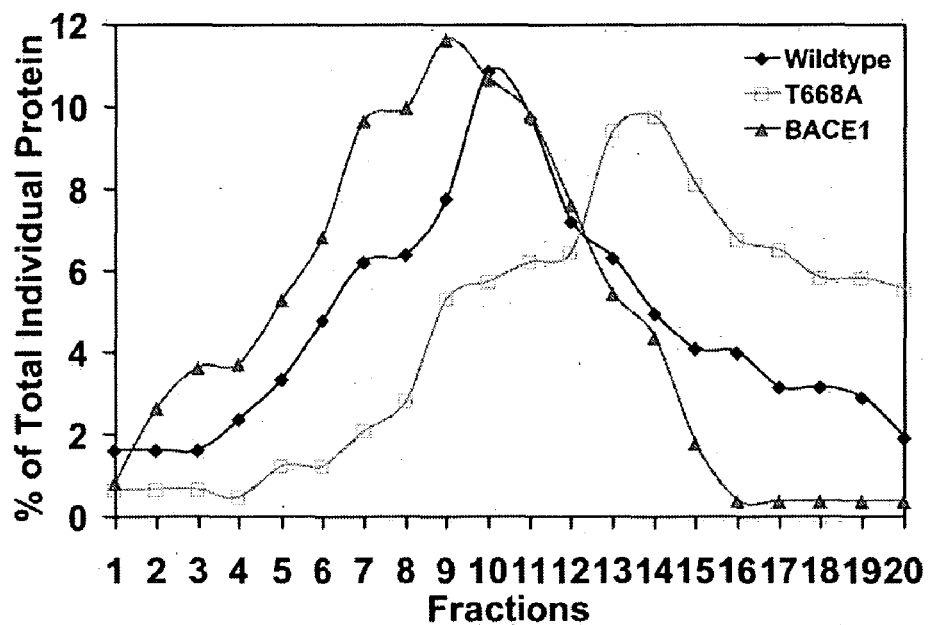
Figure 18:
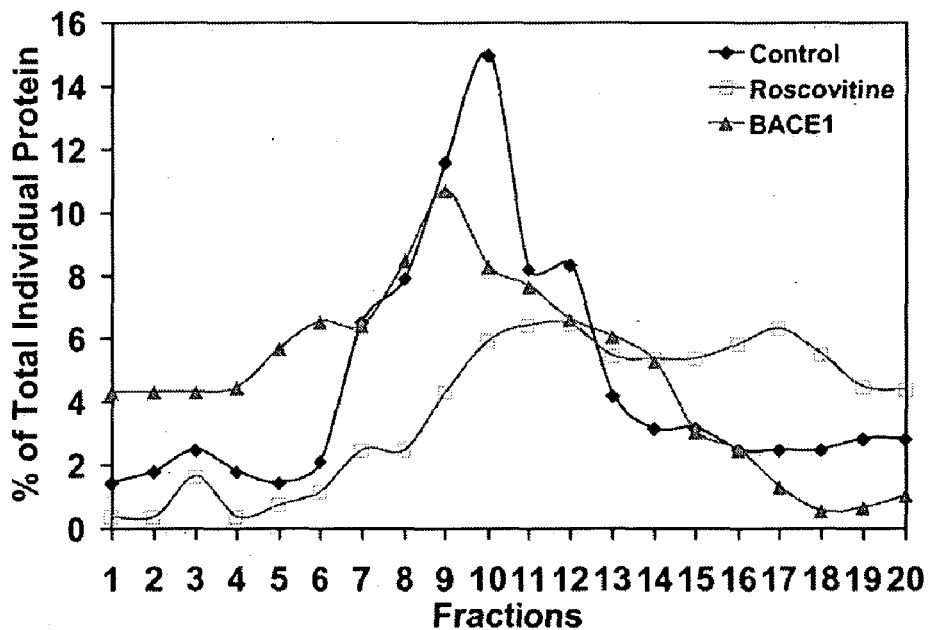

T668 Phosphorylated APP Co-Fractionates with BACE1 and Endosome Markers in an Iodixanol Step Gradient Biochemical fractionations were performed to gain additional insight into the subcellular localization of P-APP. Organelles in an adult WT mouse brains were separated through an iodixanol step gradient (FIG. 18A). Western blot analysis using the APP C-terminal antibody showed that full length APP had a broad distribution between fractions 8-20. Full length P-APP displayed a more restricted profile between fractions 8-16. P-APP signal was also detected in the bottom of the gradient (fractions 21-23), which can represent unsegregated lysates or immature, less glycosylated P-APP in the early secretory pathway. P-APP CTFs had a very discrete distribution spanning fractions 9-12, whereas APP CTFs were present between fractions 8-16. The APP CTFs detected by the P-T668 antibody displayed a higher molecular size than those detected by the APP C-terminal antibody by SDS-PAGE, indicating that the P-T668 antibody can preferentially label the beta-secretase product(s) of APP.

Organelle markers revealed that the early endosome marker Rab5 displayed a broad distribution, which overlapped with P-APP. Lysosomes, as identified by cathepsin D, also displayed a broad distribution, which was shifted to the right of the gradient. The Golgi apparatus (GM130) and ER (Bip) segregated to the bottom of the gradient. This result, in conjunction with immunocytochemistry and immunoisolation, indicates that T668 phosphorylated APP was specifically localized to the Rab5 positive endocytic compartment. Digitalization and plotting of the Western blot signals of fraction 1-20 revealed that full length APP, P-APP and BACE1 largely co-segregated in the fractions 8-13 of iodixanol gradient with the APP signal extended to the heavier fractions of the gradient (FIG. 18B).

To assess the significance of T668 phosphorylation in APP subcellular localization, WT APP and the T668A mutant APP were introduced into primary cortical neurons using recombinant herpes simplex virus (HSV). Twenty hours post infection, cell homogenates were fractionated through iodixanol step gradient and the distribution of APP in the collected fractions was analyzed. Interestingly, WT APP exhibited more extensive co-segregation with BACE1 than the T668A mutant APP, which was shifted to the heavier fractions of the gradient (FIG. 18C, immunoblots in FIG. 25A). APP distribution shifted to heavier membrane fractions after roscovitine treatment (FIG. 18D, immunoblots in FIG. 25B). These data indicate that T668 phosphorylation plays a role in the intracellular trafficking of APP.

Immunocytochemistry

Primary cortical neurons from E18 rat embryos were cultured at a density of $1\times10^5$ cells/well in 24-well plates. Two days after plating, neurons were fixed in 4% paraformaldehyde for 30 min, blocked and permeabilized in 10% normal goat serum and 0.1% Triton in PBS for 20 min. Permeabilized neurons were incubated with primary antibodies for 1 hr at RT, and subsequently incubated with Oregon Green or Texas Red conjugated anti-mouse or anti-rabbit secondary antibodies (Molecular Probes). Images were captured using a Nikon inverted microscope linked to a DeltaVision deconvolution imaging system (Applied Precision).

Immunodepletion

Immunodepletion was performed by lysing the mouse brain in radioimmunoprecipitation (RIPA) buffer (150 mM NaCl, 50 mM Tris, pH 8.0, 1% NP-40, 0.5% sodium deoxycholate, 0.1% SDS containing protease and phosphatase inhibitors 1 mM PMSF, 20 mM NaF, 20 mM β-glycerophosphate, 1 µg/ml aprotinin, 1 µg/ml leupeptin) using a dounce homogenizer. The lysates were centrifugated at 13,000 rpm for 15 min at 4° C. 300 µg of lysates were incubated with indicated amounts of antibodies for 1 hr at 4° C. in RIPA buffer. Then 30 µl of 50% slurry of protein A-Sepharose (Amersham Pharmacia) was added, and the tubes were rocked at 4° C. for an additional 1.5 h. The immunoprecipitates were washed three times with RIPA buffer, and resuspended in Laemmli sample buffer. Proteins were resolved using SDS-PAGE and then analyzed by Western blot analysis.

Immunoisolation

Adult mouse brain was homogenized in 2 ml of immunoisolation buffer (250 mM Sucrose, 20 mM HEPES, pH 7.3, 5 mM $MgCl_2$, 20 mM Sodium fluoride, 20 mM beta-glycerolphosphate, and protease inhibitors 1 µg/µl leupeptin and aprotinin and 1 mM PMSF) by 20 strokes in a dounce homogenizer followed by an additional 20 strokes in a 1 ml syringe fitted with 21-gauge needle. Lysates were centrifuged at 3,000 rpm for 15 min. The post-nuclear supernatant was collected and centrifuged at 27,000 rpm for 30 min to precipitate vesicles. The resulting pellet was resuspended in immunoisolation buffer that did not contain sucrose. Equal amounts of vesicle suspension were incubated at 4° C. overnight with indicated antibody that had been pre-conjugated to M-280 Tosylactivated Dynabeads (Dynal Biotech) according to instructions by the manufacturer. Immunoisolates were washed three times with immunoisolation buffer containing 0.1% BSA, resuspened in Laemmli sample buffer, and then subjected to Western blot analysis.

Iodixanol Step Gradient

Half of an adult mouse brain (1 month old) was homogenized in 1 ml of homogenization buffer (HB) (250 mM Sucrose, 20 mM Tris-HCl, pH 7.4, 1 mM EGTA, 1 mM EDTA, 4 mM Sodium pervanadate, 40 mM Sodium fluoride, 40 mM beta-glycerolphosphate, and protease inhibitors 1 µg/µl leupeptin and aprotinin and 1 mM PMSF) by 20 strokes with a dounce homogenizer followed by an additional 20 strokes in a 1 ml syringe fitted with 21-gauge needle. Lysates were centrifuged at 3,000 rpm for 15 min to generate the post-nuclear supernatant (PNS). The PNS was then adjusted to 25% OptiPrep (Nycomed/Axis-Shield PoC.) with 50% OptiPrep in HB. The resulting mixture (2 ml in 25% OptiPrep) was placed at the bottom of an ultracentrifuge tube (14×89 mm) and was overlaid successively with 1 ml each of 20, 18.5, 16.5, 14.5, 12.5, 10.5, 8.5, 6.5 and 5% OptiPrep in cold HB. The gradients were centrifuged for 20 hr at 27,000 rpm at 4° C. in a SW41 rotor (Beckman Instruments). Fractions (500 µl) were collected from the top of the ultracentrifuge tubes and analyzed by Western blot analysis. P-APP, APP and BACE levels in each fraction were digitized by a Luminescent Image Analyzer (Fuji film) and expressed as a percentage of the sum of all of the fractions.

EXAMPLE 10

APP C-terminal Fragments Generated by β-Secretase Are Preferentially Phosphorylated on T668

Figure 19:
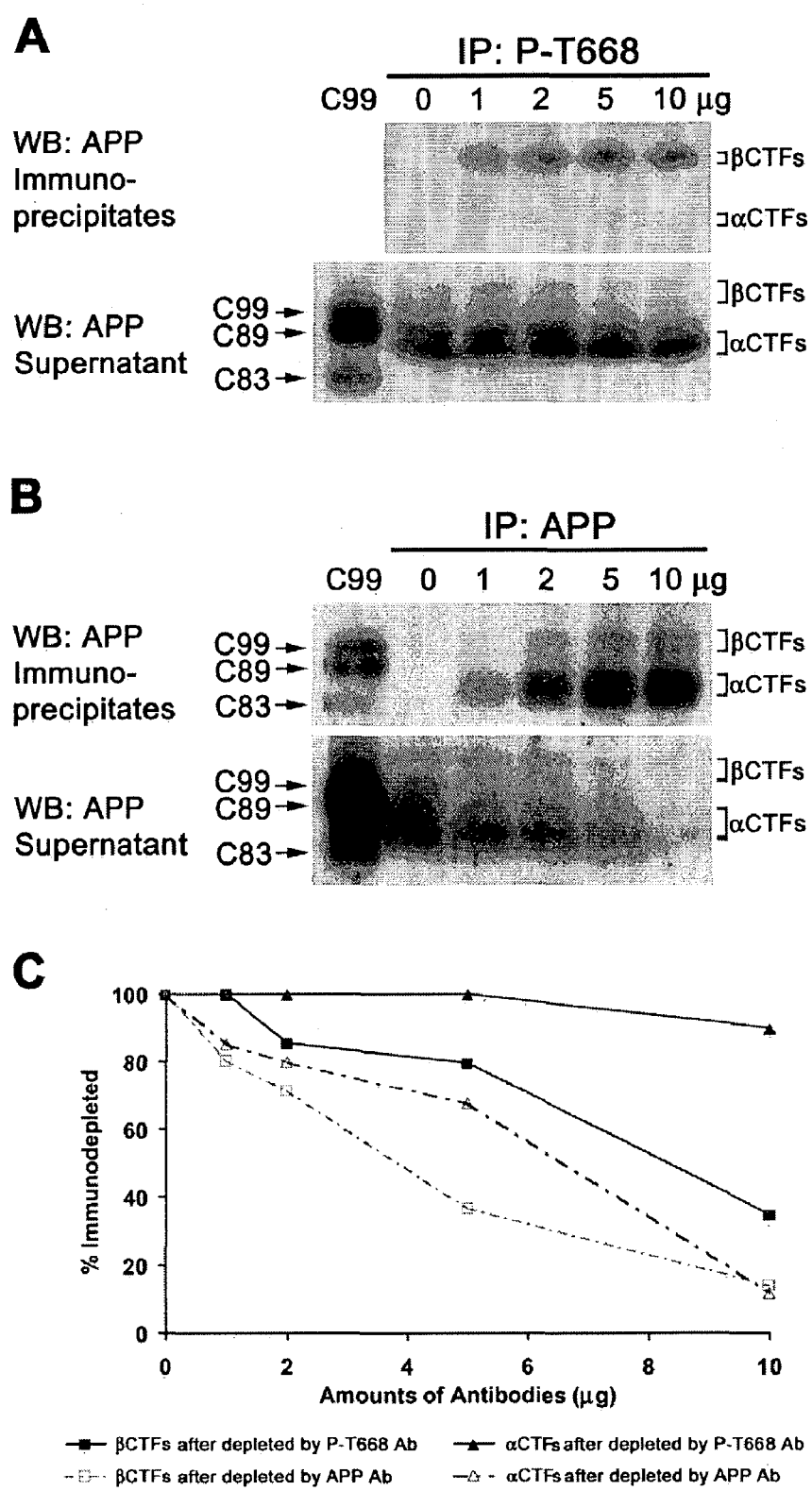
FIGS. 19A-19C depict preferential phosphorylation of βCTFs on T668. (A) Increasing amounts of P-T668 APP antibody was used to immunoprecipitate APP from lysates made from a 6-month old mouse brain. Western blot analysis using a pan APP antibody (C1/6.1) showed increasing levels of βCTFs were efficiently precipitated by P-T668 antibody whereas little αCTFs were brought down by the P-T668 antibody (top panel). Conversely, in the supernatants, a dose dependent decrease of βCTFs but not αCTFs was observed. (B) The C1/6.1 antibody efficiently immunoprecipitated both βCTFs and αCTFs. In supernatants, both βCTFs and αCTFs were completely removed using 10 µg of C1/6.1 antibody. (C) Quantification of the levels of βCTFs and αCTFs in supernatants from A and B reveals that βCTFs were efficiently removed from the brain lysates by the P-T668 antibodies.

To further determine the species of APP CTFs that is phosphorylated on T668 in vivo, immunodepletion experiments were performed. CTFs derived from CAD cells overexpressing C99, a β-secretase product of APP, were used as markers for identifying different CTF species (lane 1 of FIG. 19A, B). CTFs from mouse brain lysates generally showed slower mobility than those from C99 overexpressing CAD cells. Those CTFs with slower mobility than C99 from CAD cells were determined to be β-secretase products of APP (βCTFs) and those with faster mobility than C89 were determined to be the α-secretase product of APP (αCTFs). In these brain lysates, αCTFs were much more abundant then βCTFs (see lower panel of FIG. 19A, B). In 300 µg brain lysates, increasing amounts of the P-T668 antibody efficiently immunoprecipitated βCTFs, as recognized by the APP C-terminal antibody, in a dose dependent manner (FIG. 19A, upper panel). A corresponding dose-dependent decrease in βCTFs was observed in the supernatant of these immunoprecipitates (FIG. 19A, lower panel). The level of αCTFs in the supernatants only decreased slightly. When 10 µg of P-T668 antibody was used, about 60% of βCTFs were depleted, whereas only less than 10% of αCTFs were depleted from the brain lysate (FIG. 19C). As a control, the APP C-terminal antibody was used to immunoprecipitate APP CTFs from 300 µg of mouse brain lysates. This antibody efficiently removed both αCTFs and βCTFs from the lysates, as shown in the lower panel of FIG. 19B and FIG. 19C. These results indicate that the beta-secretase products of APP is preferentially phosphorylated on T668 in vivo, and that T-668 phosphorylation can facilitate APP cleavage by BACE1.

EXAMPLE 11

Effects of T668 Phosphorylation on Aβ Generation in Primary Cortical Neurons

Figure 20:
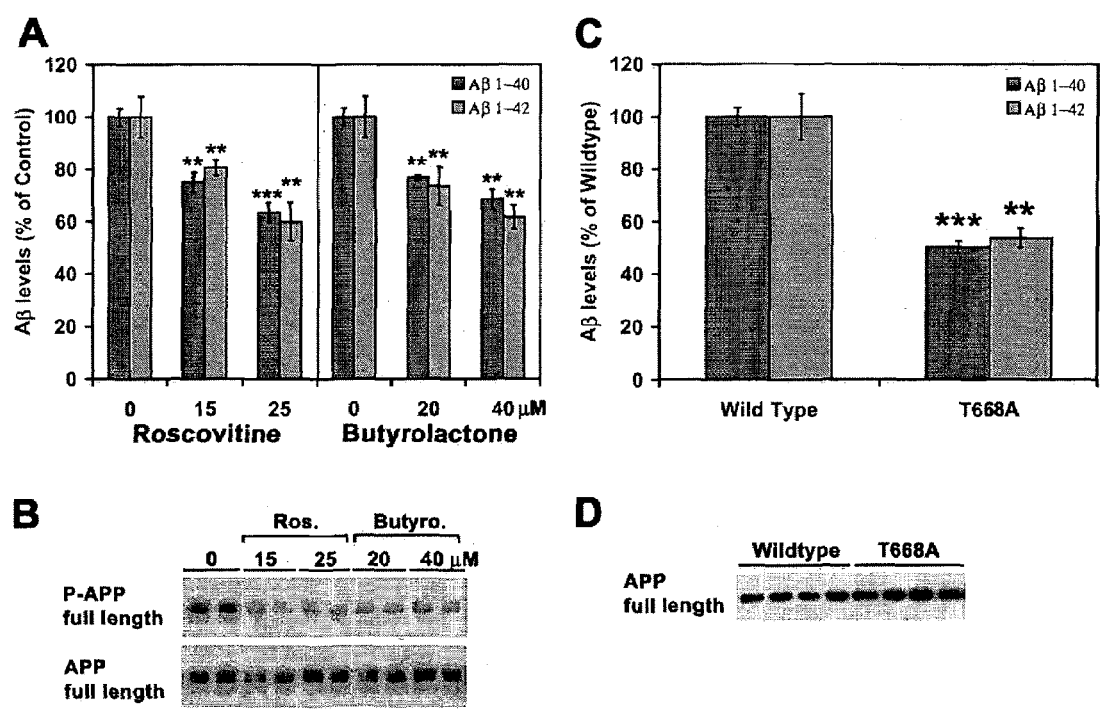
FIGS. 20A-20D depict reduced Aβ generation by APP T668 to alanine mutant and T668 kinase inhibitors in primary cortical neurons. (A) Inhibiting T668 phosphorylation by Cdk inhibitors lead to a decrease in Aβ secretion. Rat primary cortical neurons were infected with recombinant HSV expressing WT APP for 16 hours and than treated with indicated concentration of roscovitine or butyrolactone for 8 hours. The levels of secreted Aβ(1-40) or Aβ(1-42) were measured by sandwich ELISA and data was normalized against the untreated control (P=0.0051 for Aβ(1-40) and P=0.0071 for Aβ(1-42) under roscovitine treatment. P=0.0054 for Aβ(1-40) and P=0.0087 for Aβ(1-42) under butyrolactone treatment). (B) T668 phosphorylation levels of full length APP were detected by Western blot of cell lysates. (C) Aβ generation from rat primary cortical neurons expressing recombinant WT or T668A APP. Level of Aβ(1-40) and Aβ(1-42) secreted into the media from infected cultures was measured by sandwich ELISA. Markedly reduced Aβ(1-40) and Aβ(1-42) were secreted from neurons expressing the APP T668A mutant compared to those expressing WT APP (P<0.0001 for Aβ(1-40) and P=0.0027 for (Aβ 1-42)). The data was derived from three independent experiments with quadruple infections in each experiment. (D) Western blot analysis from 4 independent infections shows that the expression level of full length APP was comparable between WT and T668A mutant APP.
Figure 21:
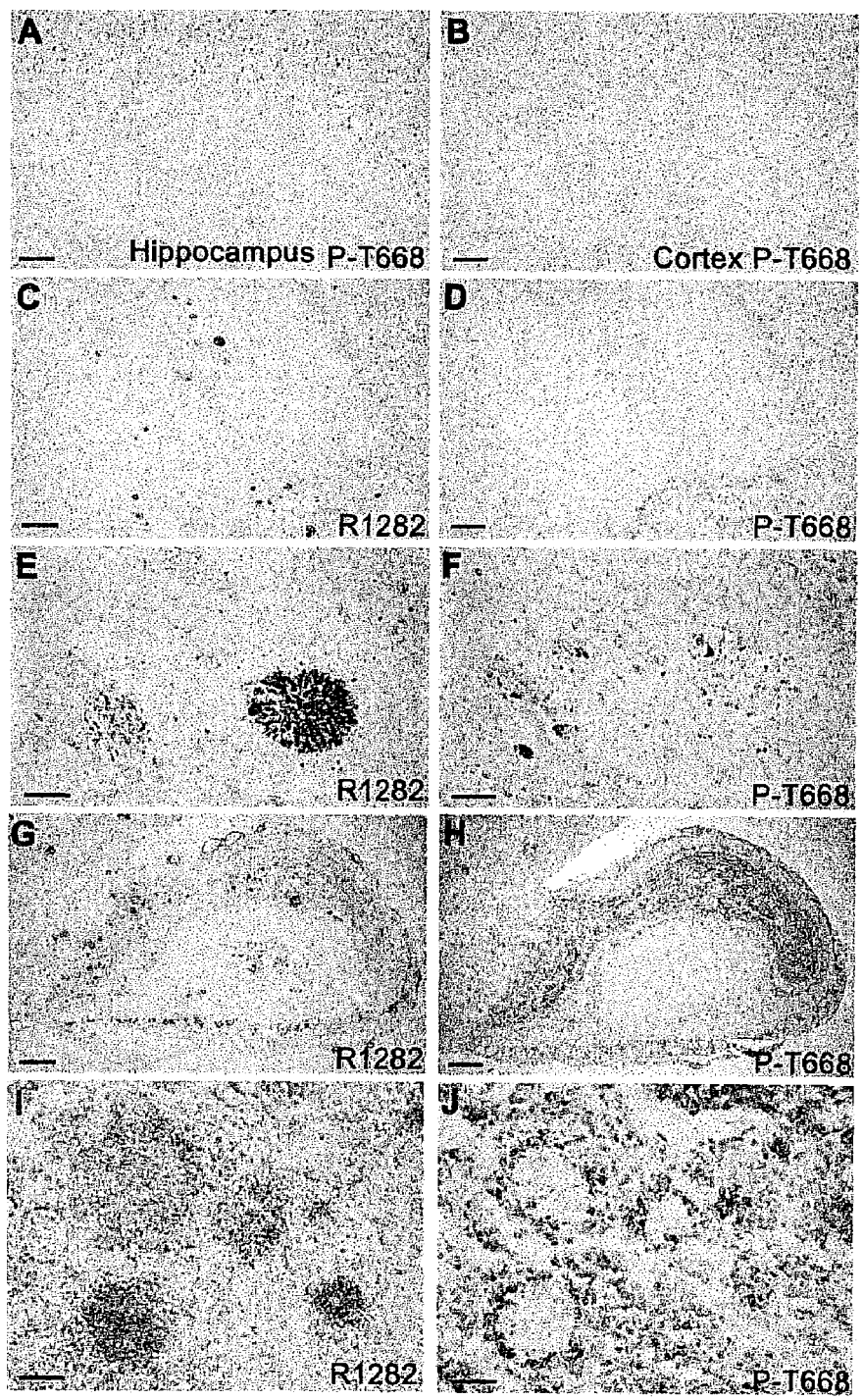
FIGS. 21A-21J depict staining of AD brain. (A) P-T668 staining was specific to hippocampus region of AD brain. (C-J) P-T668 antibody labeled dystrophic neurites that are closely associated with amyloid plaques in both AD brains and APP(Sw) Tg mice. (C, E) R1282 staining of AD hippocampal section showing the distribution of amyloid plaques. (D) Adjacent section stained with anti-P-T668 antibody. (F) 60× magnified view of AD hippocampal sections showing P-T668 positive dystrophic neurites surrounding the plaques. (G, I) Eighteen month-old APP(Sw) Tg mouse brain section stained with the R1282 antibody. Abundant extracellular amyloid plaques were labeled in the olfactory bulb. (H, J) Adjacent section stained with P-T668 antibody, which labeled dystrophic neurites closely associated with extracellular plaques. Scale bars: 250 μm (A-D, G, H) and 5 μm (E, F, I, J).

To elucidate whether T668 phosphorylation plays a role in Aβ generation, Aβ levels from the cultured media of neurons treated with the Cdk inhibitors roscovitine or butyrolactone were assessed. Since the levels of secreted Aβ from endogenous APP was too low to be detected, recombinant HSV was used to express WT APP in rat cortical neurons. Both roscovitine and butyrolactone treatments caused substantial decreases in T668 phosphorylation (FIG. 20B). Interestingly, levels of secreted Aβ(1-40) and Aβ(1-42) were significantly reduced by these inhibitors in a dose-dependent manner (P<0.05) (FIG. 20A). The reduction in Aβ secretion was not due to a decline in cell viability as determined by the MTT assay.

To directly test whether T668 phosphorylation is involved in the metabolism of APP, Aβ levels generated from neurons expressing WT APP versus T668A mutant APP were compared. Rat primary cortical neurons grown for 2 days in vitro were infected with HSV expressing either WT APP or the APP T668A mutant. The Aβ levels in the culture media were determined 20 hours post-infection. FIG. 20D shows that the expression levels of WT APP and T668A mutant APP were comparable in the cultures. However, Aβ(1-40) level in neuronal cultures expressing the T668A mutant was significantly reduced compared to neuronal cultures expressing WT APP (P<0.0001). The level of Aβ(1-42) in APP T668A cultures was also significantly reduced when compared to the WT APP cultures (P<0.05) (FIG. 20C). These results indicate that phosphorylation of T668 regulates APP processing and Aβ generation.

Generation of Recombinant Herpes Simplex Virus

WT and T668A APP coding sequence were subcloned in to a replication-defective herpes simplex virus vector pHSVPrpUC. The resultant recombinant plasmid was packaged into virus particles in the packaging line 2-2 using the protocol previously described (Lim et al. (1996) *Biotechniques* 20:460). The virus was then purified on a sucrose gradient, pelleted and resuspended in 10% sucrose and the titer of the recombinant virus was determined.

EXAMPLE 12

Generation of Inducible Tg Mice Overexpressing p25 in the Postnatal Forebrain

The tTA system was used to generate bi-Tg mice that inducibly overexpressed human p25 under the control of the CamKII promoter, which drives high transgene expression in the forebrain (Mayford et al. (1996) *Science* 274:1678). In the presence of the tetracycline derivative doxycycline, expression of the p25 transgene was inhibited. All mice in this study were conceived and raised in the presence of doxycycline for at least 4-6 weeks postnatally before induction of p25 to prevent any potential developmental consequences from the expression of p25.

p25 was C-terminally tagged with either GFP or C-myc. Expression of these constructs in cultured cells showed that both p25-GFP and p25-C-myc behaved similarly in that their subcellular localization and ability to activate Cdk5 was identical to that of untagged p25. Independent Tg mouse lines expressing p25-GFP and p25-C-myc were investigated and it was determined that both Tg mouse lines had similar expression profiles and phenotypes. These cumulative results indicate that the epitope tags themselves neither interfered with the biological activity of p25 nor were they responsible for the phenotypes observed.

Figure 35:
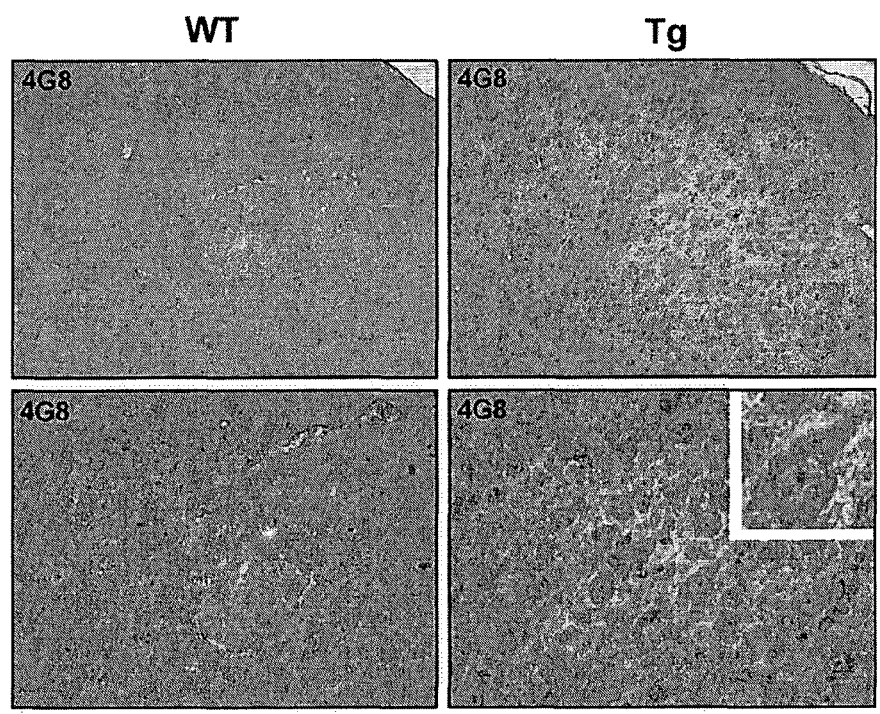
Figure 35:
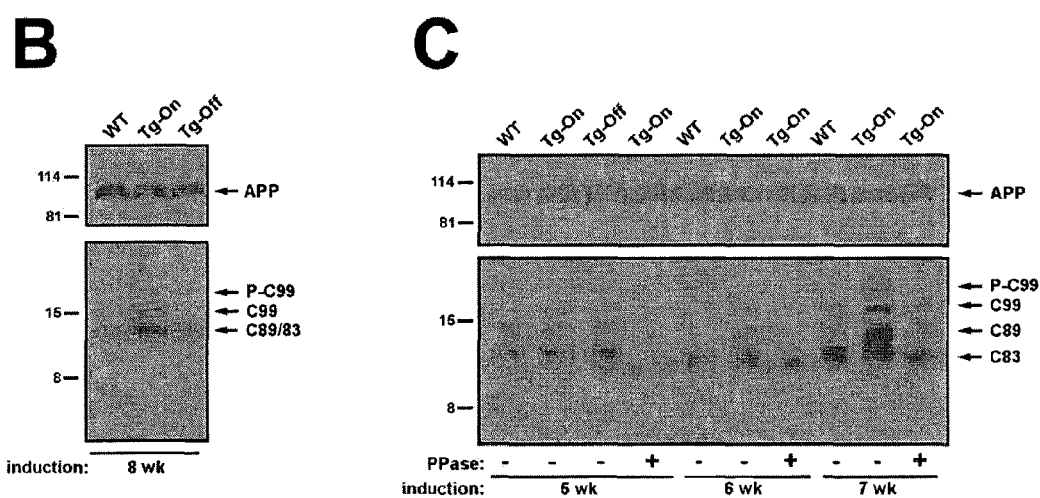

In forebrains of p25-GFP Tg mice not exposed to doxycycline (i.e., induced), robust p25 transgene expression was detected as compared to forebrains of WT mice and p25 Tg mice exposed to doxycycline (i.e., non-induced) (FIG. 26A). Cdk5, p35, p39, and β-actin expression were similar in all mice (FIG. 26A). However, Cdk5 activity was dysregulated in the induced Tg mice. Upon dissection of various brain regions from control and induced Tg mice, immunoblot analysis revealed substantial p25 expression and induction in the cerebral cortex, hippocampus, and striatum, with minimal p25 expression in the cerebellum of induced Tg mice (FIG. 26B). Either low or no p25 expression was found in non-induced Tg and WT mice, respectively (FIG. 26B). Similar results were also found in the p25-C-myc Tg mouse line (FIG. 33A, 33B). The subcellular localization of the p25-GFP transgene was determined by immunostaining coronal brain sections of control and Tg mice with anti-GFP to distinguish p25 from endogenous p35. It was determined that p25 displayed a somatodendritic staining pattern in neurons of the cerebral cortex and the hippocampus (FIG. 26C). Unlike the localization of p35 (Delalle et al. (1997) *J Neurocytol*. 26:283; Tomizawa (1996) *Neurosci*. 74:519), p25 did not appear to label any axonal fiber tracts in the forebrain. C99, the BACE1 cleavage product of APP, was drastically upregulated in the Tg mice compared to WT mice (FIG. 35).

Generation of p25 Tg Mice

The construction of a p25 plasmid vector was previously described (Patrick et al. (1999) *Nature* 402:615). Human p25 was C-terminally tagged with either GFP or C-myc, subcloned into the vector pTet-Splice (Clontech), and verified by sequencing. To generate the microinjected construct, the plasmid vectors were linearized with XmnI and digested with XhoI/NotI to release TetO-p25-GFP or TetO-p25-myc. Each p25 transgene was microinjected into fertilized mouse eggs and reimplanted into pseudopregnant females. Founders were screened by Southern blot and PCR analysis. Germline founders were crossed with CaMKII-tTA Tg mice (Mayford et al. (1996) *Science* 274:1678). All mice were backcrossed to obtain a homogeneous C57BL/6J background. Mice for analysis were derived from heterozygote crosses to ensure all genotypes in each litter, which were obtained in a Mendelian manner. All mice were conceived (throughout gestation) and raised in the presence of doxycycline (up to 1 mg/g in food, changed twice a week) (Bio-Serv, Frenchtown, N.J.) for at least 4-6 weeks postnatal before induction of p25 (by removal of doxycycline) to prevent any potential developmental consequences from the expression of p25. Littermate and same sex mice were used for comparison whenever possible.

EXAMPLE 13

Neurodegeneration in p25 Tg Mice

Figure 27:
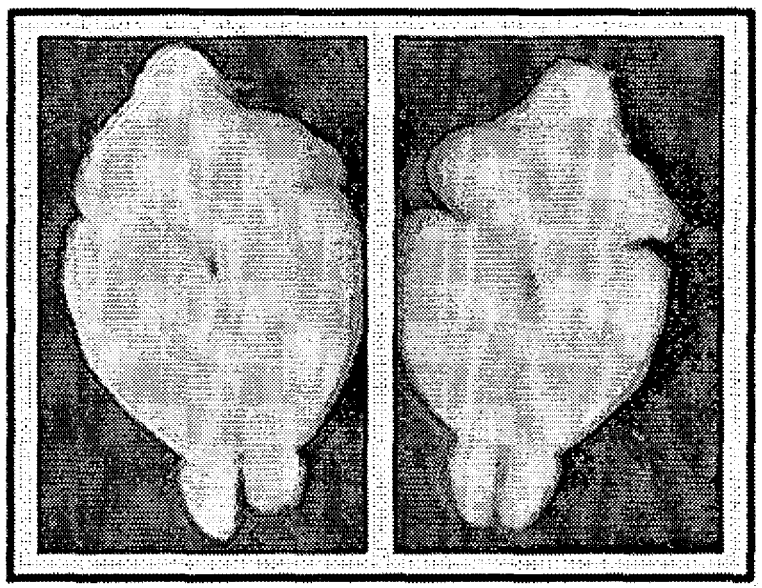
Figure 27:
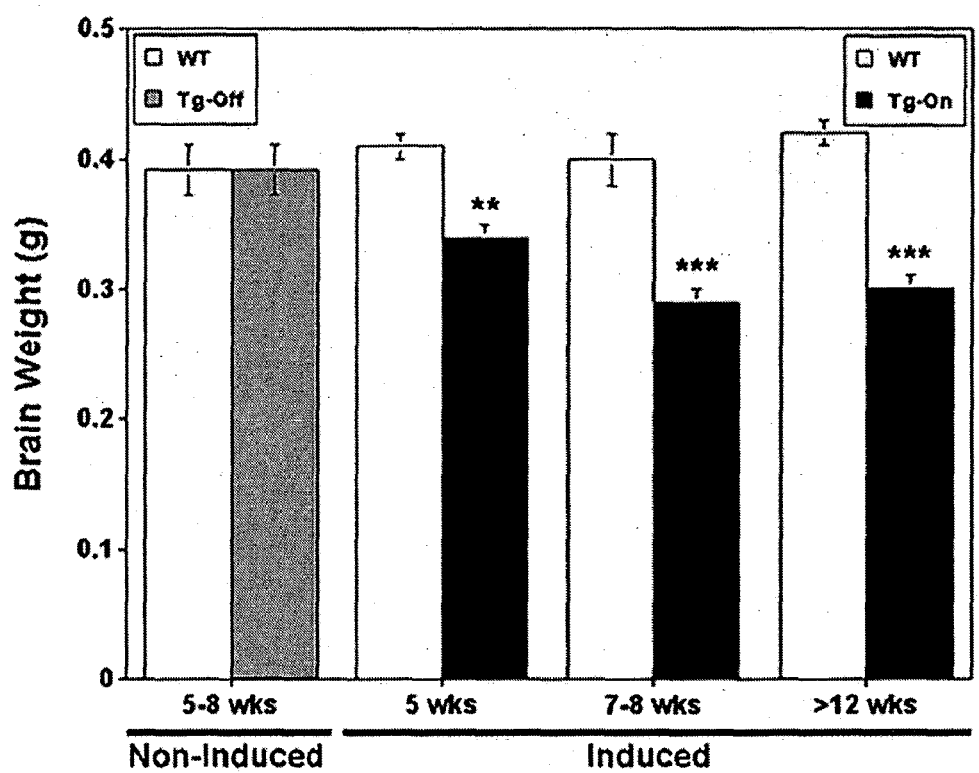
Figure 27:
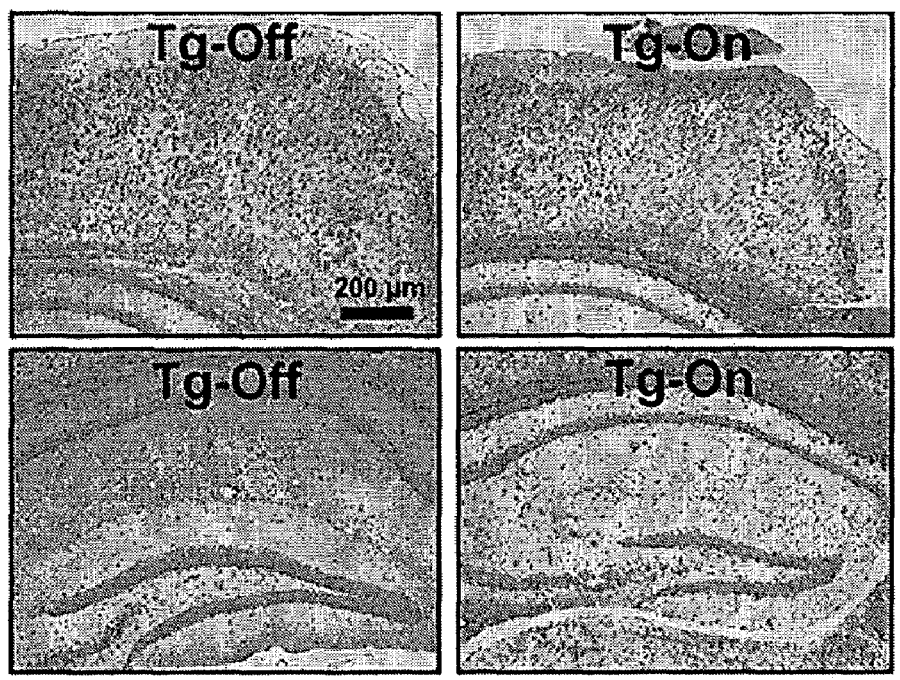
Figure 27:
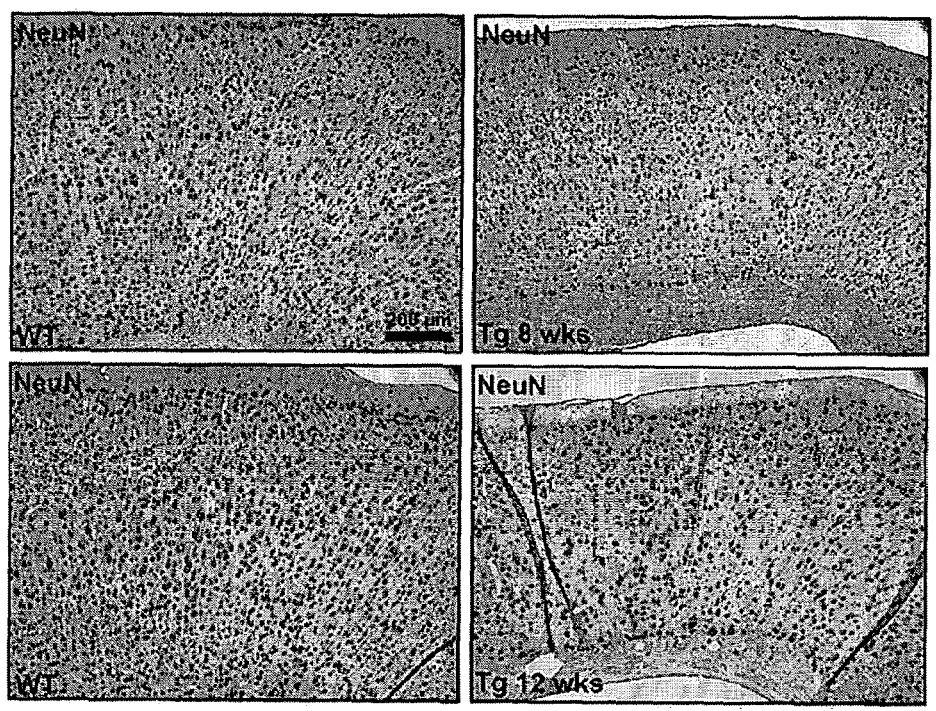
Figure 27:
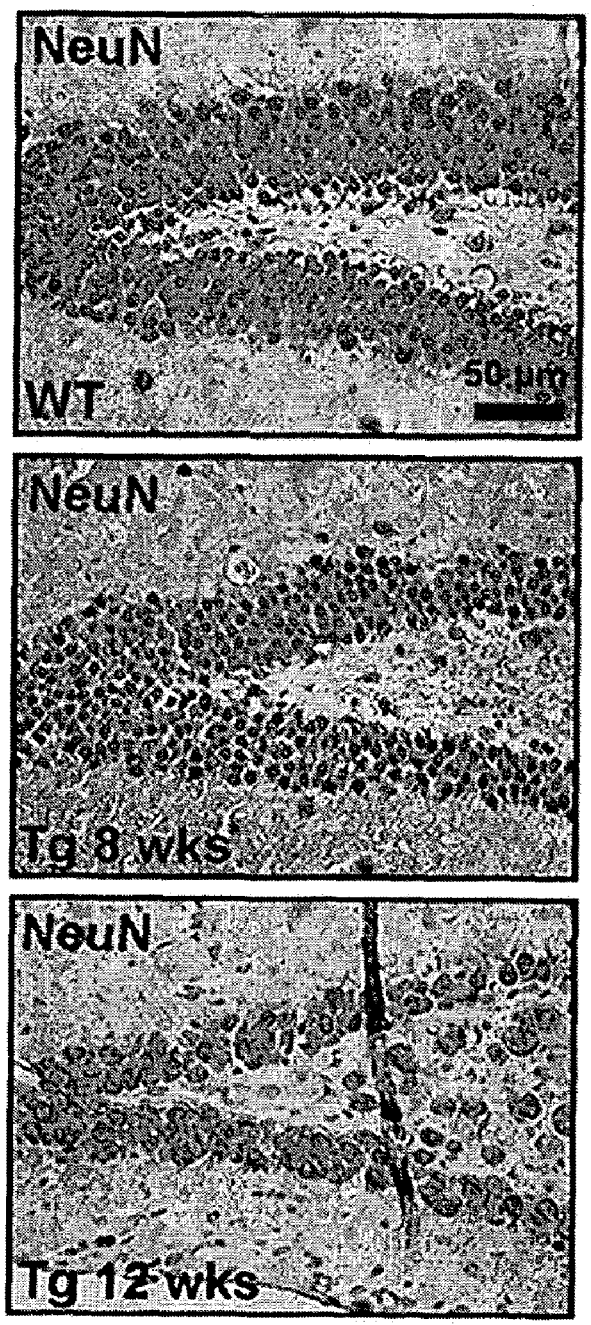
Figure 27:
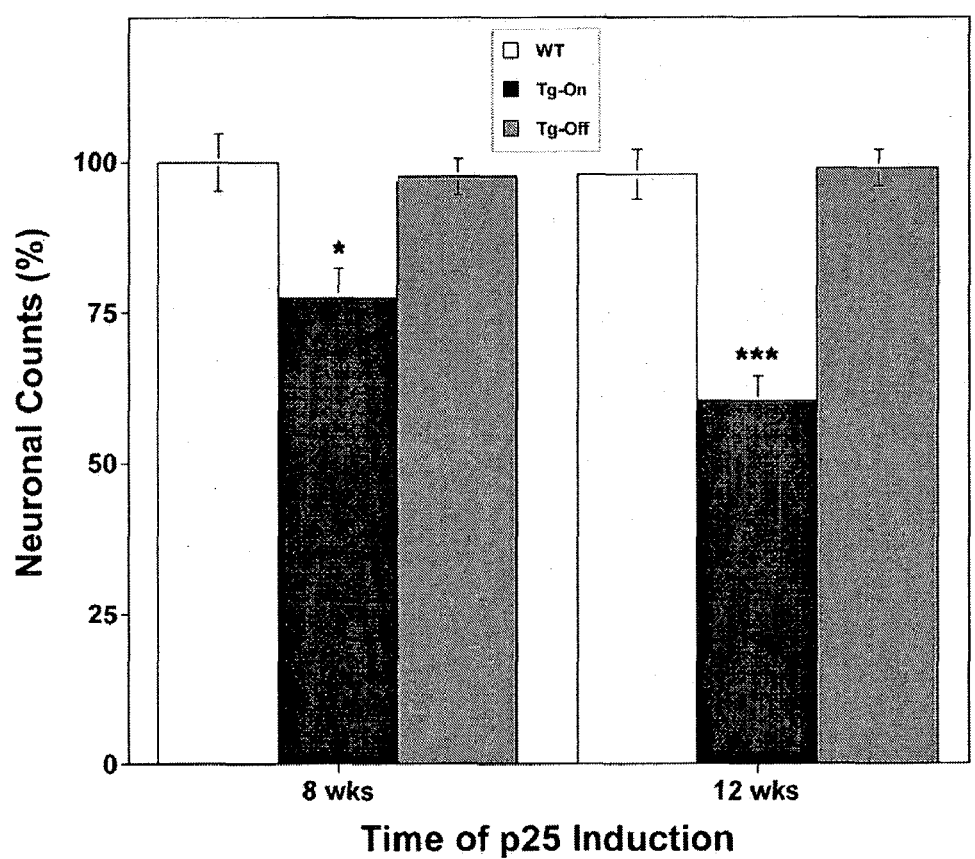
Figure 27:
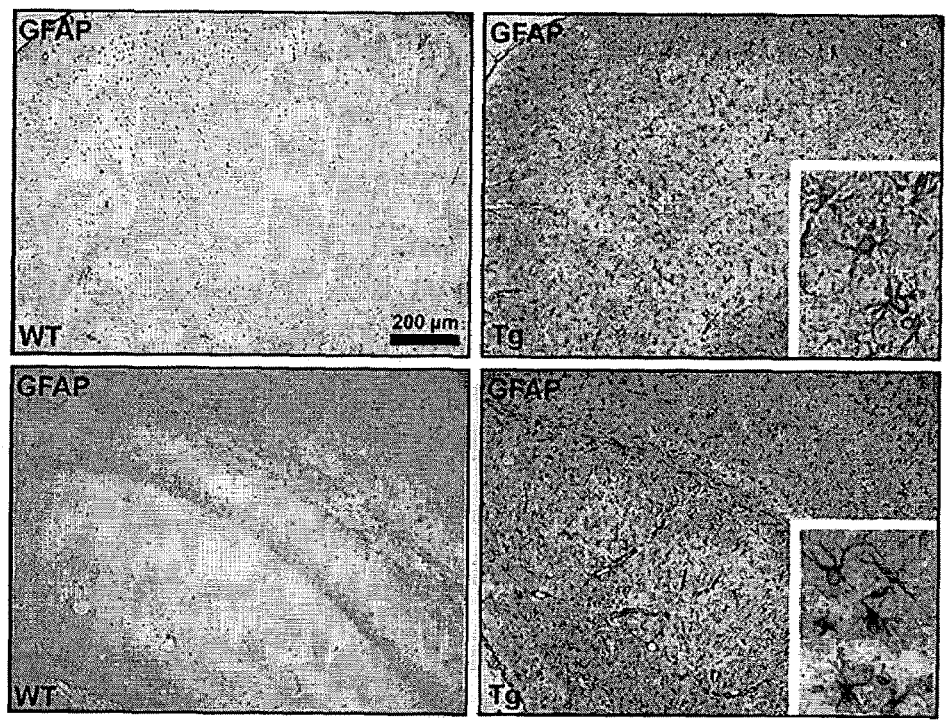
Figure 27:
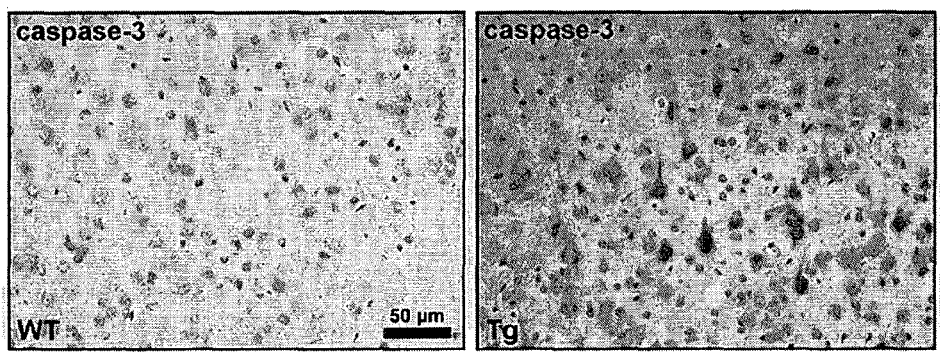
Figure 27:
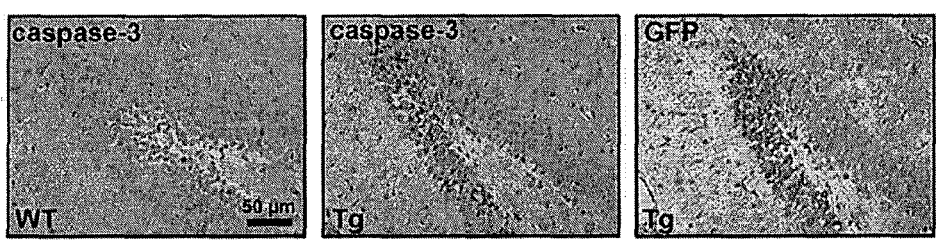
Figure 27:
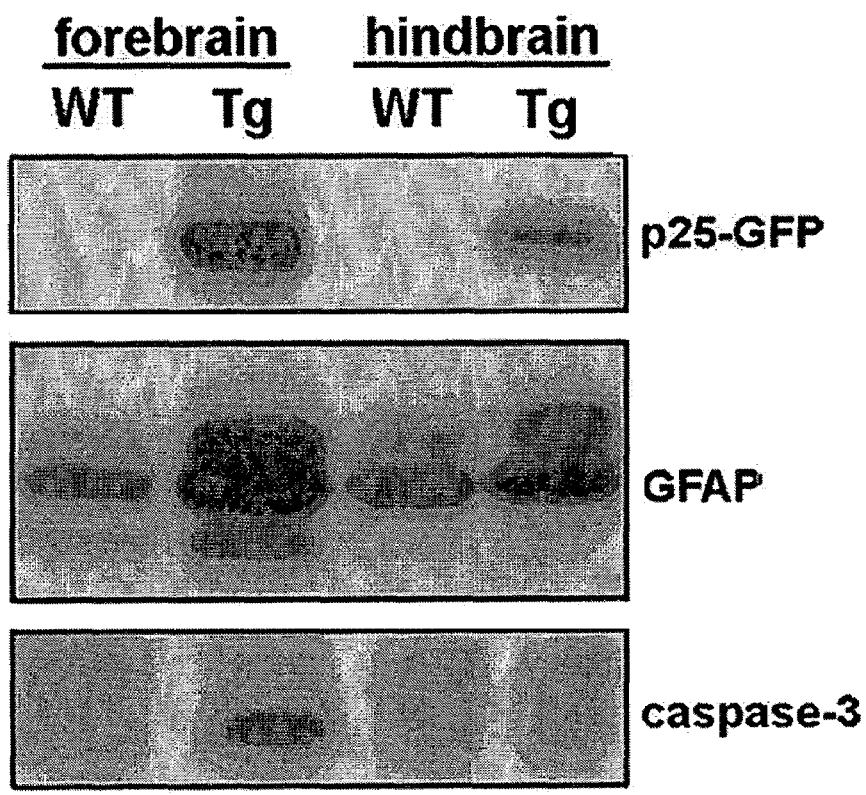

Induced p25 Tg mice compared to control littermates exhibited a slightly decreased body weight with no other obvious outward differences. Upon gross inspection of brains from control and p25 Tg mice, a significant decrease in forebrain mass in Tg mice was found (FIG. 27A). In addition, a progressive decrease in brain weight was detected in Tg mice induced for various periods of time (FIG. 27B, FIG. 33C). As compared to control mice, Tg mice induced for 5 weeks had a 15-20% decrease in brain weight; after 7-8 weeks or >12 weeks of p25 induction, there was a 30% decrease in brain weight.

The histology of non-induced and induced Tg animals was investigated. Nissl-stained brain sections from non-induced and 12 week induced Tg littermates revealed considerable decreases in the thickness and neuronal density within the cerebral cortex and hippocampus of induced Tg mice (FIG. 27C). To further assess if there was neuronal loss in these brain regions of Tg mice, brain sections from WT and Tg mice that were induced or non-induced for 8 or 12 weeks were stained with the neuronal-specific markers, NeuN and HuC/D. Progressive neuronal loss was found in both the cerebral cortex (FIG. 27D) and hippocampus (FIG. 27E) of Tg mice. Further quantification of these results (FIG. 27F, FIG. 33D) revealed that, as compared to control mice, Tg mice induced for 8 or 12 weeks exhibited a 25% or 40% decrease in cortical neuronal density, respectively. The neuronal density was indistinguishable between WT and non-induced Tg mice (FIG. 27F), indicating that the neuropathology observed in p25 Tg mice was due to degeneration in adulthood caused by postnatal p25 induction and was not attributed to minimal p25 expression prior to induction.

Reactive astrogliosis often accompanies neuronal loss and serves as a hallmark lesion for neurodegeneration. By using a marker of reactive astrogliosis, a remarkable increase in GFAP-immunoreactive radial and stellate-shaped astrocytes was quite evident throughout the cortex and hippocampus of p25 Tg mice (FIG. 27G). Certain neurons were also positive for active caspase-3, one of the key executioners of apoptosis, in the cerebral cortex of Tg mice (FIG. 27H). In the dentate gyrus of the hippocampus, there was an overlap among those neurons that expressed p25 and were positive for active caspase-3 (FIG. 27I). Neither active caspase-3 nor GFP staining was detected in control mice. These immunohistochemical results were further corroborated by immunoblot analysis. Increases in both GFAP and active caspase-3 immunoreactivities were found in forebrain, but not hindbrain, lysates from Tg mice (FIG. 27J). Together, these results indicate that the age-dependent neuronal loss, accompanied by extensive astrogliosis and caspase-3 activation, occurs with a selective pattern of degeneration that correlates with p25 expression in Tg mice.

Immunohistochemical and Histochemical Studies

Mice were anesthetized with avertin and intracardially perfused with PBS, followed by 4% paraformadehyde. Representative 5 μm thick paraffin coronal mouse brain sections were deparaffinized and rehydrated. For immunohistochemistry, sections were incubated with methanol peroxidase for 10 min to quench endogenous peroxidase activity. Antigen retrieval was performed by microwave irradiation in Antigen Retrieval Citrate Buffer (BioGenex, San Ramon, Calif.). For certain immunostains, 88% formic acid treatment at RT for 10 min was also performed. After blocking with 10% goat serum, the sections were incubated with primary antibodies overnight at 4° C. Bound antibodies were detected by biotinylated-coupled secondary antibodies and standard streptavidin-biotin-peroxidase methods (Vector Laboratories, Burlingame, Calif.). The following antibodies were used for immunostaining. GFP (1:1000) and HuC/D (10 μg/mL) were from Molecular Probes (Eugene, Oreg.); NeuN (1:500) was from Chemicon International (Temecula, Calif.); GFAP (1:500) was from Sigma (Saint Louis, Mo.); cleaved caspase-3 Asp175 (1:50) was from Cell Signaling Technology (Beverly, Mass.); AT8 (1:100) was from Innogenetics (Belgium); and PHF1 (1:100) was from P. Davies. Modified Gallyas and improved Thioflavin-S stains were performed as previously described (Sun et al. (2002) *J. Histochem. Cytochem.* 50:463.

Neuronal Counts

To quantitate the neuronal density among control (WT and non-induced Tg) and 8 and 12 week induced Tg mice (n=12), comparable coronal brain sections derived from the septo-striatal, septo-diencephalic, or the caudal diencephalon regions of the cerebral cortex were immunostained with neuronal markers, HuC/D or NeuN. No difference was found between these two stainings. The number of neurons in a total of six comparable areas (average of two to three adjacent fields for each region) was blindly counted by four independent investigators. Neuronal counts for the Tg-On and Tg-Off mice were normalized to WT mice (100%). The results were qualitatively confirmed by Nissl staining.

EXAMPLE 14

Increased Cdk5 Activity and Differential Substrate Phosphorylation in p25 Tg Mice In order to determine if neurodegeneration was triggered by increased Cdk5 activity in p25 Tg mice, two different p35 antibodies were used to immunoprecipitate the active Cdk5 complex in forebrains of WT, non-induced and 5 week induced Tg mice. Using the C19 antibody recognizing the C-termini of p35 and p25, a significant increase (2.3±0.1 fold) in kinase activity was observed in induced Tg mice as compared to WT mice (FIG. 28A). No differences were found between WT and non-induced Tg mice. When the N20 antibody, which recognizes the N-terminus of p35 not present in p25, was used, no significant differences were observed among control and Tg mice (FIG. 28A). These results demonstrate that p25 Tg mice conditionally express p25 at levels several fold higher than endogenous p35, which results in elevated p25/Cdk5 activity without affecting endogenous p35/Cdk5 activity.

Another means used to assess Cdk5 activity in p25 Tg mice was to examine the phosphorylation status of known Cdk5 substrates. Immunoblot analysis using SMI34, an antibody recognizing phosphorylated neurofilament protein (NF), showed a marked increase in NF phosphorylation in Tg mice as compared to WT mice. Conversely, there was a decrease in the amount of unphosphorylated NF in Tg mice when immunoblotted with SMI32, which recognizes unphosphorylated NF (FIG. 28B). In Tg mice, T668 phosphorylation of APP was considerably higher than in control littermates (FIG. 28B). The p42/44 MAP kinases were activated and increased phosphorylation of FAK at Y397 was observed in p25 Tg mice (FIGS. 34A-B). GSK-3β activity was not upregulated in p25 Tg mice (FIG. 34C).

Other Cdk5 substrates are known to be involved in various physiological events. Nudel is a Lis1 and cytoplasmic dynein binding protein that can be phosphorylated by Cdk5 at multiple sites (Niethammer et al. (2000) *Neuron* 28:697; Sasaki et al. (2000) *Neuron* 28:681). mDab1 is a key component in the Reelin signaling pathway essential for migration and positioning of neurons and was shown to be phosphorylated by Cdk5 at S496 (Keshvara et al. (2002) *J. Neurosci.* 22:4869). PSD95 is a post-synaptic scaffolding protein important for the assembly of signaling and cytoskeletal components. PSD95 is phosphorylated by Cdk5 on T19 and S25 (Yang and Hinds (2003) *Mol. Cell* 11:1163). In Western blot analyses of forebrain lysates using phospho-epitope specific antibodies against Cdk5 phosphorylation sites of Nudel, mDab1, and PSD95, no increase in phosphorylation of these proteins was observed (FIG. 28C). Phosphorylation at these sites was abolished or diminished in p35 and Cdk5-deficient mice (Keshvara et al. (2002) *J. Neurosci.* 22:4869; Ko et al. (2001) *J. Neurosci.* 21:6758). The differential phosphorylation activities toward these sets of substrates indicated that p25 exhibits altered substrate specificity from that of p35; that is, p25/Cdk5 and p35/Cdk5 preferentially phosphorylate pathological and physiological Cdk5 substrates, respectively.

Cdk5 Kinase Assay

Mice were sacrificed by cervical dislocation. Brain tissues were dissected and homogenized in radioimmunoprecipitation (RIPA) buffer (50 mM Tris pH 8.0, 150 mM NaCl, 1% Nonidet P40 (NP40), 0.5% sodium deoxycholate, 0.1% SDS) containing protease and phosphatase inhibitors (1 μg/mL aprotinin, 1 μg/mL leupeptin, 1 μg/mL pepstatin, 10 mM NaF, 1 mM 1,4-dithio-DL-threitol (DTT,) 2 mM NaVO$_3$, 1 mM phenyl methyl sulfonyl fluoride (PMSF), 50 mM β-glycerolphosphate, and 2 mM Na$_4$P$_2$O$_7$). The homogenates were rocked at 4° C. for 30 min. After centrifugation, the supernatants were collected to obtain brain lysates. Using a Bio-Rad Laboratories (Hercules, Calif.) protein assay, the protein concentrations of brain lysates were determined. Brain lysates (500 μg) were incubated with p35 (1 μg) antibodies from Santa Cruz Biotechnology (Santa Cruz, Calif.) for 1 hour at 4° C. and the active Cdk5 complex was isolated by protein A-sepharose (Amersham Pharmacia Biotech, Uppsala, Sweden) for 1 hour at 4° C. The immunocomplex was subjected to a Cdk5 kinase assay using histone H1 peptide (PKTPAKAKKL) (SEQ ID NO:9) as a substrate. Once a reaction mixture (30 μL), containing 20 mM MOPS (pH 7.2), 5 mM MgCl$_2$, 500 μM H1 peptide, 100 μM ATP, and 2.5 μCi γ-$^{32}$ATP, was added, the reaction continued for 20 min at RT. The reaction was stopped by placing samples on ice for 5 min. Supernatants were spotted on P-cellulose discs (Gibco Life Technologies, Inc., Galthersburg, Md.), washed in 0.3% phosphoric acid, and counted in a liquid scintillation counter.

Immunoblot Analysis

Brain lysates were prepared as described above. Lysates were either used freshly, or aliquoted, frozen in liquid nitrogen, and stored at −80° C. until use. Equal amounts of brain lysates were subjected to SDS-PAGE and transferred to polyvinylidene fluoride (PVDF) membranes (Millipore Corporation, Bedford, Mass.). After blocking with 5% milk, the membranes were probed with primary antibodies. Bound antibodies were detected by horseradish peroxidase (HRP)-coupled secondary antibodies (Amersham Biosciences, Buckinghamshire, England) and enhanced chemiluminscence (Perkin Elmer Life Sciences, Inc, Boston, Mass.). The following antibodies were used for immunoblot analysis: monoclonal DC17 (Cdk5) (1:10), polyclonal antibodies p35, p39, P-NUDEL (S231), P-mDab1(S491), P-PSD95 (S19/S25), and P-APP (T668) were generated in the L.H. Tsai lab; α-actin, β-tubulin, GFAP were from Sigma (Saint Louis, Mo.); PSD95, cleaved caspase-3 Asp175 (1:500), p42/44, P-p42/44 (T202/Y204), and P-GSK-3β (S9) were from Cell Signaling Technology (Beverly, Mass.); FAK, JNK1 and P-JNK (T183/Y185) were from Santa Cruz Technology (Santa Cruz, Calif.); P-GSK-3a/β (Y279/216) and tau 5 were from Biosource International (Camarillo, Calif.); β-catenin was from Becton, Dickinson, and Company (Franklin Lakes, N.J.); tau 1 (1:2000) was from Chemicon International (Temecula, Calif.); AT8 was from Innogenetics (Belgium); and PHF1 was from P. Davies. All primary antibodies were diluted 1:1000 unless otherwise noted.

EXAMPLE 15

Tau Hyperphosphorylation and Microtubule Polymerization in p25 Tg Mice

Figure 29:
Figure 29:
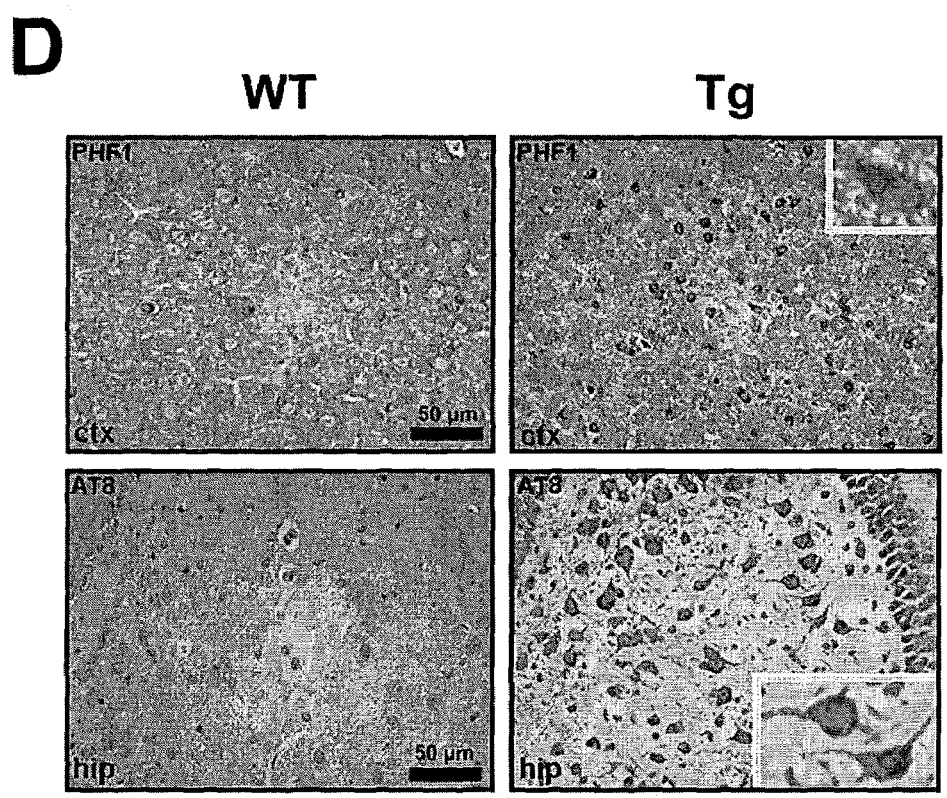

Whether increased p25/Cdk5 activity affects endogenous tau phosphorylation in p25 Tg mice was examined. Western blot analysis of WT and Tg forebrain lysates showed that total levels of tau were similar (FIG. 29A). Increased phosphorylation of tau at several epitopes in Tg mice was detected by immunoblotting with the antibodies AT8 (FIG. 29B) and PHF1 (FIG. 29C), which recognize phospho-tau epitopes S202/T205 and S396/S404, respectively. Immunohistochemical analysis using these phospho-tau antibodies identified irregular, cytoplasmic dense tau inclusions within neurons of the cerebral cortex and pyramidal cells of the hippocampus of Tg mice that was not present in control mice (FIG. 29D and FIG. 33E). Increased phosphorylation of tau was also observed in transfected cultured neurons.

To obtain a more comprehensive picture of the tau phosphorylation profile in p25 Tg mice, tandem mass spectrometry was performed on heat-stable soluble tau preparations derived from WT and Tg mice. Although phospho-tau peptides were detected in both WT and Tg mice, the phospho-tau peptide profiles obtained were different between the samples, with only a few regions of overlap (FIG. 29E). These results indicate that the phosphorylation pattern of tau is significantly changed in Tg mice. A total of six phosphorylated tau sites in WT (T111, T175, T176, T181, S185, and T231) and 15 phosphorylated tau sites in Tg mice (T175, T176, S178, S195, S198, S199, S202, T205, T217, T220, S235, S239, S396, S400, and T403) were identified (Table 4). Tau peptides containing phosphorylated S202, T205, and T396 were found only in Tg mice, supporting the results using AT8 and PHF1 antibodies (FIG. 29B-29D). The presence of other tau peptides containing phosphorylated proline-directed and non-proline directed phosphorylation sites were also detected in Tg mice.

To determine if the ability of tau to efficiently bind microtubules was compromised in p25 Tg mice, a microtubule polymerization assay was performed. Over time, tubulin alone, without tau-containing lysates, did not efficiently polymerize into microtubules (FIG. 29F). When heat-stable tau preparations derived from WT forebrains were added to tubulin, efficient microtubule polymerization was observed (FIG. 29F); however, when similar tau preparations derived from Tg mice were used, the mice were compromised in their ability to form stable microtubules (FIG. 29F).

TABLE 4

Summary of mouse phospho-tau peptides detected in tandem mass spectrometry. Phosphorylated residues are labeled in larger font size. The numbering of the mouse tau peptide sequences are based on human tau with 441 amino acids

| Peptides | Sequences | Phosphorylations |
|---|---|---|
| WT | | |
| 103–130 | EEAGIGDTPSLEDEAAGHVTQARMVSK (SEQ ID NO:10) | Thr111 |

TABLE 4-continued

Summary of mouse phospho-tau peptides detected in tandem mass spectrometry. Phosphorylated residues are labeled in larger font size. The numbering of the mouse tau peptide sequences are based on human tau with 441 amino acids

| Peptides | Sequences | Phosphorylations |
|---|---|---|
| 171–194 | IPAKTTPSPKTPPGSGEPPKSGER (SEQ ID NO:11) | Thr175, Thr176, Thr181, Ser185 |
| 226–242 | VAVVRTPPKSPSASKSR (SEQ ID NO:12) | Thr231 |
| p25Tg | | |
| 171–180 | IPAKTTPSPK (SEQ ID NO:13) | Thr175, Thr176, Ser178 |
| 195–224 | SGYSSPGSPGTPGSRSRTPSLPTPPTREPK (SEQ ID NO:14) | Ser195, Ser198, Ser199, Ser202, Thr205 |
| 210–221 | SRTPSLPTPPTR (SEQ ID NO:15) | Thr217, Thr220 |
| 210–224 | SRTPSLPTPPTREPK (SEQ ID NO:16) | Thr217, Thr220 |
| 212–221 | TPSLPTPPTR (SEQ ID NO:17) | Thr217 |
| 235–257 | SPSASKSRLQTAPVPMPDLKNVR (SEQ ID NO:18) | Ser235, Ser239 |
| 386–406 | TDHGAEIVYKSPVVSGDTSPR (SEQ ID NO:19) | Ser396, Ser400, Thr403 |

Preparation of Tau Peptide Samples and Mass Spectrometry Analysis

Soluble tau samples used in mass spectrometric analysis were prepared using a heat treatment protocol. Mouse forebrain lysates were prepared as described above. After centrifugation at 13,000×g for 10 min, lysates were collected and incubated at 90° C. for 5 min. Protein aggregates were removed by centrifugation. Heat-stable tau proteins were incubated with trypsin (50:1) overnight at 37° C. Tau tryptic peptides were further purified by ZipTipC18 (Millipore Corporation, Boston, Mass.) and analyzed in an LC-MS/MS system, which was equipped with a Waters HPLC and Micromass Q-TOF Micro mass spectrometer (Micromass MS Technologies, Mass.). For liquid chromatography, a PicoFrit C18 column (New Objective, Mass.) was used in separation and electrospray. Mobile phase A contained 5% acetonitrile and 0.1% formic acid; mobile phase B contained 95% acetonitrile and 0.1% formic acid. The separation used a gradient of 0.4% B/min. The flow rate was 1 µL/min. A full-scan from 400-2000 m/z with a 1 sec period was used. MS/MS mode was switched on the first three strongest ions present in the previous full-scan spectrum. Collision energy used a Micromass charged-state protocol. All collision-induced dissociation (CID) spectra were analyzed in a Mascot server with a microtubule-associated protein tau database. Mass tolerance was set at 150 ppm in MS ions and 0.5 Dalton in MS/MS ions. CID spectra related to phosphorylation were manually examined to ensure that daughter ions were sufficient to assign phosphorylation sites.

Microtubule Polymerization Assay

Lyophilized tubulin from Cytoskeleton (Denver, Colo.) was reconstituted in G-PEM buffer, as described by the manufacturer, at 4° C. and centrifuged to remove tubulin aggregates. To perform the in vitro tubulin assembly assay, 0.5 ug/ul of tubulin was added to 0.2 ug/ul of proteins derived from mouse forebrain heat-stable tau preparations, as described, in G-PEM buffer. The assembly of tubulin with or without heat-stable tau preparations was monitored once the temperature reached RT. Similar amounts of tau protein in the heat-stable preparations was confirmed by Western analysis using tau-5 antibody from Biosource International (Camarillo, Calif.). The turbidity measurement of tubulin polymerization was monitored in a Beckman DU640 Spectrophotometer at 350 nm.

EXAMPLE 16

Tau Aggregation in p25 Tg Mice

Figure 30:
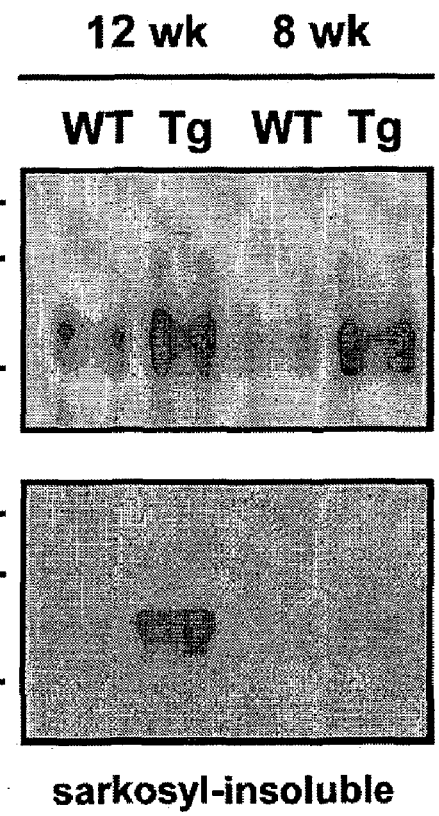
Figure 30:
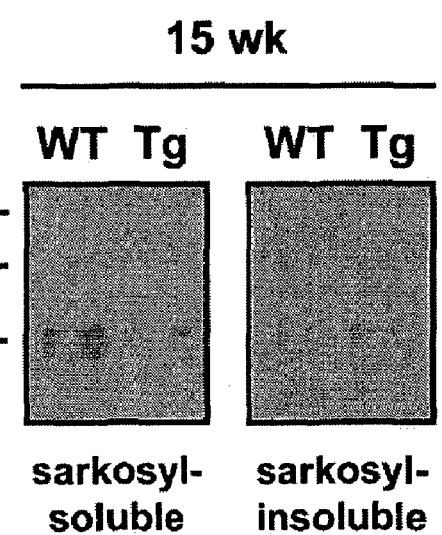
Figure 30:
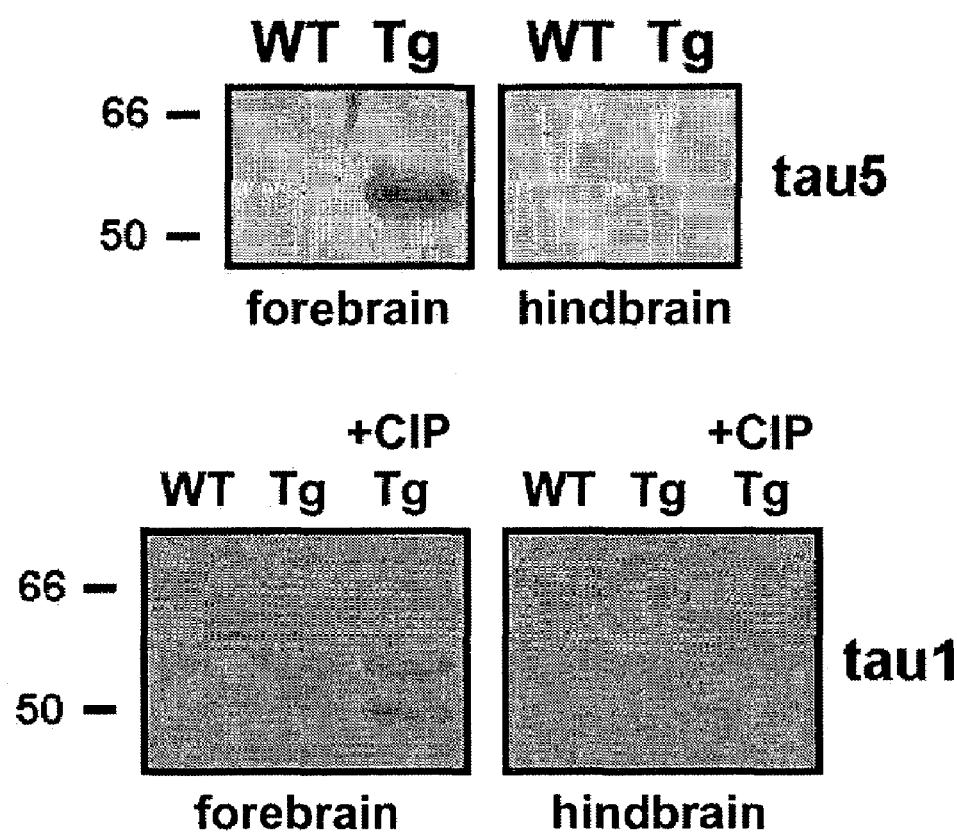
Figure 30:
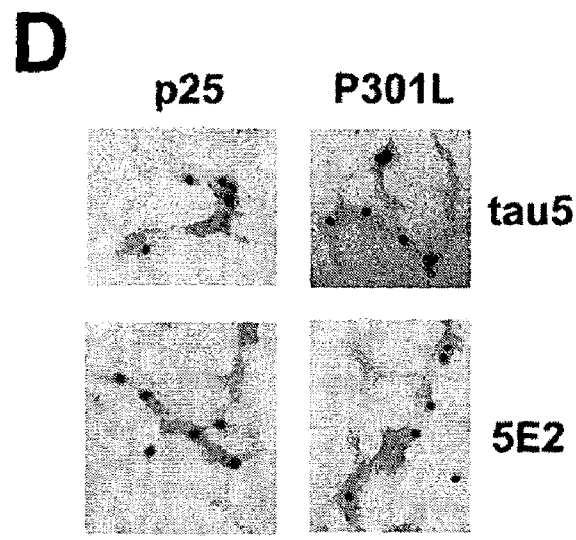
Figure 30:
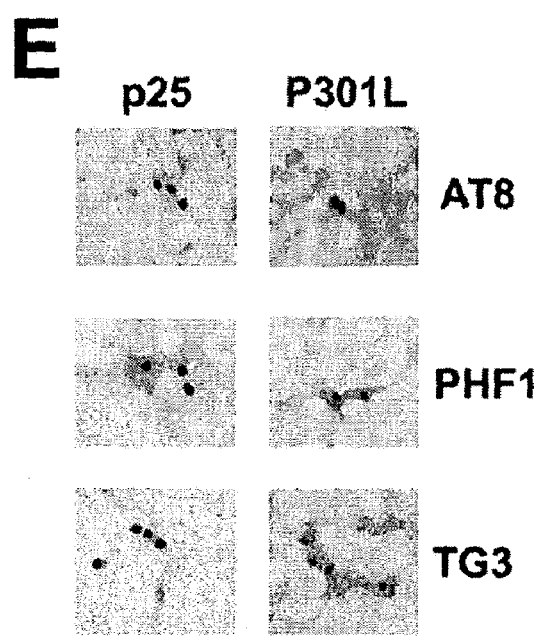
Figure 31:
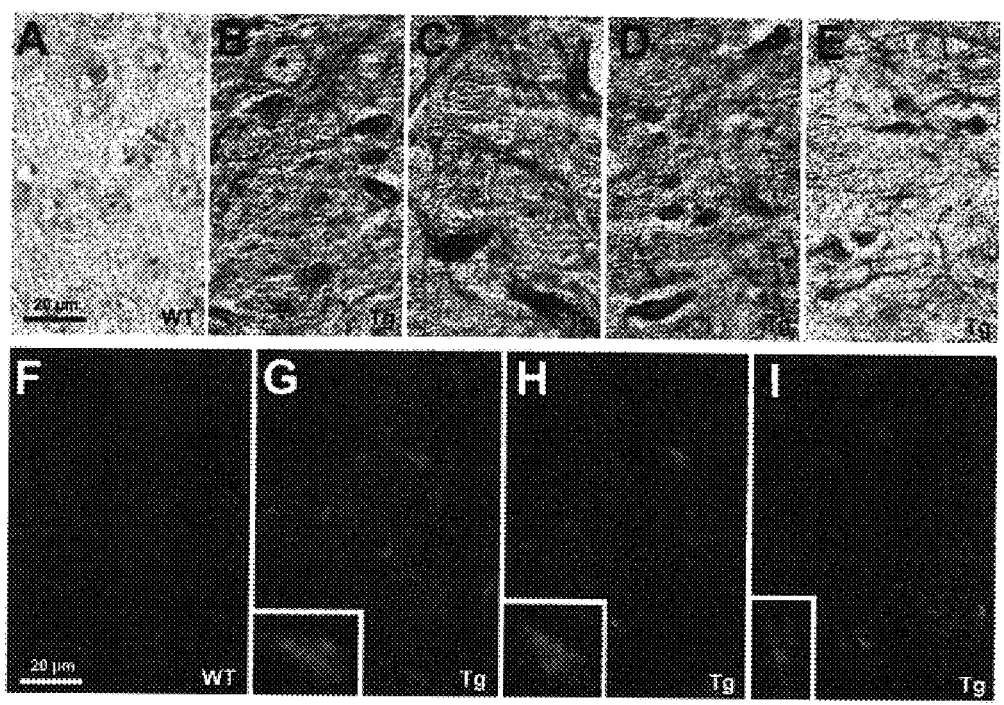
Figure 33:
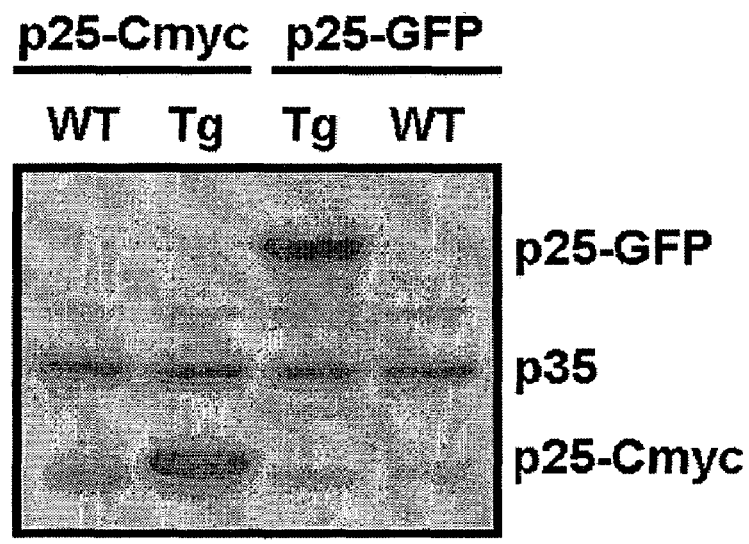
Figure 33:
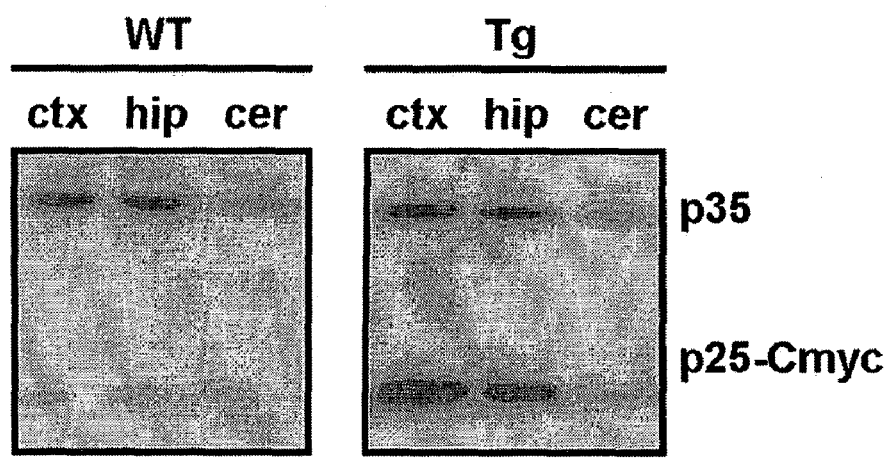
Figure 33:
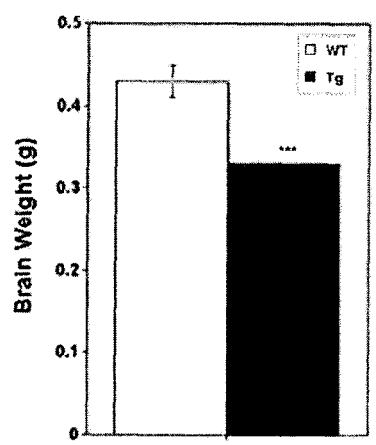
Figure 33:
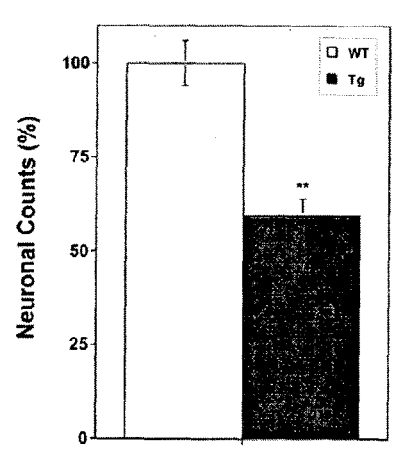
Figure 33:
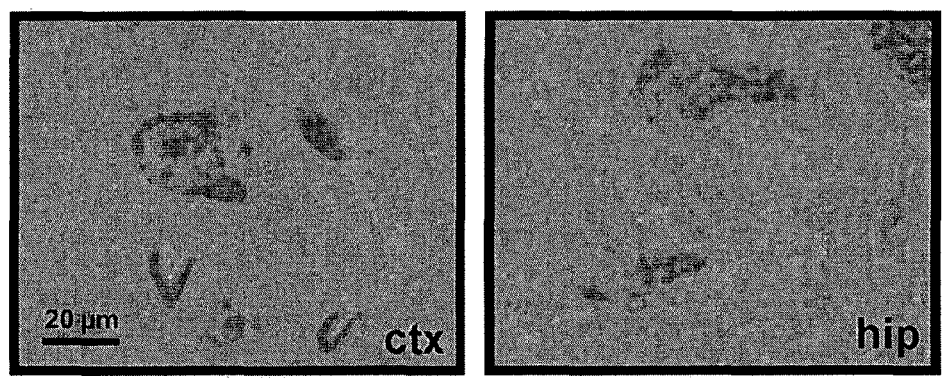

In forebrains of 8 and 12 week induced p25 Tg mice, a substantial portion of tau localized to the sarkosyl-insoluble fraction (FIG. 30A). Moreover, phosphorylation of tau in the sarkosyl-insoluble fraction was considerably increased in 12 week induced Tg mice (FIG. 30A). The p25-C-myc Tg mouse was analyzed (FIG. 33). In Tg mice induced for 15 weeks, there was less soluble tau with a concomitant increase in insoluble tau as compared to control mice (FIG. 30B). Similar results were also found in forebrains of 27 week induced Tg mice, in which insoluble tau accumulated and could be dephosphorylated upon phosphatase treatment (FIG. 30C). Furthermore, in hindbrains of these animals, which express low p25 levels, no accumulation of tau was observed (FIG. 30C). These observations demonstrate that tau aggregation progressively and selectively develops in forebrains of p25 Tg mice.

Considering the accumulation of aggregated tau in p25 Tg mice, the ultrastructure of the sarkosyl-insoluble fractions was examined using transmission electron microscopy. As shown by tau 5 and 5E2 immunogold labeling, which recognizes unphosphorylated and phosphorylated tau, numerous tau immunoreactive filaments were identified that had a diameter between 10 and 25 nm (FIGS. 30D and 30E). Interestingly, tau aggregates prepared from the forebrain of one year old Tg mice expressing the human tau P301L mutation (Lewis et al. (2000) *Nat. Genet.* 25:402) exhibited similar morphology to that of the p25 Tg mice (FIG. 30D). No immunogold labeling of these structures was found in WT mice. The aggregated tau filaments derived from both p25 and tau P301L Tg mice were also positive for phospho-tau epitopes, including S202/T205 (AT8) and S396/S404 (PHF1) (FIG. 30E). Furthermore, tau filaments from both sets of Tg mice were decorated with the TG3 antibody (FIG. 30E), a conformation-specific tau antibody that indicates the presence of hyperphosphorylated tau in an abnormal conformation state.

Sarkosyl-Insoluble Fractionation

Fractionation was performed based on methods previously described (Lewis et al. (2001) *Science* 293:1487). Forebrain halves from mice were homogenized in Tris buffered saline (TBS) and centrifuged at 100,000×g for 1 hour at 4° C. The pellet was resuspended in 0.8 M NaCl and 10% sucrose in TBS and centrifuged at 150,000×g for 15 min at 4° C. The concentration of the supernatant was adjusted to 1% sarkosyl, incubated at 37° C. for 1 hour, and centrifuged at 150,000×g for 30 min. The supernatant was collected as the sarkosyl-soluble fraction and the precipitate as the sarkosyl-insoluble fraction. Equal amounts (v/w) were subjected 8% SDS-PAGE and immunoblot analysis.

Electron Microscopy

In order to assess the sarkosyl-insoluble fractions at an ultrastructural level, aliquots were placed on 200 mesh copper Formvar/carbon-coated grids that were exposed for a 30 sec exposure to glow discharge in an Edwards Auto 306 vacuum evaporator. After blocking in 1% BSA, samples were incubated in primary antibody, followed by a rabbit anti-mouse bridging antibody. Bound antibodies were visualized by protein A-gold (10 nm), stained with 1% uranyl acetate, and viewed with a JEOL 1200EX transmission electron microscope. The following antibodies were used for immunogold labeling. Phosphorylation-independent tau antibodies (1:5-1:10) include tau 5 from Biosource International (Camarillo, Calif.) and 5E2 from K. Kosik. Phosphorylation-dependent tau antibodies include monoclonal antibodies AT8 from Innogenetics (Belgium) and PHF1 and TG3 from P. Davies.

EXAMPLE 17

NFT Pathology in p25 Tg Mice

To examine whether p25 Tg mice display late stage tangle structures, silver and Thioflavin-S stainings were used to analyze Tg mice that had been induced (i.e., not fed doxycycline) for over 27 weeks. Gallyas silver staining was selected as a representative of the available silver staining techniques since it shows much less nonspecific staining on normal cellular elements and is considered a specific stain for NFTs. In brains of Tg but not WT mice, classical AD-like tangles were found in the cortex and hippocampus, as indicated by the numerous intraneuronal and flame-shaped silver-positive cells in these brain regions (FIGS. 31A-31E). In addition, many neuropil threads, another pathological feature of AD, were clearly seen throughout the cortex and hippocampus as twisted neuritic structures and contorted neuronal cell processes (FIGS. 31B-31E). Thioflavin-S staining, a specific indicator for late stage tangles, was also performed in these mice. An abundant number of neurons was observed in the cortex and hippocampus that were positive for Thioflavin-S (FIGS. 31F-31I). No silver or Thioflavin-S positive structures were observed in WT or Tg mice induced for either 8 or 12 weeks. These results demonstrate that aberrant Cdk5 activity caused by p25 accumulation induces the formation of neuropil threads and endogenous tau filaments in the cortex and hippocampus of mice.

EXAMPLE 18

Model

Without intending to be bound by theory, the following working model is based in part on data presented herein (FIG. 32). Various neurotoxic conditions result in p35 cleavage by calpain to generate p25 and deregulate Cdk5 activity. Neurotoxic conditions include, but are not limited to, ischemia, glutamate exposure, $H_2O_2$ exposure, $A\beta(1-42)$ exposure, and the like. These conditions can be early events in the progression of neurodegenerative diseases. Over time and above a threshold level, p25 accumulation triggers a cascade of pathological events. This can be due in part to the different substrate specificities of p25 and p35 that arise from their different biochemical properties and subcellular localizations. One consequence of p25 accumulation is neuronal loss, which can result from the activation of multiple cell death mechanisms. In addition, dysregulated Cdk5 activity by p25 causes aberrant tau metabolism that leads to its hyperphosphorylation, disruption of its association with microtubules, and its increased aggregation. These pathogenic tau events ultimately culminate in the formation of NFTs. Interestingly, given that $A\beta$ can induce p25 generation indicates that Cdk5 can act as a molecular link between plaques and tangles, the two invariant hallmarks of AD. Abnormal activation of Cdk5 by p25 can also alter other signaling pathways that, in turn, contribute to pathogenesis. Improper activation of these signaling pathways can contribute to neuronal death and tau pathology.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference in their entirety for all purposes to the same extent as if each individual publication or patent application were specifically and individually indicated to be so incorporated by reference.

What is claimed:

1. A transgenic mouse whose genome comprises a first transgene comprising a DNA sequence encoding p25 operably linked to an inducible promoter, and a second transgene comprising a DNA sequence encoding an inducer of the inducible promoter operably linked to a calcium-calmodulin-dependent kinase II promoter, exhibiting one or more features selected from the group consisting of progressive nurodegeneration, tau aggregation, neurofibrillary tangle formation, aberrant cyclin-dependent kinase 5 activity, neuronal loss in the cerebral cortex, neuronal loss in the hippocampus, severe brain atrophy, reactive astrogliosis, caspase-3 activation, upregulation of C99, upregulation of beta amyloid, tau hyperphosphorylation, amyloid precursor protein phosphorylation, amyloid precursor protein hyperphosphorylation decreased body weight, decreased forebrain body mass and a decreased brain weight.

2. The transgenic mouse of claim 1, wherein the inducible promoter is a tetracycline responsive element.

3. The transgenic mouse of claim 1, wherein the inducer is a tetracycline-responsive transcriptional activator.

4. The transgenic mouse of claim 1, wherein the p25 is expressed in the brain.

5. The transgenic mouse of claim 1, wherein the p25 is expressed in the forebrain.

6. The transgenic mouse of claim 1, wherein the p25 is a murine p25.

7. The transgemic mouse of claim 1, wherein the p25 is a human p25.

8. The transgenic mouse of claim 1, wherein the transgenic mouse over-expresses p25 when compared to mouse not expressing the transgene comprising a DNA sequence encoding p25.

9. The transgenic mouse of claim 8, wherein the amyloid precursor protein phosphorylation or the amyloid precursor protein hyperphosphorylation occurs at one or more amino acid residues selected from the group consisting of tyrosine 653, serine 655, threonine 668, serine 675, tyrosine 682, threonine 686 and tyrosine 687.

10. The transgenic mouse of claim 1, exhibiting one or more behavioral symptoms of Alzheimer's disease.

11. A cell line established from the transgenic mouse of claim 1, wherein the cell line comprises a cell having a genome comprising a first transgene comprising a DNA sequence encoding p25 operably linked to an inducible promoter, and a second transgene comprising a DNA sequence encoding an inducer of the inducible promoter operably linked to a calcium-calmodulin-dependent kinase II promoter.

* * * * *

UNITED STATES PATENT AND TRADEMARK OFFICE
CERTIFICATE OF CORRECTION

| | |
|---|---|
| PATENT NO. | : 7,250,551 B2 |
| APPLICATION NO. | : 10/625986 |
| DATED | : July 31, 2007 |
| INVENTOR(S) | : Tsai et al. |

It is certified that error appears in the above-identified patent and that said Letters Patent is hereby corrected as shown below:

In the Specification

Column 1, under STATEMENT OF GOVERNMENT INTERESTS, Line 14-16:
Please delete "This invention was funded by NIH grant no. GM 53049. The U.S. Government may have certain rights to this invention." and insert --This invention was made with government support under GM053049 awarded by National Institutes of Health (NIH). The government has certain rights in this invention.--

Signed and Sealed this
Eleventh Day of October, 2022

Katherine Kelly Vidal
*Director of the United States Patent and Trademark Office*